US011471509B2

(12) United States Patent
Olson et al.

(10) Patent No.: US 11,471,509 B2
(45) Date of Patent: *Oct. 18, 2022

(54) COMPOSITIONS AND METHODS RELATING TO MYOMAKER-INDUCED MUSCLE CELL FUSION

(71) Applicant: The Board of Regents of the University of Texas System, Austin, TX (US)

(72) Inventors: Eric Olson, Dallas, TX (US); Douglas P. Millay, Frisco, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 322 days.

This patent is subject to a terminal disclaimer.

(21) Appl. No.: 16/379,610

(22) Filed: Apr. 9, 2019

(65) Prior Publication Data

US 2019/0358294 A1    Nov. 28, 2019

Related U.S. Application Data

(63) Continuation of application No. 14/900,005, filed as application No. PCT/US2014/044554 on Jun. 27, 2014, now Pat. No. 10,272,137.

(60) Provisional application No. 61/840,211, filed on Jun. 27, 2013.

(51) Int. Cl.
| | |
|---|---|
| *A61K 38/00* | (2006.01) |
| *A61K 38/17* | (2006.01) |
| *A61K 45/06* | (2006.01) |
| *C07K 14/47* | (2006.01) |
| *A61K 9/00* | (2006.01) |
| *C12N 5/16* | (2006.01) |
| *C12N 15/02* | (2006.01) |

(52) U.S. Cl.
CPC ........ *A61K 38/1719* (2013.01); *A61K 9/0019* (2013.01); *A61K 45/06* (2013.01); *C07K 14/4716* (2013.01); *C12N 5/16* (2013.01); *C12N 15/02* (2013.01); *C12N 2740/10043* (2013.01); *C12N 2740/10071* (2013.01)

(58) Field of Classification Search
None
See application file for complete search history.

(56) References Cited

U.S. PATENT DOCUMENTS

| | | | |
|---|---|---|---|
| 2004/0048249 | A1 | 3/2004 | Tang et al. |
| 2005/0265978 | A1 | 12/2005 | Chancellor et al. |
| 2016/0136240 | A1 | 5/2016 | Olson et al. |
| 2016/0168572 | A1* | 6/2016 | Lotvall .................. C12N 15/85 514/44 A |
| 2020/0060980 | A1 | 2/2020 | Von Maltzahn et al. |

FOREIGN PATENT DOCUMENTS

| | | | |
|---|---|---|---|
| SE | 1251290-1 | * | 11/2012 |
| WO | WO 2004/009834 | | 1/2004 |
| WO | WO 2006/028786 | | 3/2006 |
| WO | WO 2006/059141 | | 6/2006 |
| WO | WO 2011/058052 | | 5/2011 |
| WO | WO 2012/031008 | | 3/2012 |
| WO | WO 2012/149376 | | 11/2012 |
| WO | WO 2014/076137 | | 5/2014 |
| WO | WO 2014/210448 | | 12/2014 |
| WO | WO 2015/110957 | | 7/2015 |
| WO | WO 2016/138525 | | 9/2016 |
| WO | WO 2016/183482 | | 11/2016 |
| WO | WO 2018/208728 | | 11/2018 |

OTHER PUBLICATIONS

NCBI Blast Search for SEQ ID No. 1, downloaded Sep. 21, 2021; pp. 1-2.*
Glycogen storage disease type II—Wikipedia p. 1 of 7; downloaded Sep. 22, 2021.*
Van Dommelen et al., Journal of Controlled Release 161 (2012) 635-644 Review Microvesicles and exosomes: Opportunities for cell-derived membrane vesicles in drug delivery.*
Abmayr and Pavlath, "Myoblast fusion: lessons from flies and mice," *Development*, 139:641-656, 2012.
Buckingham, "Myogenic progenitor cells and skeletal myogenesis in vertebrates," *Curr Opin Genet Dev*, 16:525-532, 2006.
Chen and Olson, "Antisocial, an intracellular adaptor protein, is required for myoblast fusion in Drosophila," *Dev Cell*, 1:705-715, 2001.
Chen and Olson, "Unveiling the mechanisms of cell-cell fusion," *Science*, 308, 369-373, 2005.
Chen et al., "Control of myoblast fusion by a guanine nucleotide exchange factor, loner, and its effector ARF6," *Cell*, 114:751-762, 2003.
Gruenbaum-Cohen et al., "The actin regulator N-WASp is required for muscle-cell fusion in mice," *Proc Natl Acad Sci USA*, 109:11211-11216, 2012.
Kang and Krauss, "Muscle stem cells in developmental and regenerative myogenesis," *Curr Opin Clin Nutr Metab Care*, 13:243-248, 2010.
Laurin et al., "The atypical Rac activator Dock180 (Dock1) regulates myoblast fusion in vivo," *Proc Natl Acad Sci USA*, 105:15446-15451, 2008.
Millay et al., "Myomaker: a membrane activator of myoblast fusion and muscle formation," *Nature*, 499(7458):301-305, 2013.
Nowak et al., "Nap1-mediated actin remodeling is essential for mammalian myoblast fusion," *J Cell Sci*, 122:3282-3293, 2009.
Office Action issued in U.S. Appl. No. 14/900,005, dated Apr. 16, 2018.
PCT International Preliminary Report on Patentability issued in International Application No. PCT/US2014/044554, dated Jan. 7, 2016.

(Continued)

*Primary Examiner* — Maria G Leavitt
(74) *Attorney, Agent, or Firm* — Parker Highlander PLLC

(57) ABSTRACT

The present disclosure describes the fusogenic activity of the Myomaker protein. This polypeptide, when expressed in non-muscle cells, is able to drive fusion of the cell with a muscle cell, but not with other non-muscle cells. The use of this protein and cell expressing it in the delivery of exogenous genetic material to muscle cells also is described.

8 Claims, 29 Drawing Sheets

Specification includes a Sequence Listing.

(56) References Cited

OTHER PUBLICATIONS

PCT International Search Report and Written Opinion issued in International Application No. PCT/US2014/044554, dated Oct. 29, 2014.
Pei et al., "CREST—a large and diverse superfamily of putative transmembrane hydrolases," *Biology Direct,* 6:37, 2011.
Powell and Wright, "Jamb and jamc are essential for vertebrate myocyte fusion," *PLoS Biol,* 9:e1001216, 2011.
Shi et al., "Requirement of the fusogenic micropeptide myomixer for muscle formation in zebrafish," *PNAS,* 114(45): 11950-11955, 2017.
Shilagardi et al., "Actin-propelled invasive membrane protrusions promote fusogenic protein engagement during cell-cell fusion," *Science,* 340:359-363, 2013.
USPTO Sequence Search, Mar. 31, 2016; example pp. 1-4.
Vasyutina et al., "The small G-proteins Rac1 and Cdc42 are essential for myoblast fusion in the mouse," *Proc Natl Acad Sci USA,* 106:8935-8940, 2009.
Wilson and Snell, "Microvilli and cell-cell fusion during fertilization," *Trends Cell Biol,* 8:93-96, 1998.
Alvarez-Erviti et al., "Delivery of siRNA to the mouse brain by systemic injection of targeted exosomes." Nature Biotechnology (2011) 29(4): 341-345.

\* cited by examiner

Tongue

E16

P2

Control | Cardiotoxin injury

H&E

X-gal

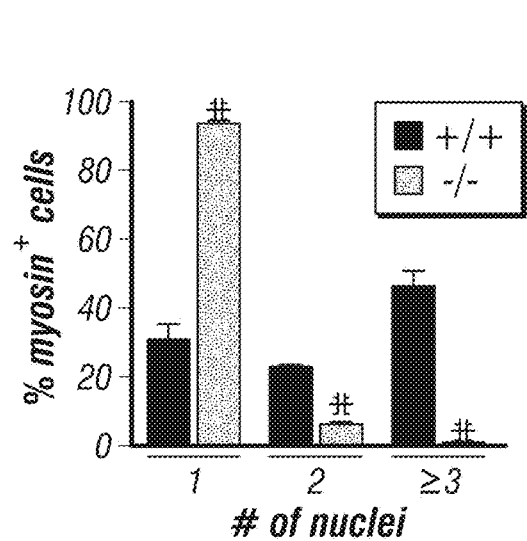
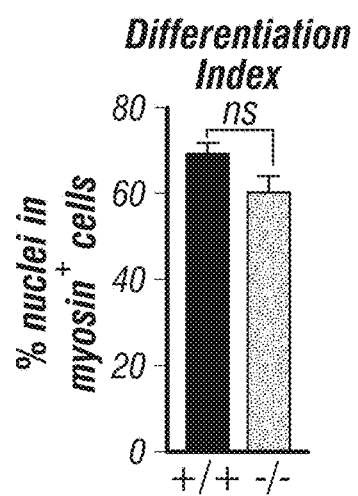
FIG. 3B
FIG. 3C
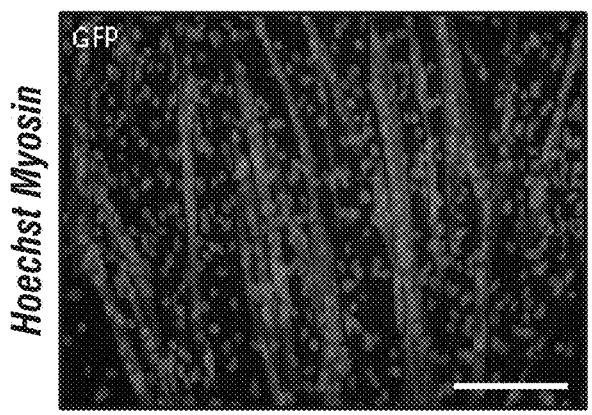
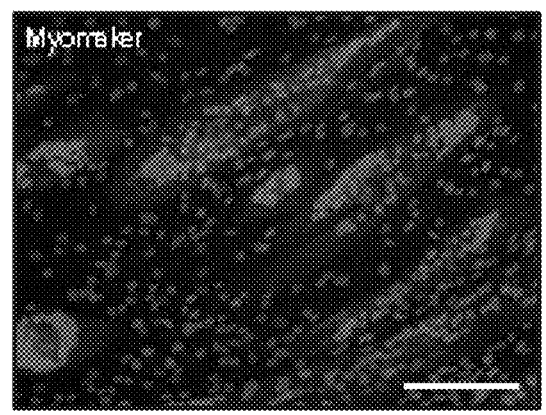
FIG. 3D
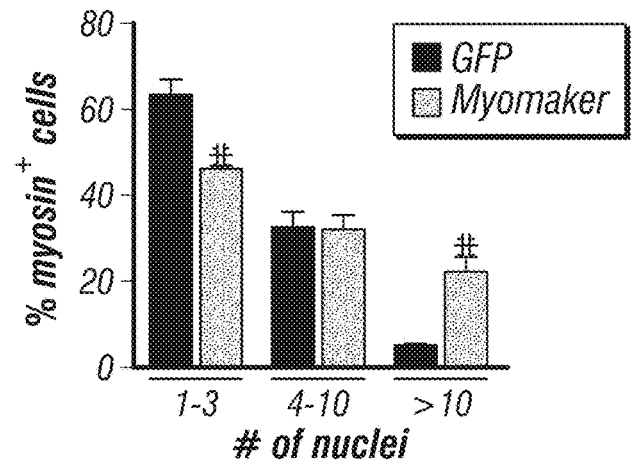
FIG. 3E

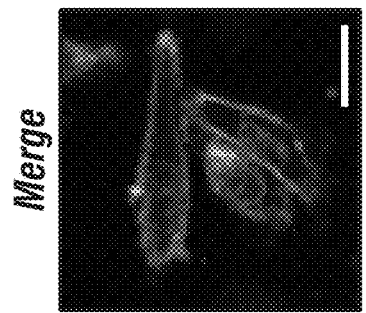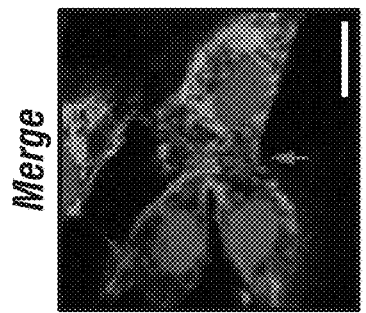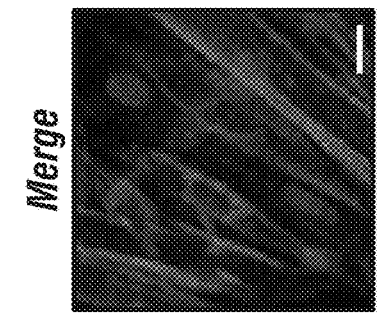
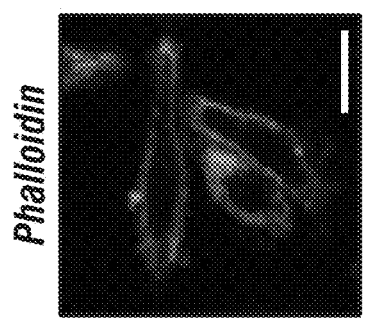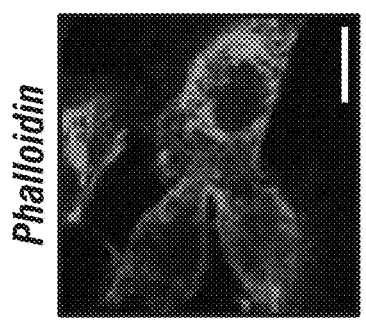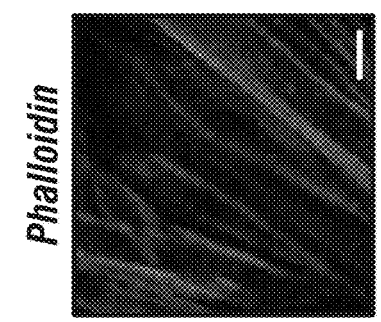
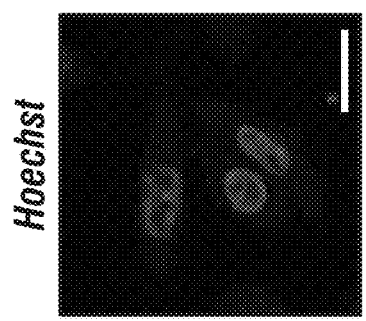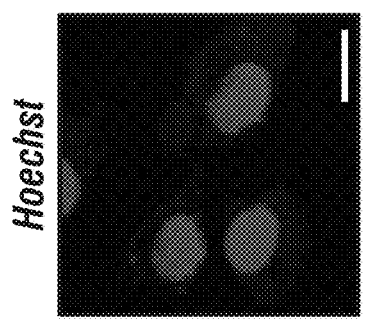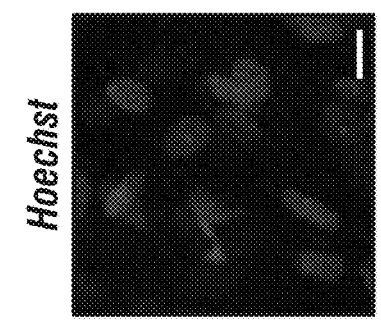
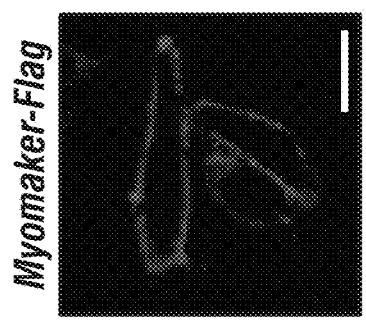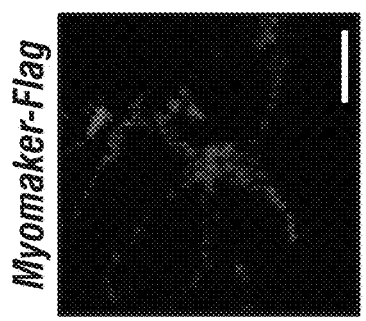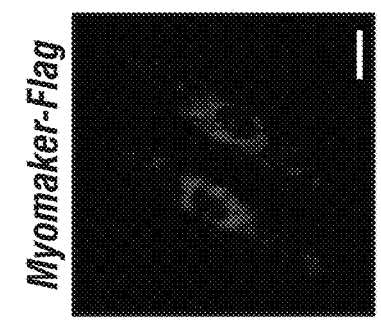
FIG. 4A  FIG. 4B  FIG. 4C

|  |  |  | myomaker | | |
|---|---|---|---|---|---|
| Age | Total pups |  | +/+ | +/- | -/- |
| E15 | 50 | Observed | 13 (26%) | 24 (48%) | 13 (26%) |
|  |  | Expected | 13 (25%) | 25 (50%) | 13 (25%) |
| E17.5 | 25 | Observed | 8 (32%) | 11 (44%) | 6 (24%) |
|  |  | Expected | 6 (25%) | 13 (50%) | 6 (25%) |
| P7 | 57 | Observed | 24 (42%) | 33 (58%) | 0 |
|  |  | Expected | 14 (25%) | 29 (50%) | 14 (25%) |

```
Human     MGTLVAKLLLPTLSSLAFLPTVSIAAKRRFHMEAMVYLFTLFFVALHHACNGPGLSVLCF  60
Dog       MGTLAAKLLLPTLSSLAFLPTVSIAAKRRFHMEAMVYLFTMFFVALHHACNGPGLSVLCF  60
Pig       MGTVMAKLLLPTLSSLAFLPTVSIAAKRRFHMEAMVYLFTTFFVAFYHACHGPGLAMICF  60
Mouse     MGTVVAKLLLPTLSSLAFLPTVSIATKRRFYMEAMVYLFTMFFVAFSHACDGPGLSVLCF  60
Oppossum  MGTLVTKLLLPTISSLAFLPTISIAAKRRFHMEAMVYLFTMFFIAIYHACDGPGLSVLCF  60
Zebrafish MGAFIAKMLLPTISSLVFVPAASVAAKRGFHMEAMVYFFTMFFTAIYHACDGPGLSILCF  60
          **:: ::****:***:.:*:.  *::***.****** *:*:**.*::**.****::.**

Human     MRHDILEYFSVYGTALSMWVSLMALADEDEPKRSTFVMFGVLTIAVRIYHDRWGYGVYSG  120
Dog       MRHDVLEYFSVYGTALSMWVSLMALADEDEPKRSTFVMFGVLTIAVRIYHDRWGYGVYSG  120
Pig       LRLDILEYFSVYGTALSMWVSLMALADEDEPKRSTFVMFGVLTIAVRIYHDRWGYGVYSG  120
Mouse     MRRDILEYFSIYGTALSMWVSLMALADEDEPQRSTFTMLGVLTIAVRTFHDRWGYGVYSG  120
Oppossum  MRYDILEYFSIYGTALSMWVSLMALAEFDEDPKRSTFVMFGVLTIAVRIYQDRWGYGVYSG  120
Zebrafish MKYDILEYFSVYGTAISMWVTLLALGDFDEPKRSSLTMFGVLTAAVRIYQDRLGYGIYSG  120
          :: .:******:****:****.*:**: : ::*:*:.:*:** ** .:* ***:***
```

*FIG. 10A*

| | | |
|---|---|---|
| Human | PIGTAILIIAAKWLQKMKEKKGLYPDKSVYTQQIGPGLCFGALALMLRFFFEEDWDYTYVH | 180 |
| Dog | PIGTAVLIIATKWLQQMKEKKSLYPDKSVYTQQIGPGLCFGALALMLRFFEEDWDYTYVH | 180 |
| Pig | PIGTAALIIAAKWLQQMKDQRRLYPDKSVYTQQIGPGLCFGALALMLRFFFEEWDYTYVH | 180 |
| Mouse | PIGTATLIIAVKWLKKMKEKKGLYPDKSIYTQQIGPGLCFGALALMLRFFEEDWDYTYVH | 180 |
| Opossum | PIGTAVLIITATKWLQKMKEKKGLYPDKSVYTQQIGPGFCFGALALMLRFFFQEWDYTYVH | 180 |
| Zebrafish | PIGTAVFMITVKWLQKMKEKKGLYPDKSVYTQQVGPGCCFGALALMLRFYFEEWDYAYVH | 180 |
| | **::.:..: **:**.:*.**********:.:*:.*** | |
| Human | SFYHCALAMSFVLLLPKVNKKAGSPGTPAKLDCSTLCCACV | 221 |
| Dog | SFYHCALAMSFVLLLPKVNKKAGSAGPPAKLDCSTLCCACI | 221 |
| Pig | SFYHCALAMSFVLLLPKANKKAGSAGPPAKLDCSTLCCACI | 221 |
| Mouse | SFYHCALAMSFVLLLPKVNKKAGNAGAPAKLTFSTLCCTCV | 221 |
| Opossum | SFYHCSLAMSFVLLLPKVNKKAGNAGTPAKLDCSTLCCACI | 221 |
| Zebrafish | SFYHVSLAMSFILLLPKKNRYAGTGRNAAKLNCYTLCCCV- | 220 |
| | **..:*..:  . : * ** | |

*FIG. 10A (Cont'd)*

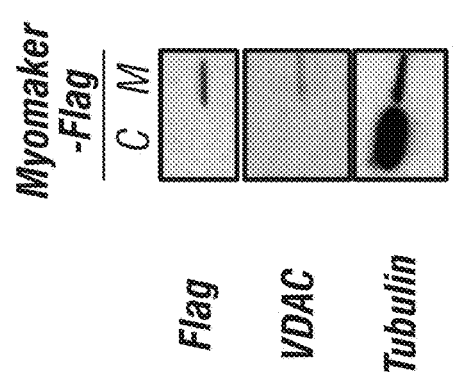
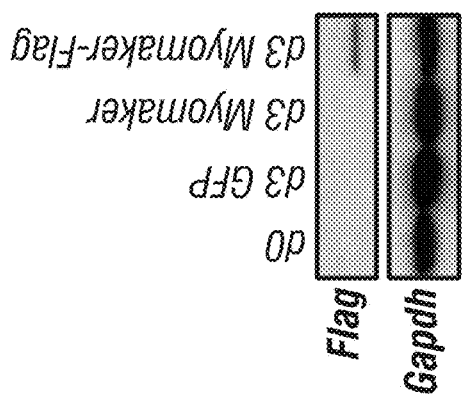
FIG. 11A
FIG. 11B
FIG. 11C

COMPOSITIONS AND METHODS RELATING TO MYOMAKER-INDUCED MUSCLE CELL FUSION

This application is a continuation of U.S. application Ser. No. 14/900,005, filed Dec. 18, 2015, now issued as U.S. Pat. No. 10,272,137, which is a national phase application under 35 U.S.C. § 371 of International Application No. PCT/US2014/044554, filed Jun. 27, 2014, which claims benefit of priority to U.S. Provisional Application 61/840,211, filed Jun. 27, 2013, the entire contents of each of which are hereby incorporated by reference.

GOVERNMENT FUNDING CLAUSE

This invention was made with government support under F32AR05948403, HL-077439, HL-111665, HL093039 and U01-HL-100401 awarded by the National Institutes of Health. The government has certain rights in the invention.

BACKGROUND OF THE INVENTION

1. Field of the Invention

The present invention relates generally to the fields of developmental biology, cell biology and molecular biology. More particularly, it relates the muscle cell fusion activity of the Myomaker protein.

2. Description of Related Art

Myoblast fusion is a complex and tightly controlled process required for the formation of skeletal muscle fibers (Chen and Olson, 2005). The fusion process must be highly cell type-specific to ensure that fusogenic myoblasts do not form syncytia with non-muscle cell types. While the transcriptional mechanisms governing skeletal muscle development have been elucidated in detail (Bentzinger et al., 2012; Berkes and Tapscott, 2005; Buckingham 2006; Kang and Krauss, 2010), the mechanisms that coordinate myoblast fusion remain poorly understood, and no muscle-specific protein that directly regulates myoblast fusion has been identified in any organism (Abmayr & Pavlath, 2012; Rochlin et al., 2010). In contrast, numerous proteins involved in cell-cell adhesion and actin dynamics have been implicated in myoblast fusion (Charrasse et al., 2007; Charrasse et al., 2002; Schwander et al., 2003; Griffinet et al., 2009; Yagami-Hiromasa et al., 1995). However, none of these proteins are muscle-specific, necessary and sufficient for mammalian myoblast fusion, suggesting that muscle-specific components of this process remain to be discovered.

SUMMARY OF THE INVENTION

Thus, in accordance with the present disclosure, there is provided a cell transformed with an exogenous nucleic acid encoding a Myomaker polypeptide under the control of a promoter active in said cell. The cell may be a human cell, a non-muscle cell, such as a fibroblast, bone marrow cell or blood cell. The exogenous nucleic acid may be under the control of constitutive promoter or an inducible promoter. The exogenous nucleic acid may be incorporated into a chromosome of said cell. The exogenous nucleic acid may be carried episomally by said cell. The cell may express a detectable marker. The cell may be transformed to express a gene of interest other than Myomaker.

In another embodiment, there is provided a method of preparing a non-muscle cell fusion partner comprising transferring into a non-muscle cell a nucleic acid acid encoding a Myomaker protein under the control of a promoter active in said cell. The cell may be stably transformed, or may be transiently transfected. The method may further comprise transferring into said cell a nucleic acid encoding or sufficient to produce a detectable marker. The exogenous nucleic acid may be under the control of constitutive promoter or an inducible promoter. The cell may be a human cell. The cell may be a fibroblast, bone marrow cell or blood cell. The exogenous nucleic acid further encodes a selectable marker. The cell may be transformed to express a gene of interest other than Myomaker.

In still another embodiment, there is provided a method of fusing a non-muscle cell to a muscle cell comprising (a) providing a non-muscle cell expressing an exogenous Myomaker protein in said non-muscle cell; and (b) contacting said non-muscle cell with a muscle, wherein said non-muscle cell expressing Myomaker protein will fuse with said muscle cell. The non-muscle cell may be a human cell, and/or may be a fibroblast, bone marrow cell or blood cell. Step (b) may be performed in vitro or in vivo. The non-muscle cell may express a detectable marker, and/or a selectable marker. The muscle cell may be an isolated muscle cell or a muscle cell is located in intact muscle tissue. The muscle cell may be a myoblast.

In yet another embodiment, there is provided method of delivering a gene of interest to a muscle cell comprising (a) providing a non-muscle cell expressing an exogenous Myomaker protein, wherein said non-muscle cell further comprises a gene of interest; and (b) contacting said non-muscle cell with a muscle, wherein said non-muscle cell expressing Myomaker protein will fuse with said muscle cell and deliver said gene of interest to said muscle cell. The non-muscle cell may be a human cell, and/or may be a fibroblast, bone marrow cell or blood cell. Step (b) may be performed in vitro or in vivo. The non-muscle cell may express a detectable marker, and/or a selectable marker. The muscle cell may be an isolated muscle cell or a muscle cell is located in intact muscle tissue. The muscle cell may be a myoblast. The muscle cell may be a myoblast.

The muscle cell may exhibit a pathologic phenotype, and said gene of interest correct said genotype. The pathologic phenotype may be the underexpression or absence of a normal gene product, or the expression of a defective gene product. The pathologic phenotype may be associated with congenital myopathy, sarcopenia, amyotrophic lateral sclerosis, muscular dystrophy, Pompe disease or rhabdomyosarcoma. The non-muscle cell may be delivered to an affected muscle tissue comprising said muscle in a subject, such as by intramuscular injection. The delivery may be repeated at least once. A secondary therapy may be administered to said subject. The non-muscle cell may be delivered to said muscle cell ex vivo and subsequently implanted in to a subject, such as by contacting intact muscle tissue ex vivo.

As used herein the specification, "a" or "an" may mean one or more. As used herein in the claim(s), when used in conjunction with the word "comprising," the words "a" or "an" may mean one or more than one. As used herein "another" may mean at least a second or more. Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 1A) In situ hybridization for Myomaker in WT embryos illustrates muscle specificity. (FIG. 1B) qPCR for Myomaker, Myogenin, and MyoD on tongues at the indicated ages shows down-regulation after myogenesis. (FIG. 1C) Gene expression during differentiation of C2C12 myoblasts. (FIG. 1D) X-gal staining on E16 and P2 Myomaker$^{+/-}$ (Myomaker-LacZ) mice confirms expression in all skeletal muscles. (FIG. 1E) Cardiotoxin-injured and X-gal stained tibialis anterior (TA) muscle from 6 week-old Myomaker$^{+/-}$ mice shows the re-activation of Myomaker. Serial H&E stained sections indicate muscle injury. Control represents uninjured contralateral TA. Scale bars: FIGS. 1A and 1D, 2 mm; FIG. 1E, 200 µm.

(FIG. 2A) Full term WT (+/+) and Myomaker$^{-/-}$ embryos were dissected and skinned to illustrate the lack of muscle surrounding Myomaker$^{-/-}$ limbs. (FIG. 2B) Paraffin sectioning and H&E staining on tongues reveal a lack of muscle fibers in E17.5 Myomaker$^{-/-}$ embryos. (FIG. 2C) Longitudinal sections of E14 hindlimb muscles stained with a myosin antibody to determine multi-nucleation of muscle cells. WT limbs exhibit myofibers containing multiple nuclei, absent in Myomaker$^{-/-}$ sections. Scale bars: FIG. 2A, 2 mm; FIG. 2B, 100 µm; FIG. 2C, 40 µm.

FIGS. 3A-E. Control of myoblast fusion by Myomaker. (FIG. 3A) Myoblasts from WT (+/+) and Myomaker$^{-/-}$ E17 embryos were differentiated for 3 days, and stained for myosin and a nuclear stain (Hoechst). Myomaker$^{-/-}$ myoblasts failed to fuse. (FIG. 3B) Quantitation of the number of nuclei present in a myosin$^+$ cell indicates Myomaker$^{-/-}$ myoblasts cannot form myotubes with three or more nuclei. (FIG. 3C) Differentiation index, calculated as the percentage of nuclei in myosin$^+$ cells, indicated null myoblasts can activate the myogenic program. (FIG. 3D) C2C12 cells infected with a retrovirus encoding GFP or Myomaker were induced to differentiate for 4 days then stained with a myosin antibody and Hoechst (nuclei). (FIG. 3E) Quantitation of the percentage of myosin$^+$ cells that contained the indicated number of nuclei. Quantification was performed after 3 days of differentiation in FIG. 3B), FIG. 3C, and after 4 days in FIG. 3E. Scale bars: FIG. 3A, 100 µm, FIG. 3E, 200 µm. Data are presented as mean±SEM from three independent experiments. *P<0.05 compared to +/+ in FIG. 3B, FIG. 3C or GFP-infected cells in FIG. 3E. ns in FIG. 3C is not statistically significant.

FIGS. 4A-C. Myomaker is expressed on the cell membrane of myoblasts. (FIG. 4A) C2C12 cells were infected with Myomaker-Flag and live cells were stained 2 days after differentiation with Flag antibody on ice. After Flag staining, cells were then fixed and permeabilized and stained with Phalloidin (F-actin) and Hoechst (nuclei) to illustrate cell membrane localization of Myomaker-Flag. (FIG. 4B) Cells were stained as in FIG. 4A to visualize Myomaker-Flag in fusing cultures. The red arrow depicts sites of cell-cell interaction. (FIG. 4F) Myomaker-Flag infected C2C12 cells were fixed, permeabilized, and stained with Flag antibody, Phalloidin, and Hoechst showing the vesicle localization of the intracellular protein. Scale bars: 20 µm.

(FIG. 5A) Myomaker$^{+/-}$ and Myomaker$^{-/-}$ myoblasts express LacZ, and were either plated alone or mixed with WT myoblasts, induced to differentiate for 4 days, and stained with X-gal and nuclear fast red to determine the amount of fusion. Myomaker$^{+/-}$ myoblasts, alone or in the presence of WT myoblasts fused normally, illustrated by myotubes with robust LacZ staining. Myomaker$^{-/-}$ myoblasts alone exhibited an inability to fuse. Addition of WT myoblasts to Myomaker$^{-/-}$ myoblasts resulted in chimeric myotubes (arrow) indicating fusion between the two cell populations. (FIG. 5B) Quantitation of the percentage of LacZ$^+$ myotubes containing ≥3 nuclei shows null myoblasts can only form myotubes with three or more nuclei in the presence of WT myoblasts. (FIG. 5C) Phalloidin and Flag staining of C2C12 myoblasts after infection with Myomaker-Flag illustrates the lack of Flag staining in myotubes. (FIG. 5D) 10T1/2 fibroblasts were infected with GFP-retrovirus and either Empty- or Myomaker-retrovirus and then mixed with C2C12 cells and differentiated. Myotube formation was monitored by myosin staining, and fusion of fibroblasts was determined by visualization of GFP in myosin$^+$ myotubes. Myosin$^+$ GFP$^+$ myotubes (arrowheads) are evident in cultures containing Myomaker-infected fibroblasts, whereas myosin$^+$ GFP$^-$ myotubes (arrows) were observed in Empty-infected cultures. (FIG. 5E) Quantitation of the percentage of GFP$^+$ fibroblasts, infected with Empty- or Myomaker-retrovirus, that fused to myosin$^+$ myoblasts. Scale bars: FIG. 5A, 100 µm; FIG. 5C, 20 µm; FIG. 5D, 200 µm. Data are presented as mean±SEM from three independent experiments. *P<0.05 compared to –/– in FIG. 5B and compared to empty in FIG. 5E.

(FIG. 6A) E9.5 and 11.5 embryos were sectioned transversely and radioisotopic in situ hybridizations for Myomaker, Myogenin, and M-cadherin were performed. Each transcript exhibited expression in the somites at E9.5 and in the entire myotome of E11.5 embryos. The myomaker gene is expressed at relatively lower levels at E9.5 compared to E11.5. The top of the embryos pictured is rostral and the bottom caudal. Images were captured using darkfield microscopy, converted to red pseudo color, and overlayed on a brightfield image. (FIG. 6B) RNA was isolated from multiple tissues of E19 wild-type embryos and assessed for the presence of Myomaker transcripts by Northern blot. (FIG. 6A) Quantitative real-time PCR for Myomaker on the same tissues as in FIG. 6B. Scale bars: 200 µm.

(FIG. 7A) An IRES-β-galactosidase and neomycin cassette was inserted in intron 1. The strong splice acceptor site (E2SA) results in a myomaker-LacZ fusion and interruption of downstream transcription, generating a null allele. These targeted ES cells were obtained from KOMP as described in Materials and Methods. (FIG. 7B) Tissues harvested from P6 myomaker+/– mice were stained with X-gal. Myomaker-LacZ expression was not detected in any non-skeletal muscle tissues. (FIG. 7C) X-gal staining on forelimbs from myomaker+/– embryos demonstrates expression in muscle fibers. The b denotes bones. (FIG. 7D) Quadriceps from P6 WT, and P6 and P26 myomaker+/– mice were stained with X-gal to visualize postnatal down-regulation of the myomaker-LacZ allele. (FIG. 7E) WT tibialis anterior (TA) muscle was injured with cardiotoxin and analyzed for myomaker transcripts by qPCR at day 0, 3, and 7 after injury. (FIG. 7F) Myomaker RNA was absent from the tongue muscle of E13.5, E14, and E15 myomaker−/− embryos. Data are presented as mean±SEM. *$P<0.05$ compared to +/+. (FIG. 7G) Myomaker null embryos were obtained at expected Mendelian frequencies at E15 and E17.5. However, we did not observe a myomaker knockout at P7 due to lethality. Scale bars: FIG. 7B, FIG. 7D, 2 mm; FIG. 7C, 200 μm.

(FIG. 8A) Paraffin sectioning and H&E staining on diaphragm and intercostal muscles reveal a lack of muscle fibers in E17.5 myomaker−/− embryos. The b denotes bones. The d denotes diaphragm. (FIG. 8B) Masseter muscle from E15 and E17.5 WT and myomaker−/− embryos was paraffin sectioned and H&E stained to demonstrate the necessity of myomaker for formation of skeletal muscles of the head. (FIG. 8C) MyoD in situ hybridization shows comparable expression in E12 WT and myomaker−/− embryos. (FIG. 8D) qPCR for myogenin revealed no differences at the indicated ages in the tongues of WT (n=3) and myomaker (n=3) null mice. Data are presented as mean±SEM. (FIG. 8E) E14 forelimbs and E15 diaphragm were sectioned and stained with routine H&E. Myomaker−/− muscle is present at this stage of development in the forelimbs and diaphragm. The b denotes bones of the limb. The d shows the diaphragm. Scale bars, 200 μm for forelimb and 100 μm for diaphragm. (FIG. 8F) Desmin staining on WT and myomaker−/− E15 forelimbs demonstrates the presence of muscle cells. The b denotes bones. (FIG. 8G) E15 forelimbs were stained for DNA fragmentation with the TUNEL reaction and co-stained with DAPI. Apoptotic nuclei were more readily detected in myomaker−/− muscle compared to WT muscle. Scale bars: FIGS. 8A, 8B, 8F, 8G, 200 μm; FIG. 8C, 2 mm FIGS. 9A-H. Myomaker governs fusion and not the levels of myogenic proteins. FIGS. 9A, 9C, 100 μm; FIG. 9F, 20 μm.

FIGS. 10A-B. Myomaker amino acid conservation and hydrophobicity. (FIG. 10A) Amino acid alignment of myomaker proteins from Human, Dog, Pig Mouse, Opposum, and Zebrafish shows strong conservation. (FIG. 10B) Kyte-Doolittle plot for myomaker-Flag shows its highly hydrophobic nature. Regions above the horizontal line are considered hydrophobic. Flag, denoted by the green line, was engineered after amino acid 61 of myomaker.

FIGS. 11A-D. Myomaker-Flag localizes to membrane compartments. (FIG. 11A) C2C12 cells were infected with the indicated retroviruses and a Western blot analysis using a Flag antibody detected expression of myomaker-Flag in whole cell lysates. (FIG. 11B) Myomaker-Flag was overexpressed in C2C12 cells to test for its ability to increase myoblast fusion at levels similar to untagged myomaker. Cells were stained 4 days after differentiation. (FIG. 11C) C2C12 cells were lysed in hypotonic buffer and the cytosol (C) and membrane (M) fractions were obtained using differential centrifugation. Western blot analysis using a Flag antibody detected myomaker-Flag protein only in the membrane fraction. Detection of VDAC (voltage dependent anion channel) for the membrane fraction and tubulin for the cytosolic fraction was used to show efficient separation of the cellular compartments. (FIG. 11D) C2C12 cells were infected with myomaker-Flag and immunostained on day 2 of differentiation to assess co-localization with known proteins that are specific for certain intracellular compartments. Specifically, the cells were fixed and permeabilized and stained with Flag antibody and either Early Endosome Antigen 1 (EEA1, endosomes), Golgi matrix protein (GM130), Cyclophilin D (mitochondria), or protein disulfide isomerase (PDI, endoplasmic reticulum). Nuclei were stained using Hoechst. Myomaker-Flag exhibited partial co-localization with endosomes and ER. Scale bars: 20 μm.

(FIG. 12A) C2C12 myoblasts were infected with either GFP- or myomaker-retrovirus and differentiated in the presence of vehicle (0.1% EtOH), cytochalasin D, or lantrunculin. Myomaker over-expression did not overcome the deleterious effects of actin inhibition on myoblast fusion. (FIG. 12B) Live staining of C2C12 cells after infection with myomaker-Flag virus with and without cytochalasin D treatment demonstrates that actin dynamics does not regulate location of myomaker on the cell surface. Scale bars: FIG. 12A, 200 μm; FIG. 12B, 20 μm FIGS. 13A-B. BrdU+ myomaker+ fibroblasts fuse to C2C12 myoblasts.

DESCRIPTION OF ILLUSTRATIVE EMBODIMENTS

Figure 1A:
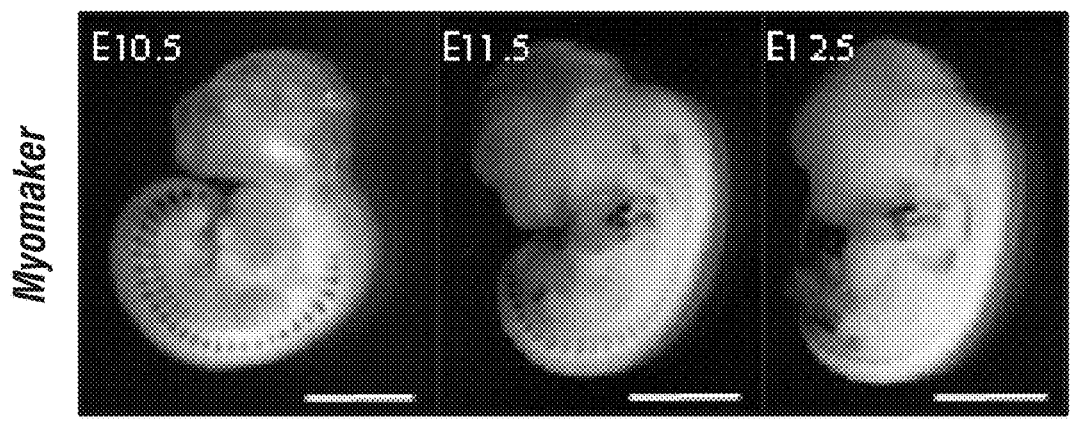
FIGS. 1A-E. Muscle-specific expression of Myomaker.

There are multiple types of membrane fusion, including virus-cell fusion, intracellular vesicle fusion, and cell-cell fusion (Chen and Olson 2005). Similarities exist between different fusion mechanisms, but relatively little is known about cell-cell fusion compared to other fusion processes, especially with respect to the fusogenic proteins that directly merge intercellular membranes. The inventors describe here the discovery of a muscle-specific membrane protein called Myomaker that is transiently expressed during myoblast fusion and is both necessary and sufficient to drive merger of plasma membranes in vivo and in vitro. Myomaker is a muscle-specific plasma membrane protein expressed specifically during times of myoblast fusion, and required for the formation of multinucleated myofibers. While surface glycoproteins, including cadherins, ß-1 integrin, MOR23, and Adam12 (Charrasse et al., 2007, Charrasse et al., 2002, Schwander et al., 2003, Griffinet et al., 2009 and Yagami-Hiromasa et al., 1995), have been shown to influence myoblast fusion, Myomaker is the only muscle-specific protein yet identified that is absolutely essential for myoblast fusion in vivo. The absence of multinucleated myofibers in Myomaker$^{-/-}$ mice demonstrates the requirement of this membrane protein for the formation of all skeletal muscles.

Myoblast fusion is a multistep process requiring intimate cell-cell interaction followed by membrane coalescence accompanied by actin-cytoskeletal dynamics that drive cell merger. Myomaker clearly participates in the membrane fusion reaction, as demonstrated by its ability to stimulate myoblast fusion and the fusion of fibroblasts to myoblasts. The inability of Myomaker alone to induce fusion of fibroblasts suggests it may require activation or additional myoblast proteins to exert its fusogenic activity, likely reflecting a requirement for close membrane apposition to allow membrane merger. Further evidence that additional myoblast proteins are required for fusion is the inventors' finding that WT myoblasts can fuse with Myomaker$^{-/-}$ myoblasts. The requirement for interactions between membrane proteins on opposite cells during myoblast fusion has been shown in zebrafish and *Drosophila* (Abmayr and Pavlath 2012 and Powell and Wright 2011), suggesting the molecular regulation of myoblast fusion differs from that of virus-cell fusion, which mainly requires the expression of a fusogenic protein (Oren-Suissa & Podbilewicz). Changes in the actin-cytoskeleton are required for cell-cell fusion (Wilson and Snell 1998 and Shilagardi et al., 2013). Consistent with this paradigm, the activity of Myomaker is abolished by cytochalasin D and latrunculin B, which disrupt cytoskeletal events required for fusion, indicating that Myomaker depends on the cytoskeleton to exert its function.

The discovery of Myomaker as a potent myoblast fusion protein opens new opportunities to dissect this fundamental cellular process at a molecular level and to understand how myoblast fusion is perturbed during muscle disease. Moreover, the ability of Myomaker to drive fusion of non-muscle cells with muscle cells represents an interesting strategy for enhancing muscle repair. These and other aspects of the disclosure are described below.

I. Myomaker

Transmembrane protein 8c (Tmem8c), designated here as Myomaker, is a poorly characterized protein of 221 residues that highly conserved across vertebrates. The gene is located on human chromosome 9q34.2. It contains 6 putative helical regions of roughly 20 amino acids distributed evenly throughout the protein. The DNA and protein sequences are provided as SEQ ID NO: 1 and 2, respectively.

II. Peptides and Polypeptides

In certain embodiments, the present disclosure may concerns Myomaker protein molecules. As used herein, a "protein" or "polypeptide" generally refers full length proteins. In contrast, a peptide is defined as being usually from about 3 to about 100 amino acids. All the "proteinaceous" terms described above may be used interchangeably herein. A human Myomaker polypeptide sequence is provided in SEQ ID NO: 2.

In certain embodiments, the proteinaceous composition comprises at least one protein, polypeptide or peptide. In further embodiments, the proteinaceous composition comprises a biocompatible protein, polypeptide or peptide. As used herein, the term "biocompatible" refers to a substance which produces no significant untoward effects when applied to, or administered to, a given organism according to the methods and amounts described herein. Such untoward or undesirable effects are those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (world-wide-webe at ncbi.nlm.nih.gov). The coding regions for these known genes may be amplified and/or expressed using the techniques disclosed herein or as would be know to those of ordinary skill in the art. Alternatively, proteins may be produced recombinantly or purified from natural sources. Shorter peptide molecules may be synthesized in solution or on a solid support in accordance with conventional techniques. Various automatic synthesizers are commercially available and can be used in accordance with known protocols. See, e.g., Stewart and Young (1984); Tam et al. (1983); Merrifield (1986); and Barany and Merrifield (1979), each incorporated herein by reference.

In certain embodiments, a proteinaceous compound may be purified. Generally, "purified" will refer to a specific or protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide.

III. Nucleic Acids

In certain embodiments of the present disclosure, nucleic acids derived from or encoding Myomaker are provided. In certain aspects, the nucleic acids may comprise wild-type or a modified version of these genes. In particular aspects, the nucleic acid encodes for or comprises a transcribed nucleic acid. In other aspects, the nucleic acid comprises a nucleic acid segment of SEQ ID NO: 1, or a biologically functional equivalent thereof. In particular aspects, the nucleic acid encodes a protein, polypeptide, or peptide.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally-occurring purine or pyrimidine base found in DNA (e.g., an adenine "A," a guanine "G," a thymine "T" or a cytosine "C") or RNA (e.g., an "A," a "G," an uracil "U" or a "C"). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single-stranded nucleic acid may be denoted by the prefix "ss," a double-stranded nucleic acid by the prefix "ds," and a triple-stranded nucleic acid by the prefix "ts."

1. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266 032, incorporated herein by reference, or via deoxynucleoside H-phosphonate intermediates as described by Froehler et al. (1986) and U.S. Pat. No. 5,705,629, each incorporated herein by reference. In the methods of the present disclosure, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

2. Purification of Nucleic Acids

A nucleic acid may be purified on polyacrylamide gels, cesium chloride centrifugation gradients, or by any other means known to one of ordinary skill in the art (see for example, Sambrook et al., 2001, incorporated herein by reference).

In certain aspect, the present disclosure concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

3. Nucleic Acid Segments

In certain embodiments, the nucleic acid is a nucleic acid segment. As used herein, the term "nucleic acid segment," are smaller fragments of a nucleic acid, such as for non-limiting example, those that encode only part of Myomaker. Thus, a "nucleic acid segment" may comprise any part of a gene sequence, of from about 10 nucleotides to the full length of Myomaker gene. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

4. Nucleic Acid Complements

The present disclosure also encompasses a nucleic acid that is complementary to a Myomaker-encoding nucleic acid. In particular embodiments the disclosure encompasses a nucleic acid or a nucleic acid segment complementary to the sequence set forth in SEQ ID NO:1. A nucleic acid is a "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule.

As used herein, the term "complementary" or "complement(s)" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range derivable therein, of the nucleobase sequence is capable of base-pairing with a single or double stranded nucleic acid molecule during hybridization. In certain embodiments, the term "complementary" refers to a nucleic acid that may hybridize to another nucleic acid strand or duplex in stringent conditions, as would be understood by one of ordinary skill in the art.

In certain embodiments, a "partly complementary" nucleic acid comprises a sequence that may hybridize in low stringency conditions to a single or double stranded nucleic acid, or contains a sequence in which less than about 70% of the nucleobase sequence is capable of base-pairing with a single or double stranded nucleic acid molecule during hybridization.

5. Expression Constructs

Within certain embodiments, expression constructs will be are employed to express Myomaker. Expression requires that appropriate signals be provided in vectors, which include various regulatory elements, such as enhancers/promoters from both viral and mammalian sources that drive expression of Myomaker in recipient cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for Myomaker in which part or all of the nucleic acid encoding sequence is capable of being transcribed. The term "vector" is used to refer to a carrier nucleic acid molecule into which a nucleic acid sequence can be inserted for introduction into a cell where it can be replicated. A nucleic acid sequence can be "exogenous," which means that it is foreign to the particular cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (2001) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally-associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally-occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (2001), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996).

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the disclosure, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

Vectors can include a multiple cloning site (MCS), which is a nucleic acid region that contains multiple restriction enzyme sites, any of which can be used in conjunction with standard recombinant technology to digest the vector. See Carbonelli et al., 1999, Levenson et al., 1998, and Cocea, 1997, incorporated herein by reference. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see Chandler et al., 1997, herein incorporated by reference.)

The vectors or constructs of the present disclosure will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the disclosure include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

In expression, particularly eukaryotic expression, one will typically include a polyadenylation signal to effect proper polyadenylation of the transcript. The nature of the polyadenylation signal is not believed to be crucial to the successful practice of the disclosure, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

In certain embodiments of the disclosure, cells containing a nucleic acid construct of the present disclosure may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

IV. Muscle Diseases

The present disclosure finds particular relevance in analyzing and treating muscle disorders. In particular, muscle disorders in which muscle cells fail to produce enough (or any) of a gene product needed for normal function, or where an aberrant protein is produce, the use of somatic cell fusion to deliver genes or proteins is highly desired. The following is a general discuss of a few disorders that could be addressed according to the present disclosure.

A. Muscular Dystrophy

Muscular Dystrophy (MD) is a group of muscle diseases that weaken the musculoskeletal system and hamper locomotion. Muscular dystrophies are characterized by progressive skeletal muscle weakness, defects in muscle proteins, and the death of muscle cells and tissue.

In the 1860s, descriptions of boys who grew progressively weaker, lost the ability to walk, and died at an early age became more prominent in medical journals. In the following decade, French neurologist Guillaume Duchenne gave a comprehensive account of thirteen boys with the most common and severe form of the disease, which now carries his name—Duchenne muscular dystrophy.

It soon became evident that the disease had more than one form. The other major forms are Becker, limb-girdle, congenital, facioscapulohumeral, myotonic, oculopharyngeal, distal, and Emery-Dreifuss muscular dystrophy. These diseases predominantly affect males, although females may be carriers of the disease gene. Most types of MD are multisystem disorders with manifestations in body systems including the heart, gastrointestinal system, nervous system, endocrine glands, eyes and brain.

Apart from the nine major types of muscular dystrophy listed above, several MD-like conditions have also been identified. Normal intellectual, behavioral, bowel and sexual function is noticed in individuals with other forms of MD and MD-like conditions. MD-affected individuals with susceptible intellectual impairment are diagnosed through molecular characteristics but not through problems associated with disability. However, a third of patients who are severely affected with DMD may have cognitive impairment, behavioral, vision and speech problems.

These conditions are generally inherited, and the different muscular dystrophies follow various inheritance patterns. However, mutations of the dystrophin gene and nutritional defects (with no genetics history) at the prenatal stage are also possible in about 33% of people affected by DMD. The main cause of the Duchenne and Becker types of muscular dystrophy is the muscle tissue's cytoskeletal impairment to properly create the functional protein dystrophin and dystrophin-associated protein complex.

Dystrophin protein is found in muscle fibre membrane; its helical nature allows it to act like a spring or shock absorber. Dystrophin links actin (cytoskeleton) and dystroglycans of the muscle cell plasma membrane, known as the sarcolemma (extracellular). In addition to mechanical stabilization, dystrophin also regulates calcium levels.

The diagnosis of muscular dystrophy is based on the results of muscle biopsy, increased creatine phosphokinase (CpK3), electromyography, electrocardiography and DNA analysis.

A physical examination and the patient's medical history will help the doctor determine the type of muscular dystrophy. Specific muscle groups are affected by different types of muscular dystrophy.

Often, there is a loss of muscle mass (wasting), which may be hard to see because some types of muscular dystrophy cause a build up of fat and connective tissue that makes the muscle appear larger. This is called pseudohypertrophy.

There is no known cure for muscular dystrophy, although significant headway is being made with antisense oligonucleotides. Physical therapy, occupational therapy, orthotic intervention (e.g., ankle-foot orthosis), speech therapy and orthopedic instruments (e.g., wheelchairs and standing frames) may be helpful. Inactivity (such as bed rest, sitting for long periods) and bodybuilding efforts to increase myofibrillar hypertrophy can worsen the disease.

There is no specific treatment for any of the forms of muscular dystrophy. Physiotherapy, aerobic exercise, low intensity anabolic steroids, prednisone supplements may help to prevent contractures and maintain muscle tone. Orthoses (orthopedic appliances used for support) and corrective orthopedic surgery may be needed to improve the quality of life in some cases. The cardiac problems that occur with Emery-Dreifuss muscular dystrophy and myotonic muscular dystrophy may require a pacemaker. The myotonia (delayed relaxation of a muscle after a strong contraction) occurring in myotonic muscular dystrophy may be treated with medications such as quinine, phenytoin, or mexiletine, but no actual long term treatment has been found.

Occupational therapy assists the individual with MD in engaging in his/her activities of daily living (self-feeding, self-care activities, etc.) and leisure activities at the most independent level possible. This may be achieved with use of adaptive equipment or the use of energy conservation techniques. Occupational therapy may implement changes to a person's environment, both at home or work, to increase the individual's function and accessibility. Occupational therapists also address psychosocial changes and cognitive decline which may accompany MD, as well as provide support and education about the disease to the family and individual.

High dietary intake of lean meat, sea food, pulses, olive oil, antioxidants; such as leafy vegetables and bell peppers, and fruits like blueberry, cherry etc. is advised. Decreased intake of refined food, trans-fats, and caffeinated and alcoholic beverages is also advised; as is a check for any food allergies.

Diagnosis, neurology, GI-nutrition, respiratory care, cardiac care, orthopedics, psychosocial, rehabilitation, and oral care form the integral part of disease management, all through the patient's life span.

The prognosis for people with muscular dystrophy varies according to the type and progression of the disorder. Some cases may be mild and progress very slowly over a normal lifespan, while others produce severe muscle weakness, functional disability, and loss of the ability to walk. Some children with muscular dystrophy die in infancy while others live into adulthood with only moderate disability. The muscles affected vary, but can be around the pelvis, shoulder, face or elsewhere. Muscular dystrophy can affect adults, but the more severe forms tend to occur in early childhood.

B. Amyotrophic Lateral Sclerosis

Amyotrophic lateral sclerosis (ALS), sometimes called Lou Gehrig's Disease, affects as many as 20,000 Americans at any given time, with 5,000 new cases being diagnosed in the United States each year. ALS affects people of all races and ethnic backgrounds. Men are about 1.5 times more likely than women to be diagnosed with the disease. ALS strikes in the prime of life, with people most commonly diagnosed between the ages of 40 and 70. However, it is possible for individuals to be diagnosed at younger and older ages. About 90-95% of ALS cases occur at random, meaning that individuals do not have a family history of the disease and other family members are not at increased risk for contracting the disease. In about 5-10% of ALS cases there is a family history of the disease.

ALS is a progressive neurological disease that attacks neurons that control voluntary muscles. Motor neurons, which are lost in ALS, are specialized nerve cells located in the brain, brainstem, and spinal cord. These neurons serve as connections from the nervous system to the muscles in the body, and their function is necessary for normal muscle movement. ALS causes motor neurons in both the brain and spinal cord to degenerate, and thus lose the ability to initiate and send messages to the muscles in the body. When the muscles become unable to function, they gradually atrophy and twitch. ALS can begin with very subtle symptoms such as weakness in affected muscles. Where this weakness first appears differs for different people, but the weakness and atrophy spread to other parts of the body as the disease progresses.

Initial symptoms may affect only one leg or arm, causing awkwardness and stumbling when walking or running. Subjects also may suffer difficulty lifting objects or with tasks that require manual dexterity. Eventually, the individual will not be able to stand or walk or use hands and arms to perform activities of daily living. In later stages of the disease, when the muscles in the diaphragm and chest wall become too weak, patients require a ventilator to breathe. Most people with ALS die from respiratory failure, usually 3 to 5 years after being diagnosed; however, some people survive 10 or more years after diagnosis.

Perhaps the most tragic irony of ALS is that it does not impair a person's mind, as the disease affects only the motor neurons. Personality, intelligence, memory, and self-awareness are not affected, nor are the senses of sight, smell, touch, hearing, and taste. Yet at the same time, ALS causes dramatic defects in an individual's ability to speak loudly and clearly, and eventually, completely prevents speaking and vocalizing. Early speech-related symptoms include nasal speech quality, difficulty pronouncing words, and difficulty with conversation. As muscles for breathing weaken, it becomes difficult for patients to speak loud enough to be understood and, eventually, extensive muscle atrophy eliminates the ability to speak altogether. Patients also experience difficulty chewing and swallowing, which increase over time to the point that a feeding tube is required.

C. Pompe Disease

Glycogen storage disease type II (also called Pompe disease or acid maltase deficiency) is an autosomal recessive metabolic disorder which damages muscle and nerve cells throughout the body. It is caused by an accumulation of glycogen in the lysosome due to deficiency of the lysosomal acid alpha-glucosidase enzyme. It is the only glycogen storage disease with a defect in lysosomal metabolism, and the first glycogen storage disease to be identified, in 1932 by the Dutch pathologist J. C. Pompe. The build-up of glycogen causes progressive muscle weakness (myopathy) throughout the body and affects various body tissues, particularly in the heart, skeletal muscles, liver and nervous system.

There are exceptions, but levels of alpha-glucosidase determines the type of GSD II an individual may have. More alpha glucosidase present in the individuals muscles means symptoms occur later in life and progress more slowly. GSD II is broadly divided into two onset forms based on the age symptoms occur. Infantile-onset form is usually diagnosed at 4-8 months; muscles appear normal but are limp and weak preventing them from lifting their head or rolling over. As the disease progresses heart muscles thicken and progressively fail. Without treatment death usually occurs due to heart failure and respiratory weakness. Late/later onset form occurs later than one to two years and progresses more slowly than Infantile-onset form. One of the first symptoms is a progressive decrease in muscle strength starting with the legs and moving to smaller muscles in the trunk and arms, such as the diaphragm and other muscles required for breathing. Respiratory failure is the most common cause of death. Enlargement of the heart muscles and rhythm disturbances are not significant features but do occur in some cases.

The infantile form usually comes to medical attention within the first few months of life. The usual presenting features are cardiomegaly (92%), hypotonia (88%), cardiomyopathy (88%), respiratory distress (78%), muscle weakness (63%), feeding difficulties (57%) and failure to thrive (53%). The main clinical findings include floppy baby appearance, delayed motor milestones and feeding difficulties. Moderate hepatomegaly may be present. Facial features include macroglossia, open mouth, wide open eyes, nasal flaring (due to respiratory distress), and poor facial muscle tone. Cardiopulmonary involvement is manifest by increased respiratory rate, use of accessory muscles for respiration, recurrent chest infections, decreased air entry in the left lower zone (due to cardiomegaly), arrhythmias and evidence of heart failure. Median age at death in untreated cases is 8.7 months and is usually due to cardiorespiratory failure.

This form differs from the infantile principally in the relative lack of cardiac involvement. The onset is more insidious and has a slower progression. Cardiac involvement may occur but is milder than in the infantile form. Skeletal involvement is more prominent with a predilection for the lower limbs. Late onset features include impaired cough, recurrent chest infections, hypotonia, progressive muscle weakness, delayed motor milestones, difficulty swallowing or chewing and reduced vital capacity. Prognosis depends on the age of onset on symptoms with a better prognosis being associated with later onset disease.

Diagnostic procedures include chest X ray, electrocardiogram and echocardiography. Typical findings are those of an enlarged heart with non specific conduction defects. Biochemical investigations include serum creatine kinase (typically increased 10 fold) with lesser elevations of the serum aldolase, aspartate transaminase, alanine transaminase and lactic dehydrogenase. Diagnosis is made by estimating the acid alpha glucosidase activity in either skin biopsy (fibroblasts), muscle biopsy (muscle cells) or in white blood cells. The choice of sample depends on the facilities available at the diagnostic laboratory. In the late onset form, the findings on investigation are similar to those of the infantile form with the caveat that the creatinine kinases may be normal in some cases. The diagnosis is by estimation of the enzyme activity in a suitable sample.

The disease is caused by a mutation in a gene (acid alpha-glucosidase: also known as acid maltase) on long arm of chromosome 17 at 17q25.2-q25.3 (base pair 75,689,876 to 75,708,272). The number of mutations described is currently (in 2010) 289 with 67 being non-pathogenic mutations and 197 pathogenic mutations. The remainder are still being evaluated for their association with disease. The gene spans approximately 20 kb and contains 20 exons with the first exon being noncoding. The coding sequence of the putative catalytic site domain is interrupted in the middle by an intron of 101 bp. The promoter has features characteristic of a 'housekeeping' gene. The GC content is high (80%) and distinct TATA and CCAAT motifs are lacking.

Most cases appear to be due to three mutations. A transversion (T→G) mutation is the most common among adults with this disorder. This mutation interrupts a site of RNA splicing. The gene encodes a protein—acid alpha-glucosidase—which is a lysosomal hydrolase. The protein is an enzyme that normally degrades the alpha-1,4 and alpha-1,6 linkages in glycogen, maltose and isomaltose and is required for the degradation of 1-3% of cellular glycogen. The deficiency of this enzyme results in the accumulation of structurally normal glycogen in lysosomes and cytoplasm in affected individuals. Excessive glycogen storage within lysosomes may interrupt normal functioning of other organelles and lead to cellular injury.

Cardiac and respiratory complications are treated symptomatically. Physical and occupational therapy may be beneficial for some patients. Alterations in diet may provide temporary improvement but will not alter the course of the disease. Genetic counseling can provide families with information regarding risk in future pregnancies.

On Apr. 28, 2006 the US Food and Drug Administration approved a Biologic License Application (BLA) for Myozyme (alglucosidase alfa, rhGAA), the first treatment for patients with Pompe disease, developed by a team of Duke University researchers. This was based on enzyme replacement therapy using biologically active recombinant human alglucosidase alfa produced in Chinese Hamster Ovary cells. Myozyme falls under the FDA Orphan Drug designation and was approved under a priority review. The FDA has approved Myozyme for administration by intravenous infusion of the solution. The safety and efficacy of Myozyme were assessed in two separate clinical trials in 39 infantile-onset patients with Pompe disease ranging in age from 1 month to 3.5 years at the time of the first infusion. Myozyme treatment clearly prolongs ventilator-free survival and overall survival. Early diagnosis and early treatment leads to much better outcomes. The treatment is not without side effects which include fever, flushing, skin rash, increased heart rate and even shock; these conditions, however, are usually manageable.

A new treatment option for this disease is called Lumizyme. Lumizyme and Myozyme have the same generic ingredient (Alglucosidase Alfa) and manufacturer (Genzyme Corporation). The difference between these two products is in the manufacturing process. Today, the Myozyme is made using a 160-L bioreactor, while the Lumizyme uses a 4000-L bioreactor. Because of the difference in the manufacturing process, the FDA claims that the two products are biologically different. Moreover, Lumizyme is FDA approved as replacement therapy for late-onset (noninfantile) Pompe disease without evidence of cardiac hypertrophy in patients 8 years and older. Myozyme is FDA approved for replacement therapy for infantile-onset Pompe disease. The prognosis for individuals with Pompe disease varies according to the onset and severity of symptoms. Without treatment the disease is particularly lethal in infants and young children.

Myozyme (alglucosidase alfa), which helps break down glucose, is a recombinant form of the human enzyme acid alpha-glucosidase, and is also currently being used to replace the missing enzyme. In a study which included the largest cohort of patients with Pompe disease treated with enzyme replacement therapy (ERT) to date findings showed that Myozyme treatment clearly prolongs ventilator-free survival and overall survival in patients with infantile-onset Pompe disease as compared to an untreated historical control population. Furthermore, the study demonstrated that initiation of ERT prior to 6 months of age, which could be facilitated by newborn screening, shows great promise to reduce the mortality and disability associated with this devastating disorder. Taiwan and several states in the United States have started the newborn screening and results of such regimen in early diagnosis and early initiation of the therapy have dramatically improved the outcome of the disease; many of these babies have reached the normal motor developmental milestones.

Another factor affecting the treatment response is generation of antibodies against the infused enzyme, which is particularly severe in Pompe infants who have complete deficiency of the acid alpha-glucosidase. Immune tolerance therapy to eliminate these antibodies has improved the treatment outcome.

A Late Onset Treatment Study (LOTS) was published in 2010. The study was undertaken to evaluate the safety and efficacy of aglucosidase alfa in juvenile and adult patients with Pompe disease. LOTS was a randomized, double-blind, placebo-controlled study that enrolled 90 patients at eight primary sites in the United States and Europe. Participants received either aglucosidase alfa or a placebo every other week for 18 months. The average age of study participants was 44 years. The results showed that, at 78 weeks, patients treated with aglucosidase alfa increased their distance walked in six minutes by an average of approximately 25 meters as compared with the placebo group which declined by 3 meters (P=0.03). The placebo group did not show any improvement from baseline. The average baseline distance walked in six minutes in both groups was approximately 325 meters. Percent predicted forced vital capacity in the group of patients treated with aglucosidase alfa increased by 1.2 percent at 78 weeks. In contrast, it declined by approximately 2.2 percent in the placebo group (P=0.006).

D. Rhabdomyosarcoma

A rhabdomyosarcoma, commonly referred to as RMS, is a type of cancer, specifically a sarcoma (cancer of connective tissues), in which the cancer cells are thought to arise from skeletal muscle progenitors. It can also be found attached to muscle tissue, wrapped around intestines, or in any anatomic location. Most occur in areas naturally lacking in skeletal muscle, such as the head, neck, and genitourinary tract.

Its two most common forms are embryonal rhabdomyosarcoma and alveolar rhabdomyosarcoma. In the former, which is more common in younger children, the cancer cells resemble those of a typical 6-to-8-week embryo. In the latter, which is more common in older children and teenagers, they resemble those of a typical 10-to-12-week embryo.

Rhabdomyosarcoma is a relatively rare form of cancer. It is most common in children ages one to five, and is also found in teens aged 15 to 19, although this is more rare. This cancer is also an adult cancer but it is rare. St. Jude Children's Research Hospital reports that rhabdomyosarcoma is the most common soft tissue sarcoma in children. Soft tissue sarcomas make up about 3% of childhood cancers.

The diagnosis of rhabdomyosarcoma is made by a pathologist, he or she will examine a biopsy of the tumor under the microscope and arrive at the diagnosis of rhabdomyosarcoma based on the morphology (appearance) of the tumor cells and the results of immunohistochemical stains. Diagnosis of rhabdomyosarcoma depends on recognition of differentiation toward skeletal muscle cells. The proteins myoD1 and myogenin are transcription factor proteins normally found in developing skeletal muscle cells which disappears after the muscle matures and becomes innervated by a nerve. Thus, myoD1 and myogenin are not usually found in normal skeletal muscle and serve as a useful immunohistochemical marker of rhabdomyosarcoma. Early manifestation can be misdiagnosed as a pseudotumor that is non responsive to steroid treatment.

Photomicrograph showing nodules of tumor cells separated by hyalinised fibrous septae (50×, HE stain). Inset: Discohesive large tumor cells with hyperchromatic nucleus and scant cytoplasm (200×, HE stain). The diagnosis was postauricular congenital alveolar rhabdomyosarcoma. Several different histological subtypes of rhabdomyosarcoma exist, each of which has different clinical and pathological characteristics. Prognosis and clinical behavior of the tumor is also partially dependent on histologic subtype. Multiple classification systems have been proposed for subclassifying these tumors. The most recent classification system, the "International Classification of Rhabdomyosarcoma," was created by the Intergroup Rhabdomyosarcoma Study. This system attempts to combined elements of the previous systems and correlate these with prognosis based on tumor type.

Several additional subtypes of rhabdomyosarcoma exist that do not fit into the International Classification scheme. Pleomorphic rhabdomyosarcoma usually occurs in adults rather than children, and, thus, is not included in this system. Sclerosing rhabdomyosarcoma is a rare rhabdomyosarcoma subtype recently characterized by Folpe, et al.; it is not included in this system. Although botryoid and spindle cell rhabdomyosarcoma are classically considered as subtypes of embryonal rhabdomyosarcoma, they have more favorable clinical behavior and prognosis than classic embryonal rhabdomyosarcoma.

Treatment for rhabdomyosarcoma consists of chemotherapy, radiation therapy and sometimes surgery. Surgery to remove the tumor may be difficult or impossible depending on the location of the tumor. If there is no evidence of metastasis, surgery combined with chemotherapy and radiation offers the best prognosis. Patients whose tumors have not metastasized usually have a good chance for long-term survival, depending on the subtype of the tumor. St Jude's Children's Research Hospital reports that more than 70% of children diagnosed with localized rhabdomyosarcoma have long-term survival.

E. Sarcopenia

Sarcopenia (from the Greek meaning "poverty of flesh") is the degenerative loss of skeletal muscle mass (0.5-1% loss per year after the age of 25), quality, and strength associated with aging. Sarcopenia is a component of the frailty syndrome. As of 2009, there was no generally accepted definition of sarcopenia in the medical literature.

Sarcopenia is characterized first by a muscle atrophy (a decrease in the size of the muscle), along with a reduction in muscle tissue "quality," caused by such factors as replacement of muscle fibres with fat, an increase in fibrosis, changes in muscle metabolism, oxidative stress, and degeneration of the neuromuscular junction. Combined, these changes lead to progressive loss of muscle function and frailty.

Lack of exercise is currently thought to be a significant risk factor for sarcopenia. Not only muscle but the entire musculoskeletal system of muscle, neuromuscular responsiveness, endocrine function, vasocapillary access, tendon, joint, ligament, and bone, depends on regular and lifelong exercise to maintain integrity. Exercise and increases in activity have been shown to be beneficial in settings of sarcopenia, even in the very old. However, even highly trained athletes experience the effects of sarcopenia. Even Master class athletes who continue to train and compete throughout their adult life, exhibit a progressive loss of muscle mass and strength, and records in speed and strength events decline progressively after age 30.

Simple circumference measurement does not provide enough data to determine whether or not an individual is suffering from severe sarcopenia. Sarcopenia is also marked by a decrease in the circumference of distinct types of muscle fibers. Skeletal muscle has different fiber-types, which are characterized by expression of distinct myosin variants. During sarcopenia, there is a decrease in "type 2" fiber circumference (Type II), with little to no decrease in "type I" fiber circumference (Type I), and deinervated type 2 fibers are often converted to type 1 fibers by reinnervation by slow type 1 fiber motor nerves.

Satellite cells are small mononuclear cells that abut the muscle fiber. Satellite cells are normally activated upon injury or exercise. These cells then differentiate and fuse into the muscle fiber, helping to maintain its function. One theory is that sarcopenia is in part caused by a failure in satellite cell activation. Therefore, the ability to repair damaged muscles or respond to nutritional signals is impaired.

Extreme muscle loss is often a result of both diminishing anabolic signals, such as growth hormone and testosterone, and promotion of catabolic signals, such as pro-inflammatory cytokines.

Due to the lessened physical activity and increased longevity of industrialized populations, sarcopenia is emerging as a major health concern. Sarcopenia may progress to the extent that an older person may lose his or her ability to live independently. Furthermore, sarcopenia is an important independent predictor of disability in population-based studies, linked to poor balance, gait speed, falls, and fractures. Sarcopenia can be thought of as a muscular analog of osteoporosis, which is loss of bone, also caused by inactivity and counteracted by exercise. The combination of osteoporosis and sarcopenia results in the significant frailty often seen in the elderly population.

Exercise has been considered of great interest in treatment of sarcopenia. There are several reports showing increased ability and capacity of skeletal muscle to synthesize proteins in response to short term resistance exercise. Also, it has been reported exercise can improve physical performance (strength and mobility) in elderly subjects. However, there is insufficient research demonstrating such findings in long term.

Currently, there are no agents approved for treatment of sarcopenia. Possible therapeutic strategies include use of testosterone or anabolic steroids, though long term use of these agents is controversial in men given concerns of prostate symptoms, and essentially contraindicated in women, given concerns of virilization. Recent experimental results have shown testosterone treatments may induce adverse cardiovascular events. Other approved medications have been shown to have little to no effect in this setting, including agents such DHEA and human growth hormone. New therapies in clinical development hold great promise in this area, including the selective androgen receptor modulators (SARMs), as evidenced by recent studies. Nonsteriodal SARMs are of particular interest, given they exhibit significant selectivity between the anabolic effects of testosterone on muscle, but apparently with little to no androgenic effects such as prostate stimulation in men or virilization in women.

V. Gene Transfer

In accordance with the present disclosure, non-muscle cells will be subject to gene transfer of the Myomaker gene. Gene transfer methods generally fall into two general categories: viral and non-viral. The suitability of these methods will be determined by the particular constraints of the subject matter, such as the size and structure of the genes being transferred, and the type of cell into which the genetic material is to be delivered. Those of skill in the art can make appropriate selections from the myriad of different systems that are commonly used, many of which commercially available. The following is a general discussion of both types of methods.

A. Viral Transformation

The capacity of certain viral vectors to efficiently infect or enter cells, to integrate into a host cell genome and stably express viral genes, have led to the development and application of a number of different viral vector systems (Robbins et al., 1998). Viral systems are currently being developed for use as vectors for ex vivo and in vivo gene transfer. For example, adenovirus, herpes-simplex virus, retrovirus and adeno-associated virus vectors are being evaluated currently for treatment of diseases such as cancer, cystic fibrosis, Gaucher disease, renal disease and arthritis (Robbins and Ghivizzani, 1998; Imai et al., 1998; U.S. Pat. No. 5,670,488). The various viral vectors described below, present specific advantages and disadvantages, depending on the particular gene-therapeutic application.

Adenoviral Vectors.

Adenoviruses comprise linear, double-stranded DNA, with a genome ranging from 30 to 35 kb in size (Reddy et al., 1998; Morrison et al., 1997; Chillon et al., 1999). An adenovirus expression vector according to the present disclosure comprises a genetically engineered form of the adenovirus. Advantages of adenoviral gene transfer include the ability to infect a wide variety of cell types, including non-dividing cells, a mid-sized genome, ease of manipulation, high infectivity and the ability to be grown to high titers (Wilson, 1996). Further, adenoviral infection of host cells does not result in chromosomal integration because adenoviral DNA can replicate in an episomal manner, without potential genotoxicity associated with other viral vectors. Adenoviruses also are structurally stable (Marienfeld et al., 1999) and no genome rearrangement has been detected after extensive amplification (Parks et al., 1997; Bett et al., 1993).

Salient features of the adenovirus genome are an early region (E1, E2, E3 and E4 genes), an intermediate region (pIX gene, Iva2 gene), a late region (L1, L2, L3, L4 and L5 genes), a major late promoter (MLP), inverted-terminal-repeats (ITRs) and a ψ sequence (Zheng, et al., 1999; Robbins et al., 1998; Graham and Prevec, 1995). The early genes E1, E2, E3 and E4 are expressed from the virus after infection and encode polypeptides that regulate viral gene expression, cellular gene expression, viral replication, and inhibition of cellular apoptosis. Further on during viral infection, the MLP is activated, resulting in the expression of the late (L) genes, encoding polypeptides required for adenovirus encapsidation. The intermediate region encodes components of the adenoviral capsid. Adenoviral inverted terminal repeats (ITRs; 100-200 bp in length), are cis elements, and function as origins of replication and are necessary for viral DNA replication. The gy sequence is required for the packaging of the adenoviral genome.

A common approach for generating an adenoviruses for use as a gene transfer vector is the deletion of the E1 gene (E1⁻), which is involved in the induction of the E2, E3 and E4 promoters (Graham and Prevec, 1995). Subsequently, a therapeutic gene or genes can be inserted recombinantly in place of the E1 gene, wherein expression of the therapeutic gene(s) is driven by the E1 promoter or a heterologous promoter. The E1⁻, replication-deficient virus is then proliferated in a "helper" cell line that provides the E1 polypeptides in trans (e.g., the human embryonic kidney cell line 293). Thus, in the present disclosure it may be convenient to introduce the transforming construct at the position from which the E1-coding sequences have been removed. However, the position of insertion of the construct within the adenovirus sequences is not critical to the disclosure. Alternatively, the E3 region, portions of the E4 region or both may be deleted, wherein a heterologous nucleic acid sequence under the control of a promoter operable in eukaryotic cells is inserted into the adenovirus genome for use in gene transfer (U.S. Pat. Nos. 5,670,488; 5,932,210, each specifically incorporated herein by reference).

Retroviral Vectors.

In certain embodiments of the disclosure, the use of retroviruses for gene delivery are contemplated. Retroviruses are RNA viruses comprising an RNA genome. When a host cell is infected by a retrovirus, the genomic RNA is reverse transcribed into a DNA intermediate which is integrated into the chromosomal DNA of infected cells. This integrated DNA intermediate is referred to as a provirus. A particular advantage of retroviruses is that they can stably infect dividing cells with a gene of interest (e.g., a therapeutic gene) by integrating into the host DNA, without expressing immunogenic viral proteins. Theoretically, the integrated retroviral vector will be maintained for the life of the infected host cell, expressing the gene of interest.

The retroviral genome and the proviral DNA have three genes: gag, pol, and env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication.

A recombinant retrovirus of the present disclosure may be genetically modified in such a way that some of the structural, infectious genes of the native virus have been removed and replaced instead with a nucleic acid sequence to be delivered to a target cell (U.S. Pat. Nos. 5,858,744; 5,739,018, each incorporated herein by reference). After infection of a cell by the virus, the virus injects its nucleic acid into the cell and the retrovirus genetic material can integrate into the host cell genome. The transferred retrovirus genetic material is then transcribed and translated into proteins within the host cell. As with other viral vector systems, the generation of a replication-competent retrovirus during vector production or during therapy is a major concern. Retroviral vectors suitable for use in the present disclosure are generally defective retroviral vectors that are capable of infecting the target cell, reverse transcribing their RNA genomes, and integrating the reverse transcribed DNA into the target cell genome, but are incapable of replicating within the target cell to produce infectious retroviral particles (e.g., the retroviral genome transferred into the target cell is defective in gag, the gene encoding virion structural proteins, and/or in pol, the gene encoding reverse transcriptase). Thus, transcription of the provirus and assembly into infectious virus occurs in the presence of an appropriate helper virus or in a cell line containing appropriate sequences enabling encapsidation without coincident production of a contaminating helper virus.

Herpesviral Vectors.

Herpes simplex virus (HSV) type I and type II contain a double-stranded, linear DNA genome of approximately 150 kb, encoding 70-80 genes. Wild type HSV are able to infect cells lytically and to establish latency in certain cell types (e.g., neurons). Similar to adenovirus, HSV also can infect a variety of cell types including muscle (Yeung et al., 1999), ear (Derby et al., 1999), eye (Kaufman et al., 1999), tumors (Yoon et al., 1999; Howard et al., 1999), lung (Kohut et al., 1998), neuronal (Garrido et al., 1999; Lachmann and Efstathiou, 1999), liver (Miytake et al., 1999; Kooby et al., 1999) and pancreatic islets (Rabinovitch et al., 1999).

HSV viral genes are transcribed by cellular RNA polymerase II and are temporally regulated, resulting in the transcription and subsequent synthesis of gene products in roughly three discernable phases or kinetic classes. These phases of genes are referred to as the Immediate Early (IE) or alpha genes, Early (E) or beta genes and Late (L) or gamma genes. Immediately following the arrival of the genome of a virus in the nucleus of a newly infected cell, the IE genes are transcribed. The efficient expression of these genes does not require prior viral protein synthesis. The products of IE genes are required to activate transcription and regulate the remainder of the viral genome.

For use in therapeutic gene delivery, HSV must be rendered replication-defective. Protocols for generating replication-defective HSV helper virus-free cell lines have been described (U.S. Pat. Nos. 5,879,934; 5,851,826, each specifically incorporated herein by reference in its entirety). One IE protein, Infected Cell Polypeptide 4 (ICP4), also known as alpha 4 or Vmw175, is absolutely required for both virus infectivity and the transition from IE to later transcription. Thus, due to its complex, multifunctional nature and central role in the regulation of HSV gene expression, ICP4 has typically been the target of HSV genetic studies.

Phenotypic studies of HSV viruses deleted of ICP4 indicate that such viruses will be potentially useful for gene transfer purposes (Krisky et al., 1998a). One property of viruses deleted for ICP4 that makes them desirable for gene transfer is that they only express the five other IE genes: ICP0, ICP6, ICP27, ICP22 and ICP47 (DeLuca et al., 1985), without the expression of viral genes encoding proteins that direct viral DNA synthesis, as well as the structural proteins of the virus. This property is desirable for minimizing possible deleterious effects on host cell metabolism or an immune response following gene transfer. Further deletion of IE genes ICP22 and ICP27, in addition to ICP4, substantially improve reduction of HSV cytotoxicity and prevented early and late viral gene expression (Krisky et al., 1998b).

The therapeutic potential of HSV in gene transfer has been demonstrated in various in vitro model systems and in vivo for diseases such as Parkinson's (Yamada et al., 1999), retinoblastoma (Hayashi et al., 1999), intracerebral and intradermal tumors (Moriuchi et al., 1998), B-cell malignancies (Suzuki et al., 1998), ovarian cancer (Wang et al., 1998) and Duchenne muscular dystrophy (Huard et al., 1997).

Adeno-Associated Viral Vectors.

Adeno-associated virus (AAV), a member of the parvovirus family, is a human virus that is increasingly being used for gene delivery therapeutics. AAV has several advantageous features not found in other viral systems. First, AAV can infect a wide range of host cells, including non-dividing cells. Second, AAV can infect cells from different species. Third, AAV has not been associated with any human or animal disease and does not appear to alter the biological properties of the host cell upon integration. For example, it is estimated that 80-85% of the human population has been exposed to AAV. Finally, AAV is stable at a wide range of physical and chemical conditions which lends itself to production, storage and transportation requirements.

The AAV genome is a linear, single-stranded DNA molecule containing 4681 nucleotides. The AAV genome generally comprises an internal non-repeating genome flanked on each end by inverted terminal repeats (ITRs) of approximately 145 bp in length. The ITRs have multiple functions, including origins of DNA replication, and as packaging signals for the viral genome. The internal non-repeated portion of the genome includes two large open reading frames, known as the AAV replication (rep) and capsid (cap) genes. The rep and cap genes code for viral proteins that allow the virus to replicate and package the viral genome into a virion. A family of at least four viral proteins are expressed from the AAV rep region, Rep 78, Rep 68, Rep 52, and Rep 40, named according to their apparent molecular weight. The AAV cap region encodes at least three proteins, VP1, VP2, and VP3.

AAV is a helper-dependent virus requiring co-infection with a helper virus (e.g., adenovirus, herpesvirus or vaccinia) in order to form AAV virions. In the absence of co-infection with a helper virus, AAV establishes a latent state in which the viral genome inserts into a host cell chromosome, but infectious virions are not produced. Subsequent infection by a helper virus "rescues" the integrated genome, allowing it to replicate and package its genome into infectious AAV virions. Although AAV can infect cells from different species, the helper virus must be of the same species as the host cell (e.g., human AAV will replicate in canine cells co-infected with a canine adenovirus).

AAV has been engineered to deliver genes of interest by deleting the internal non-repeating portion of the AAV genome and inserting a heterologous gene between the ITRs. The heterologous gene may be functionally linked to a heterologous promoter (constitutive, cell-specific, or inducible) capable of driving gene expression in target cells. To produce infectious recombinant AAV (rAAV) containing a heterologous gene, a suitable producer cell line is transfected with a rAAV vector containing a heterologous gene. The producer cell is concurrently transfected with a second plasmid harboring the AAV rep and cap genes under the control of their respective endogenous promoters or heterologous promoters. Finally, the producer cell is infected with a helper virus.

Lentiviral Vectors.

Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif vpr, vpu and nefare deleted making the vector biologically safe.

Recombinant lentiviral vectors are capable of infecting non-dividing cells and can be used for both in vivo and ex vivo gene transfer and expression of nucleic acid sequences. The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx.

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

Lentiviral vectors are known in the art; see Naldini et al., (1996); Zufferey et al., (1997); U.S. Pat. Nos. 6,013,516; and 5,994,136. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest.

Other Viral Vectors.

The development and utility of viral vectors for gene delivery is constantly improving and evolving. Other viral vectors such as poxvirus; e.g., vaccinia virus (Gnant et al., 1999; Gnant et al., 1999), alpha virus; e.g., sindbis virus, Semliki forest virus (Lundstrom, 1999), reovirus (Coffey et al., 1998) and influenza A virus (Neumann et al., 1999) are contemplated for use in the present disclosure and may be selected according to the requisite properties of the target system.

Chimeric Viral Vectors.

Chimeric or hybrid viral vectors are being developed for use in therapeutic gene delivery and are contemplated for use in the present disclosure. Chimeric poxviral/retroviral vectors (Holzer et al., 1999), adenoviral/retroviral vectors (Feng et al., 1997; Bilbao et al., 1997; Caplen et al., 2000) and adenoviral/adeno-associated viral vectors (Fisher et al., 1996; U.S. Pat. No. 5,871,982) have been described.

These "chimeric" viral gene transfer systems can exploit the favorable features of two or more parent viral species. For example, Wilson et al., provide a chimeric vector construct which comprises a portion of an adenovirus, AAV 5' and 3' ITR sequences and a selected transgene, described below (U.S. Pat. No. 5,871,983, specifically incorporate herein by reference).

B. Non-Viral Transformation

Suitable methods for nucleic acid delivery for transformation of cells or tissues for use with the current disclosure are believed to include virtually any method by which a nucleic acid (e.g., DNA) can be introduced, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

Injection:

In certain embodiments, a nucleic acid may be delivered to an organelle, a cell, a tissue or an organism via one or more injections (i.e., a needle injection), such as, for example, either subcutaneously, intradermally, intramuscularly, intervenously or intraperitoneally. Methods of injection of vaccines are well known to those of ordinary skill in the art (e.g., injection of a composition comprising a saline solution). Further embodiments of the present disclosure include the introduction of a nucleic acid by direct microinjection. Direct microinjection has been used to introduce nucleic acid constructs into *Xenopus* oocytes (Harland and Weintraub, 1985).

Electroporation.

In certain embodiments of the present disclosure, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 9217598, incorporated herein by reference. Other examples of species for which protoplast transformation has been described include barley (Lazerri, 1995), sorghum (Battraw and Hall, 1991), maize (Bhattacharjee et al., 1997), wheat (He et al., 1994) and tomato (Tsukada, 1989).

Calcium Phosphate.

In other embodiments of the present disclosure, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

DEAE-Dextran: In another embodiment, a nucleic acid is delivered into a cell using DEAE-dextran followed by polyethylene glycol. In this manner, reporter plasmids were introduced into mouse myeloma and erythroleukemia cells (Gopal, 1985).

Sonication Loading.

Additional embodiments of the present disclosure include the introduction of a nucleic acid by direct sonic loading.

LTK⁻ fibroblasts have been transfected with the thymidine kinase gene by sonication loading (Fechheimer et al., 1987).

Liposome-Mediated Transfection.

In a further embodiment of the disclosure, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the disclosure, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

Receptor Mediated Transfection:

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present disclosure.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present disclosure, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present disclosure can be specifically delivered into a target cell in a similar manner.

C. Recipient Cells

Non-muscle recipient cells may be of virtually any cell type, but in particular may be fibroblasts (abundant in skin, hair, etc.) or red blood cells (ideal as circulating and contact with muscle). Also contemplated are cells of the bone marrow and adipose stem cells, as these cells are also highly abundant. Additionally, one could use muscle precursor cells as they are the "normal" cell type that fuses to muscle.

VI. Therapeutic Treatments

The present disclosure contemplates the treatment of muscles disease using using non-muscle cells expressing Myomaker to deliver therapeutic genes to muscle tissues. This is the first time, to the inventors' knowledge, that the technology to drive muscle-specific cell fusion using non-muscle cell carriers has been available.

In certain embodiments, it is envisioned that non-muscle cells expressing Myomaker and a therapeutic gene will be delivered to or near sites in subjects where muscle cells and/or tissues are lacking one or more gene products, leading to a disease phenotype. Alternatively, cells may be fused ex vivo, either using a histocompatible cell source or cells from a patient, and subsequently injected into, local to or regional to a disease site. In both instances, the fusion of non-muscle cells with muscle cells will deliver a therapeutic gene, and hence its gene product, to muscle cells lacking that gene product, thereby reversing or reducing the disease phenotype. One could also administer these transformed cells systemically. For instance, one could collect bone marrow cells and force expression of Myomaker and the therapeutic gene, and then transplant these cells into the patient (i.e., a bone marrow transplant).

A. Combination Therapies

The cells of the present disclosure may also be used in combination with one or more other "standard" therapies. When given in combination, these compositions one would generally be administered in a combined amount effective to achieve a reduction in one or more disease parameter. This process may involve contacting the subject with the both agents/therapies at the same time, e.g., using a single composition or pharmacological formulation that includes both agents, or by contacting the subject with two distinct compositions or formulations, at the same time. Alternatively, one treatment may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations. It also is conceivable that more than one administration of either therapy will be desired.

B. Pharmaceutical Compositions and Administration

Where therapeutic applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells, as well as for culturing cells for fusions. Buffers also will be employed when recombinant cells are introduced into a patient. Aqueous compositions of the present disclosure comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intraperitoneal, or intravenous injection. Intramuscular injection will be preferred. Such compositions would normally be administered as pharmaceutically acceptable compositions.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present disclosure may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15$^{th}$ Ed., 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VIII. Kits

For use in the applications described herein, kits are also within the scope of the disclosure. Such kits can comprise a carrier, package or container that is compartmentalized to receive one or more containers such as vials, tubes, and the like, each of the container(s) comprising one of the separate elements to be used in the method, in particular, a Myomaker expression construct or a transformed cell comprising the same. The kit of the disclosure will typically comprise the container described above and one or more other containers comprising materials desirable from a commercial end user standpoint, including buffers, diluents, filters, needles, syringes, and package inserts with instructions for use. In addition, a label can be provided on the container to indicate that the composition is used for a specific therapeutic application, and can also indicate directions for either in vivo or in vitro use, such as those described above. Directions and or other information can also be included on an insert which is included with the kit.

IX. Examples

The following examples are included to further illustrate various aspects of the disclosure. It should be appreciated by those of skill in the art that the techniques disclosed in the examples which follow represent techniques and/or compositions discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Methods

Generation of Myomaker−/− Mice.

The Myomaker mouse strain used for this research project was created from ES cell Tmem8c clone (EPD0626_5_C12) obtained from KOMP Repository (world-wide-web at KOMP.org) and generated by the Wellcome Trust Sanger Institute[29]. This clone was injected into 3.5-day-old C57BL/6 blastocysts by the Transgenic Core Facility at University of Texas Southwestern Medical Center. High-percentage chimeric male mice were bred to C57BL/6 females to achieve germline transmission of the targeted allele. Myomaker+/− mice were intercrossed to generate Myomaker−/− mice. All experimental procedures involving animals in this study were reviewed and approved by the University of Texas Southwestern Medical Center's Institutional Animal Care and Use Committee.

Quantitative Real-Time PCR (qPCR).

Total RNA was extracted from either mouse tissue or cultured cells with TRIZOL® (Invitrogen) and cDNA synthesized using Superscript III reverse transcriptase with random hexamer primers (Invitrogen). Gene expression was assessed using standard qPCR approaches with either Power Sybr Green or Taqman Master Mix (Applied Biosystems). Analysis was performed on a 7900HT Fast Real-Time PCR Machine (Applied Biosystems) with the following Sybr primers:

Myomaker-F:
(SEQ ID NO: 5)
5'-ATCGCTACCAAGAGGCGTT-3'

Myomaker-R:
(SEQ ID NO: 6)
5'-CACAGCACAGACAAACCAGG-3'

Taqman probes for Myogenin, MyoD, Ckm, and Myh4 were purchased from Applied Biosystems. Expression levels were normalized to 18S and represented as-fold change.

In Situ Hybridizations.

For whole mount in situ hybridization, embryos were fixed overnight in 4% PFA/PBS at 4° C., then dehydrated in increasing concentrations of methanol and bleached with 6% $H_2O_2$/methanol for 1 hour. Embryos were subsequently rehydrated, treated with proteinase K, and fixed in 4% PFA, 0.2% glutaraldehyde for 20 min. Prehybridization (50% Formamide, 5×SSC pH 4.5, 2% SDS, 2% blocking reagent (Roche), 250 µg/ml tRNA, 100 µg/ml heparin) was achieved at 70° C. for 1 hour followed by incubation with digoxigenin-labeled probe overnight. Embryos were first washed with Solution 1 (50% Formamide, 2×SSC pH 4.5, and 1% SDS) three times, 6 times in Solution 2 (100 mM Maleic Acid, 150 mM NaCl, 0.1% Tween-20, pH 7.5), then blocked with consecutive 1 hour incubations with 2% blocking reagent/Solution 2 and 2% blocking reagent/20% heat-inactivated goat serum/Solution 2. To detect bound probe, the inventors performed immunohistochemistry with anti-digoxigenin-Alkaline Phosphatase antibody (1:2000, Roche). To develop the AP signal, embryos were washed with Solution 1, then incubated with Solution 4 (100 mM NaCl, 100 mM Tris-Cl, pH 9.5, 50 mM $MgCl_2$, 0.1% Tween-20) with developing reagents (0.25 mg/ml NBT (Nitro blue toluidine salt, Roche). Lastly, the embryos were washed with Solution 4, fixed in 4% PFA/PBS at 4° C. overnight, and imaged with a Zeiss 11 Stereoscope. Full length coding sequence was used to generate probes for both MyoD and Myomaker by using the digoxigenin labeling kit (Roche) followed by purification with MicroSpin™ G-25 columns (Amersham).

Radioisotopic in situ hybridization was performed as previously described33. Briefly, sections were deparaffinized, permeabilized, and acetylated prior to hybridization at 55° C. with riboprobes diluted in a mixture containing 50% formamide, 0.3M NaCl, 20 mM Tris-HCl, pH 8.0, 5 mM EDTA, pH 8.0, 10 mM $NaPO_4$, pH 8.0, 10% dextran sulfate, 1×Denhardt's, and 0.5 mg/ml tRNA. Following hybridization, the sections were rinsed with increasing stringency washes, subjected to RNAse A (2 µg/ml, 30 min at 37° C.) and dehydrated prior to dipping in K.5 nuclear emulsion gel (Ilford, UK). Autoradiographic exposure ranged from 21 to 28 days. The myogenin probe corresponded to nucleotides 31 through 638 of the coding sequence, whereas nucleotides 181-811 of the coding sequence was used for the M-cadherin probe. The Myomaker probe was full-length coding sequence. 35S-labeled sense and antisense probes were generated by Sp6 and T7 RNA polymerases, respectively, from linearized cDNA templates by in vitro transcription using the Maxiscript kit (Ambion).

Cardiotoxin Injury.

Cardiotoxin (CTX) from *Naja mossambica mossambica* (Sigma) was dissolved in sterile saline to a final concentration of 10 µM and aliquoted and stored at −20° C. Mice were anesthetized by intraperitoneal injection of 2.5% Avertin at (15 µl/g). Mouse legs were shaved and cleaned with alcohol.

Tibialis anterior (TA) muscles were injected with 50 μl of CTX with a 26-gauge needle.

X-Gal Staining.

For whole-mount X-gal staining, either embryos or tissues were fixed in 4% PFA/PBS (containing 0.01% deoxycholic acid and 0.02% Igepal) for 45 minutes at 4° C. with gentle shaking then rinsed 2 times with cold PBS. Samples were stained overnight in staining solution (5 mM $K_3Fe(CN)_6$, 5 mM $K_4Fe(CN)_6$, 2 mM $MgCl_2$, 1 mg/ml X-gal in PBS) followed by washing twice in PBS and post-fixing with 4% PFA/PBS.

For X-gal staining of cryosections or cells in culture the following procedure was employed: fix with 2% gluraraldehyde/PBS, wash 3 times in 0.1% sodium deoxycholate, 0.2% NP40 Substitute (Fluka), PBS, and incubate in staining solution (4 mM $K_3Fe(CN)_6$, 4 mM $K_4Fe(CN)_6$, 0.4 mM $MgCl_2$, 1 mg/ml X-gal, 0.1% sodium deoxycholate, 0.2% NP40 Substitute in PBS) at 37° C. overnight in the dark. The samples were then rinsed in PBS and fixed in 4% PFA/PBS for at least 20 minutes. Tissue sections were co-stained with light eosin, dehydrated, and mounted with Permount (Fisher). Cells were co-stained with nuclear fast red (Sigma).

Northern Blot Analysis.

Total RNA was extracted as previously described. Fifteen micrograms of RNA was extracted, resolved on a 1% agarose/MOPS (0.2M MOPS pH 7.0, 20 mM sodium acetate, 10 mM EDTA pH 8.0) gel, and transferred to Hybond N+ membrane (Amersham). The membrane was then incubated in hybridization buffer (1% crystalline BSA (fraction V), 1 mM EDTA, 0.5M NaHPO4, 7% SDS) for at least 2 hours at 68° C. followed by overnight incubation with probes labeled with [α-32P]dCTP using the RadPrime DNA Labeling System (Invitrogen). Myomaker probe was generated from fulllength coding sequence. The next day the membrane was washed with 1×SSC, 0.1% SDS for 10 minutes at room temperature followed by 3 washes at 68° C. with 0.5×SSC, 0.1% SDS. The membrane was exposed to film at −80° C. overnight and developed with a SRX101A Tabletop X-Ray Film Processor (Konica Minolta).

Histology and Immunohistochemistry.

For cryosections, skeletal muscle or limbs were dissected, embedded in gum tragacanth (1% in PBS), and frozen in 2-methylbutane cooled liquid nitrogen. For paraffin sections, tissue was fixed in 10% neutral buffered formalin and processed for routine paraffin histology. Frozen and paraffin sections were cut and stained with H&E using routine procedures. Immunohistochemistry was performed by fixation with 1% PFA/PBS, permeabilization with 0.2% Triton X-100 in PBS, blocking with PBS/1% BSA, 1% heat inactivated goat serum, 0.025% Tween20, incubation with primary antibody for at least 2 hours, incubation with secondary Alexa-Fluor antibodies (Invitrogen) for 1 hour, and mounting with VectaShield containing DAPI (Vector Laboratories). Anti-mouse myosin (my32, Sigma) and desmin (DAKO) antibodies were used at 1:100. The TUNEL (Invitrogen) reaction was performed exactly as described by the manufacturer. Slides were visualized using a Leica DM RXE microscope.

Isolation of Primary Myoblasts and Immunocytochemistry.

Limbs were dissected from E15 to E17.5 embryos and dissociated in 0.05% Collagenase D (Roche) in PBS at 37° C. for 2-3 hrs. Ten milliliters of culture media (20% FBS/Ham F10) was added to the suspension and triturated followed by centrifugation at 1500×g for 10 minutes at 4° C. The pellet was resuspended in 10 ml of growth media (20% FBS/Ham F10+2.5 ng/ml bFGF (Promega)), filtered through a 100 μm cell strainer, and plated on a 10 cm laminin coated culture dish. To enrich for myoblasts, cultures were incubated in a small volume of PBS, and the myoblasts were dislodged by knocking the plate lightly. To induce myogenesis, the cultures were placed in differentiation media (2% horse serum, DMEM) for 3-5 days. Immunocytochemistry was performed by fixing with 4% PFA/PBS, permeabilization with 0.2% Triton X-100 in PBS, blocking with 3% BSA/PBS, incubation with primary antibody for at least 2 hours, then incubation with Alexa-Fluor secondary antibodies for 1 hour. Myosin antibody, used as described above, M2 Flag antibody (Sigma) at 1:500, BrdU (Roche) at 1:100, EEA1 (generous gift of Schmid Lab, University of Texas-Southwestern) at 1:500, GM130 (BD Pharmingen) at 1:300, cyclophilin D (Abcam) at 1:200, PDI (Cell Signaling) at 1:500. Cultures were co-stained with Phalloidin-rhodamine (Invitrogen) at 1:200 and nuclei were stained with Hoechst (Invitrogen). For staining of live cells, the inventors first washed the cells with PBS and incubated in blocking buffer (3% BSA/PBS) for 15 min. Primary antibody incubation was then performed on ice, followed by fixation with 4% PFA/PBS, and incubation with secondary antibody. These cultures were visualized on a Zeiss LSM 780 Confocal Microscope or a Nikon Eclipse Ti Fluorescent Microscope.

Cloning, Generation of Retroviruses, and C2C12 Infection.

The inventors cloned Myomaker coding sequence from P0 WT tongue cDNA using the following primers:

```
Myomaker-F:
                                    (SEQ ID NO: 7)
5'-ATGGGGACAGTTGTAGCCAA-3'

Myomaker-R:
                                    (SEQ ID NO: 8)
5'-TCAGACACAAGTGCAGCAGA-3'
```

Myomaker-Flag was generated by independently cloning the regions immediately upstream (5' PCR product) and downstream (3' PCR product) of the site of Flag insertion. These products were used as templates, and Myomaker-F and Myomaker-R as primers, in a standard PCR sewing reaction to generate full-length Myomaker-Flag.

Retroviral plasmid DNA was generated by subcloning Myomaker and Flag-tagged Myomaker cDNA into the retroviral vector pBabe-X31. GFP and dsRed retrovirus have been described previously32. Ten micrograms of retroviral plasmid DNA was transfected using FuGENE 6 (Roche) into Platinum E cells (Cell Biolabs) which were plated on a 10 cm culture dish at a density of 3×106 cells per dish, 24 hours before transfection. Forty-eight hours after transfection, viral media was collected, filtered through a 0.45 μm cellulose syringe filter, and mixed with polybrene (Sigma) at a final concentration of 6 μg/ml. C2C12 myoblasts (obtained from ATCC) were plated on 35 mm culture dishes at a density of 3×105 cells/dish 24 hours prior to infection with viral media. Eighteen hours after infection, virus was removed, cells were washed with PBS, and replaced with differentiation media. These cultures were assayed between 1 and 5 days of differentiation. The actin inhibitors Cytochalasin D (Sigma) and lantrunculin B (Sigma) were used at a concentration of 0.3 μM and 0.1 μM, respectively.

Subcellular Fractionation and Western Blot Analysis.

To fractionate C2C12 cells into cytosol and membrane fractions, the inventors first washed a 10 cm dish with cold PBS and lysed the cells by dounce homogenation in hypotonic buffer (10 mM Tris pH 8.0, 1 mM EDTA). The homgenate was centrifuged at 500×g for 5 min. to pellet nuclei and cell debris. The supernatant was centrifuged at 100,000×g for 20 min to pellet membrane structures. The supernatant from this step was the cytosol fraction and the membrane fraction was solubilized in an equal volume of hypotonic buffer+1% n-Dodecyl β-D-maltoside (DDM, Sigma) for further analyses by immunoblotting. For analysis of whole cell extracts, DDM solubilization was used (20 mM HEPES, 150 mM NaCl, 2 mM EDTA, 10% glycerol, 1% DDM). For immunoblotting, equal protein amounts were separated on a 12% SDS-PAGE, transferred to a PVDF membrane (Millipore), blocked in 5% milk in TBS-tween and incubated with primary antibodies. The following antibodies were used: M2 Flag (Sigma, 1:1000), Gapdh (Millipore, 1:10000), VDAC (Santa Cruz, 1:1000), α-tubulin (Sigma, 1:1000), myosin (my32, Sigma, 1:1000), and myogenin (Developmental Studies Hybridoma Bank, 1:1000).

Cell Mixing.

WT myoblasts were mixed with either Myomaker+/− or Myomaker−/− myoblasts at equal ratios (approximately $1 \times 10^5$ cells per genotype), plated on a well of a laminin coated 12-well plate, and induced to differentiate the next day. 10T1/2 fibroblasts were infected with either GFP- and empty-retrovirus or GFP- and Myomaker-retrovirus for 18 h. After infection, cells were washed multiple times and then trypsinized, and mixed with C2C12 myoblasts at a 1:1 ratio ($1 \times 10^5$ of each cell type) and plated on one well of a 6 well plate in differentiation media. GFP and myosin expression was analyzed 4 days after differentiation. A similar protocol was performed to assess incorporation of BrdU-labeled fibroblasts into myotubes with minor modifications. 10T1/2 fibroblasts were incubated with BrdU (Roche) at a final concentration of 10 μM for 18 hours. They were then infected with either empty-retrovirus or Myomaker-retrovirus and mixed with C2C12 myoblasts that had been infected with dsRed-retrovirus.

Time-Lapse Microscopy.

C2C12 myoblasts were infected with GFP and Myomaker retrovirus or with dsRed retrovirus and fibroblasts were infected with GFP and Myomaker retrovirus. GFP and dsRED was visualized using a Perkin Elmer Ultraview Spinning Disk Confocal Microscope with a chamber for control of temperature and CO2. Images were captured every 15 minutes using Volocity 5.4.0 software. Images were analyzed and videos assembled using ImageJ.

Quantitation and Statistics.

Each histological analysis of embryonic skeletal muscle was performed on four samples per genotype. The differentiation index was calculated as the percentage of nuclei in myosin-positive cells. The fusion index was calculated as the percentage of nuclei contained in myosin-positive myotubes. Structures must contain at least 2 nuclei to be considered a myotube. To quantitate fusion between WT myoblasts and either Myomaker+/− or Myomaker−/− myoblasts, the inventors calculated the percentage of LacZ+ myotubes containing ≥3 nuclei. To quantitate fusion between fibroblasts and myoblasts, the inventors calculated the percentage of GFP+ myosin+ cells or the percentage of BrdU+ myotube nuclei. For each quantitation, at least 3 independent experiments were performed in duplicate and at least 6 random fields were imaged per sample. Data are presented as mean±SEM. Differences between groups were tested for statistical significance using the unpaired two-tailed Student's t test. $P<0.05$ was considered significant.

Example 2—Results

Discovery and Regulation of Myomaker.

To search for novel skeletal muscle regulatory genes, the inventors interrogated the NCBI UniGene database for genes with expression profiles similar to those of Myod and Myogenin, which encode important muscle-specific transcription factors (Davis et al., 1987 and Hasty et al., 1993). Among the genes identified in this screen, was Transmembrane protein 8c (Tmem8c), which had not been previously studied. Based on the observations described below, the inventors named this gene Myomaker.

Figure 1B:
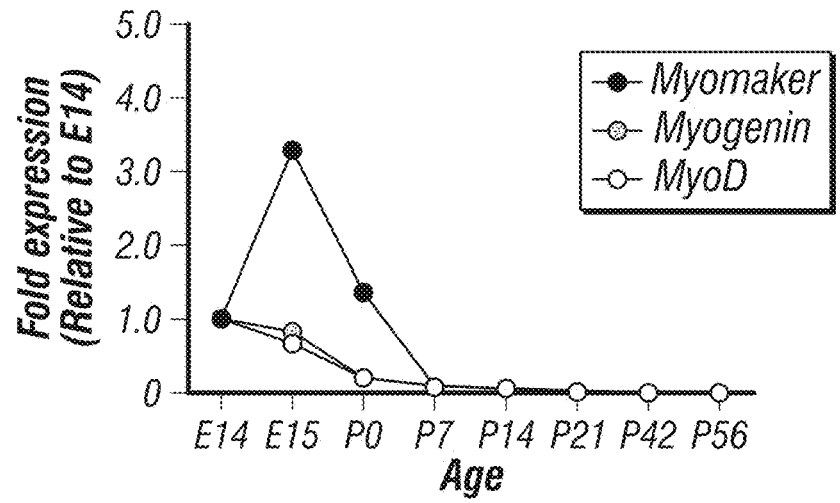
Figure 1C:
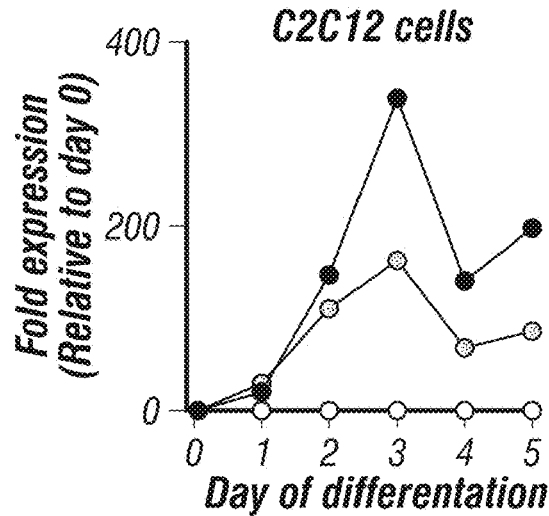
Figure 6A:
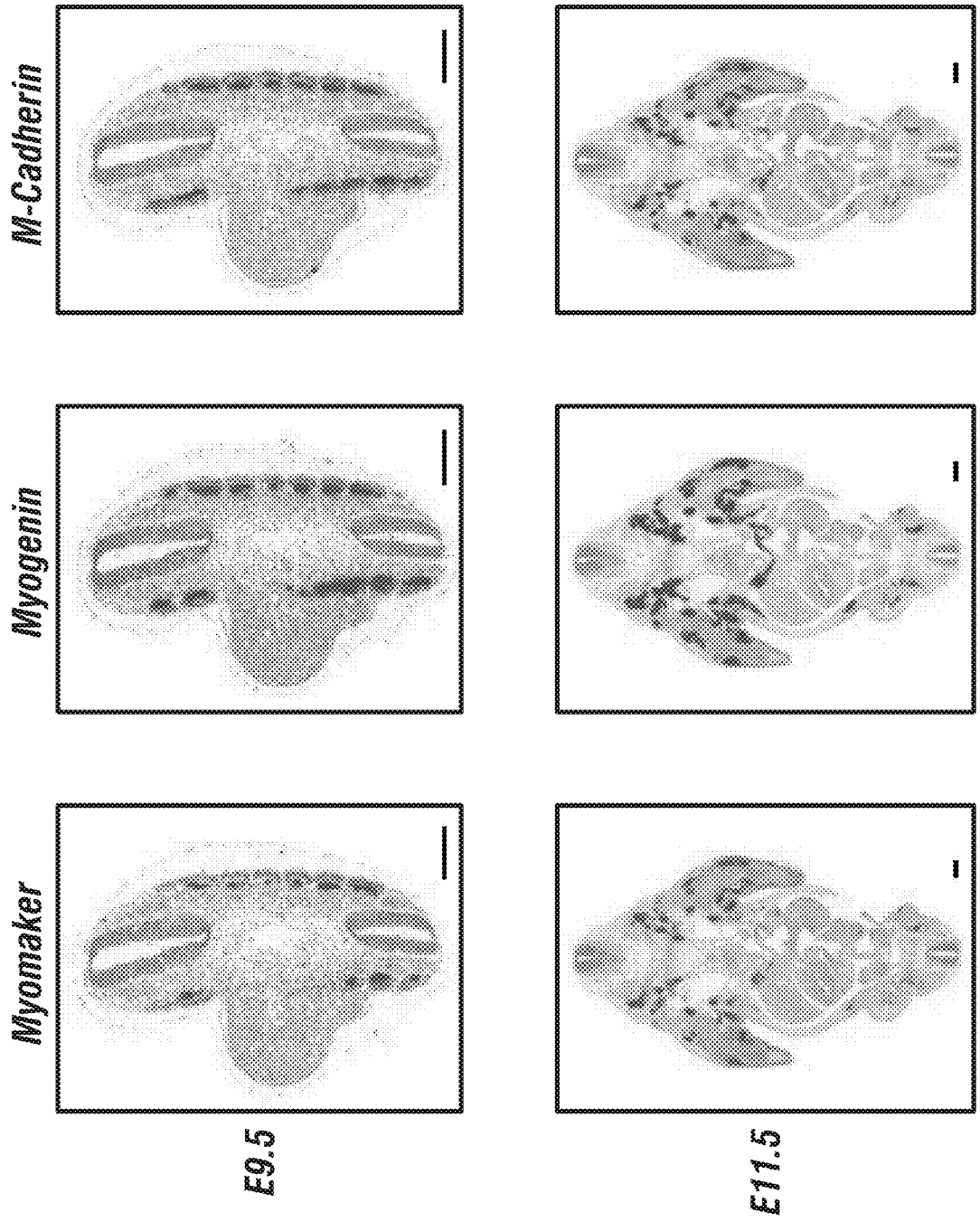
FIGS. 6A-C. The myomaker gene is skeletal muscle-specific in the embryo.
Figure 6B:
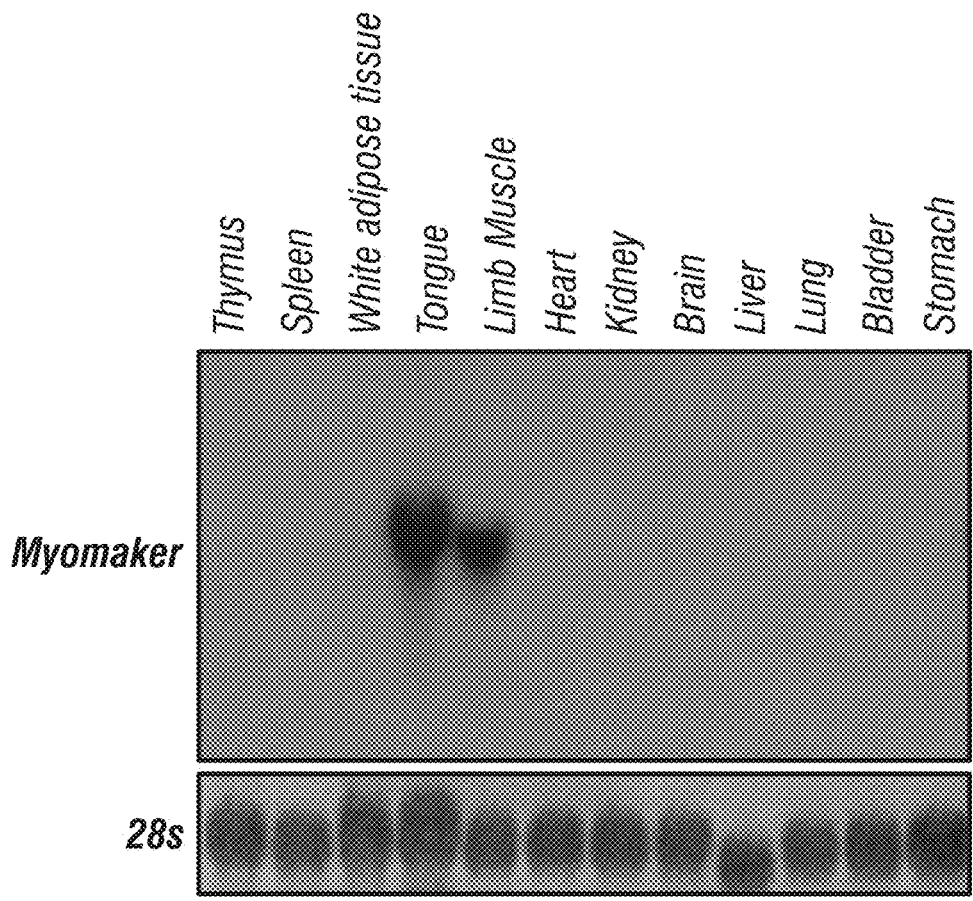
Figure 6C:
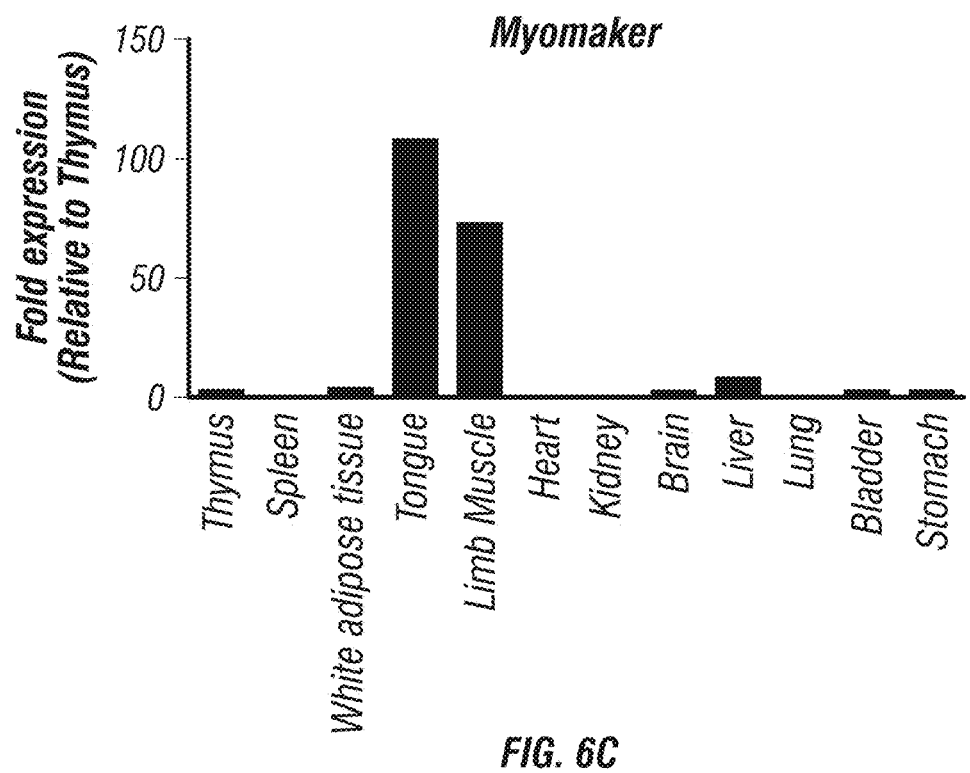

During mouse embryogenesis, Myomaker is robustly expressed in the myotomal compartment of the somites, and later is expressed in limb buds and axial skeletal muscles (FIG. 1A and FIG. 6A). Expression of Myomaker in the myotomes coincides with expression of other known muscle transcripts, such as Myogenin and M-cadherin (FIG. 6A). Myomaker mRNA is expressed in skeletal muscle of the tongue and is subsequently down-regulated upon completion of muscle formation, similar to the expression pattern of Myod and Myogenin (FIG. 1B). Myomaker expression was not detected in tissues other than skeletal muscle in E19 embryos (FIGS. 6B-C). In the C2C12 skeletal muscle cell line, Myomaker mimics Myogenin expression, increasing sharply during differentiation and fusion (FIG. 1C).

Figure 1D:
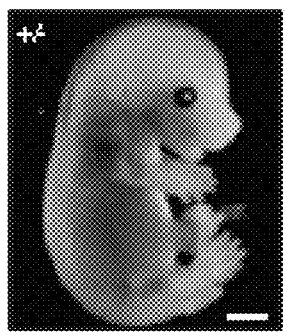
Figure 1D:
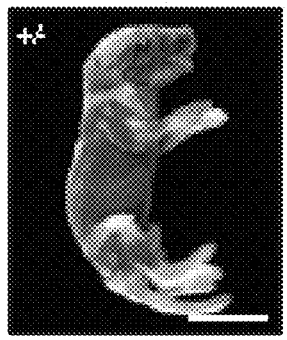
Figure 7A:
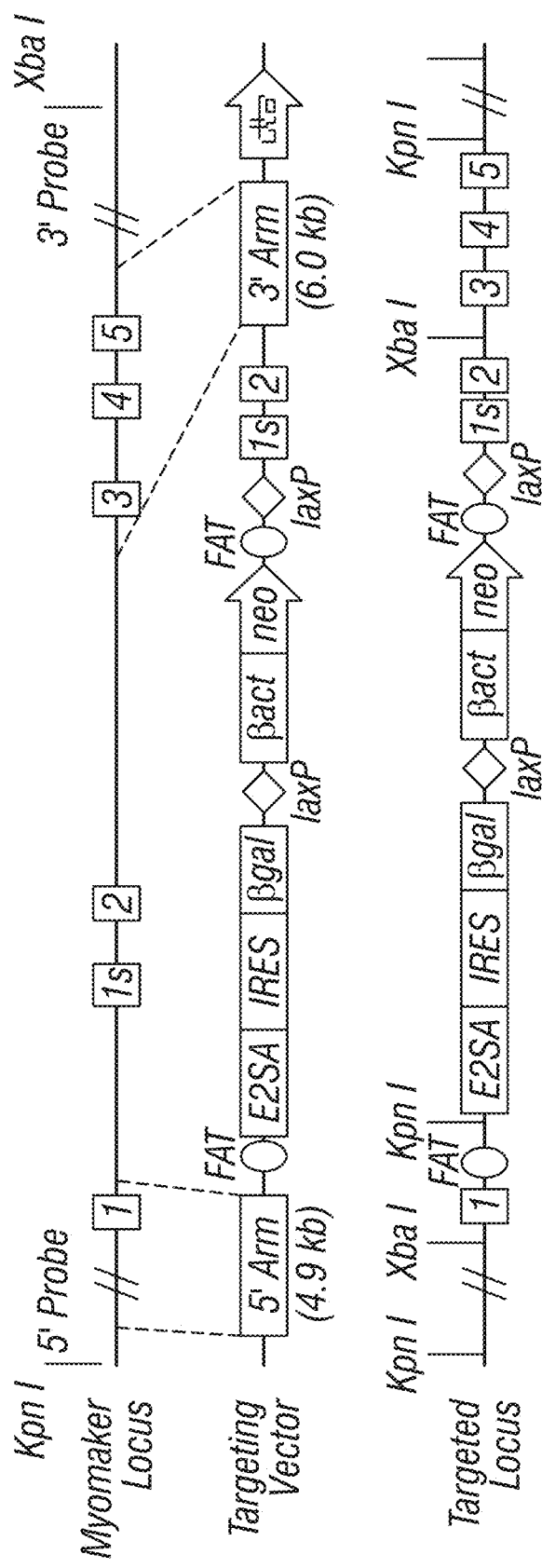
FIGS. 7A-G. The myomaker-LacZ allele recapitulates expression of myomaker RNA and loss of myomaker is lethal.
Figure 7B:
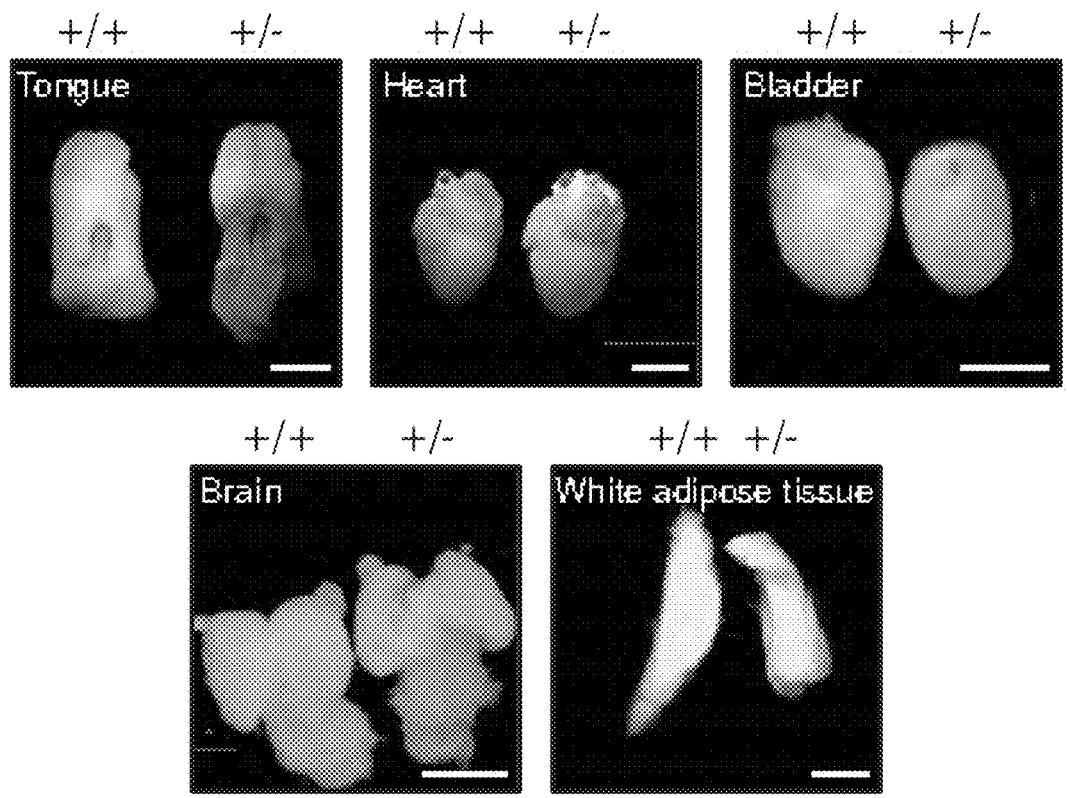
Figure 7D:
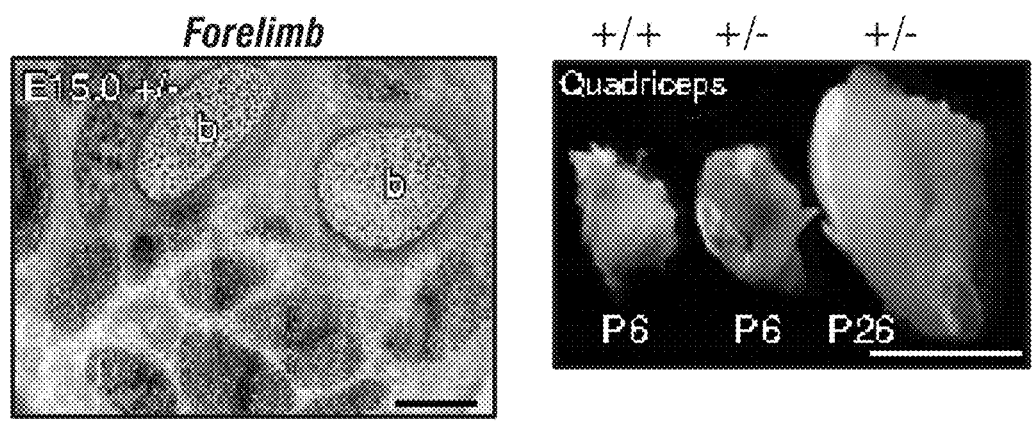
Figure 7C:
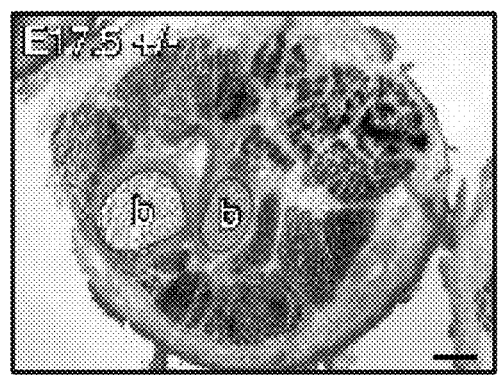

To begin to assess the function of Myomaker in skeletal muscle, the inventors obtained ES cells that contained a LacZ-Neo cassette in intron 1 of the Myomaker locus (FIG. 7A). In this allele, exon 1 of Myomaker is spliced to lacZ, preventing expression of a functional Myomaker transcript. The inventors refer to mice heterozygous and homozygous for the Myomaker-lacZ allele as Myomaker$^{+/-}$ and Myomaker$^{-/-}$ mice, respectively. X-gal staining of Myomaker$^{+/-}$ mice showed expression of the targeted lacZ allele specifically in skeletal muscle, and not in other muscle tissues or non-muscle tissues (FIG. 1D and FIGS. 7B-C). Like the endogenous Myomaker gene, skeletal muscle expression of the Myomaker-lacZ allele declined postnatally (FIG. 7D).

Figure 1E:
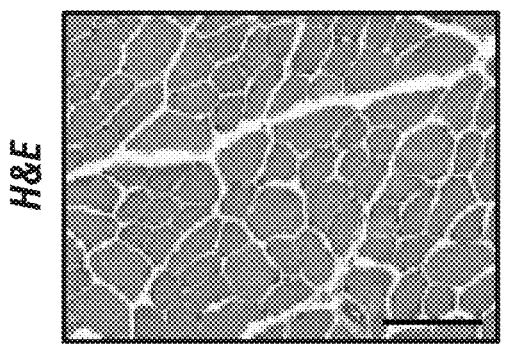
Figure 1E:
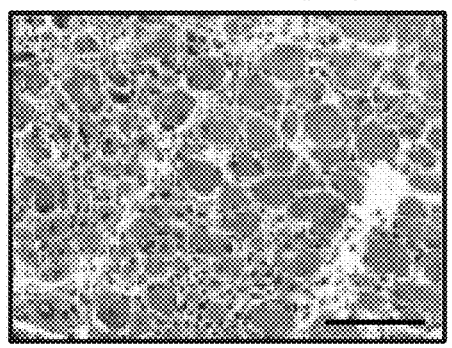
Figure 1E:
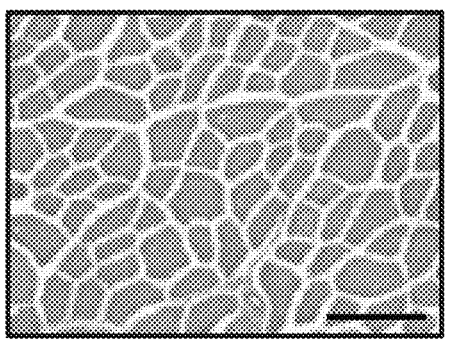
Figure 1E:
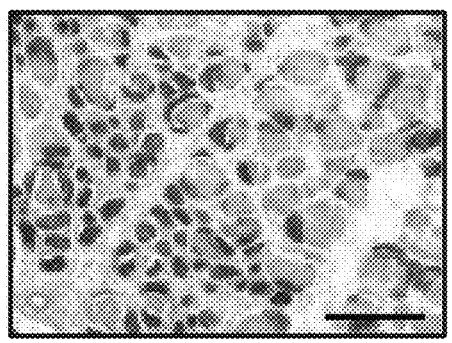
Figures 7E, 7F, 7G:
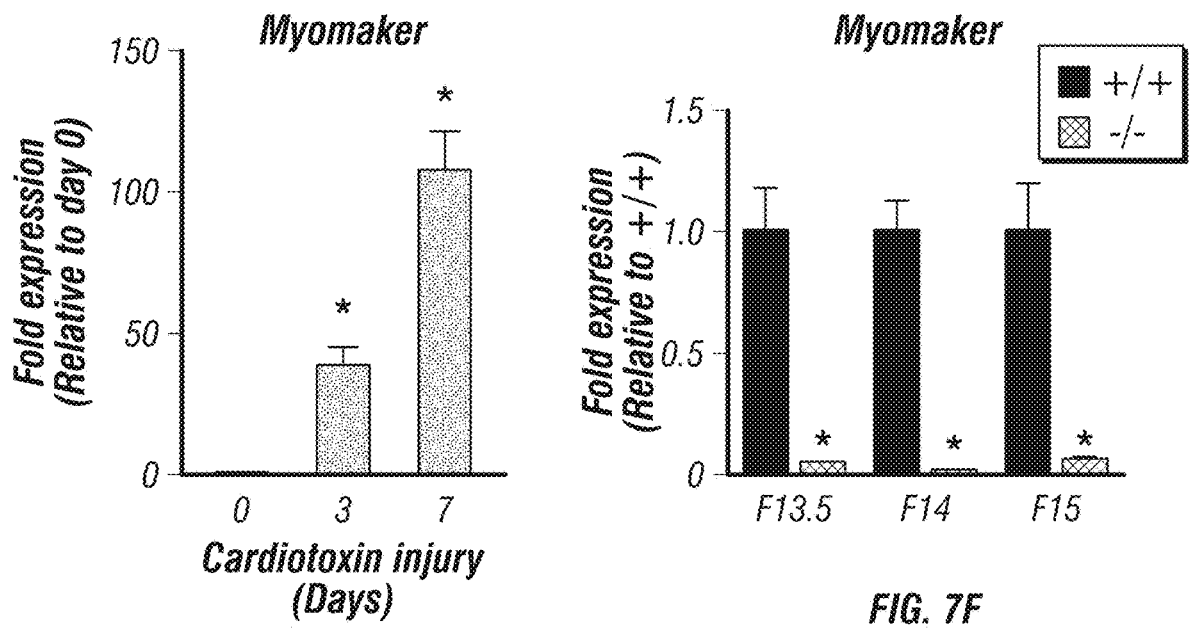

Adult skeletal muscle regenerates in response to damage, due to the activation of satellite cells, which fuse with residual muscle fibers (Buckingham 2006 and Kang and Krauss 2010). The inventors tested whether Myomaker expression is re-activated during adult muscle regeneration by inducing muscle injury in adult mice. Expression of the Myomaker-LacZ allele and Myomaker mRNA and was strongly induced in regenerating muscle after cardiotoxin injury (FIG. 1E and FIG. 7E). They concluded that Myomaker is expressed specifically in skeletal muscle during embryogenesis and adult muscle regeneration.

Genetic Loss of Myomaker Prevents Skeletal Muscle Formation.

Figures 2A, 2B, 2C:
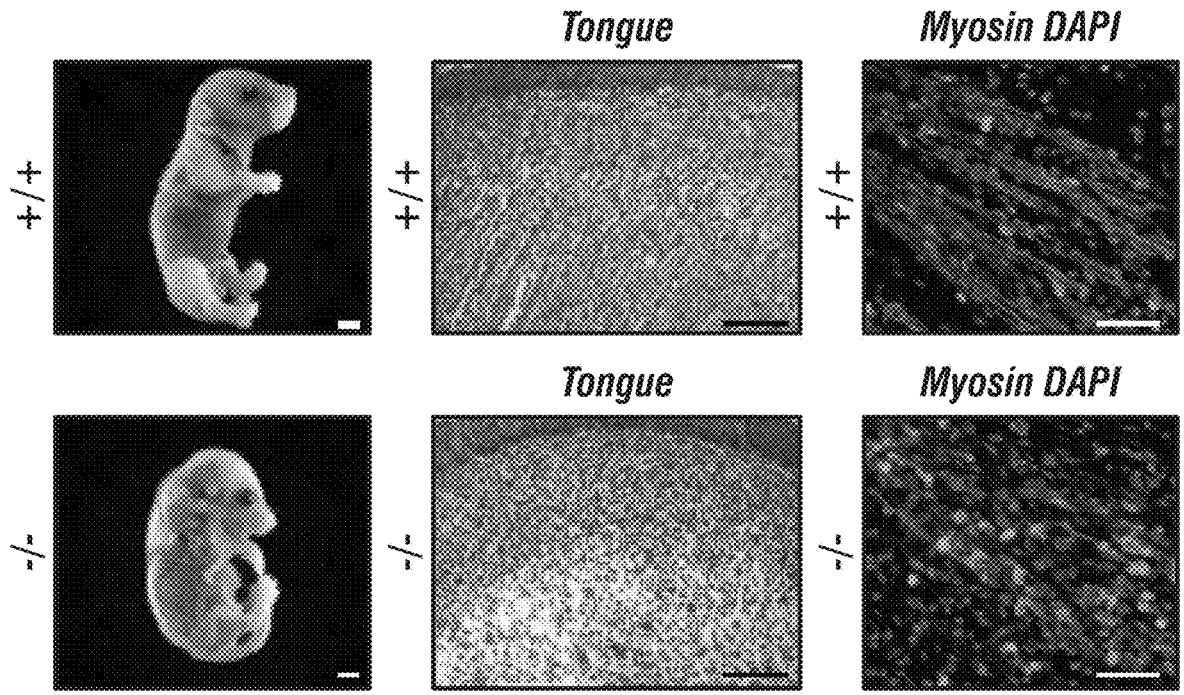
FIGS. 2A-C. Myomaker is essential for skeletal muscle development.
Figure 8A:
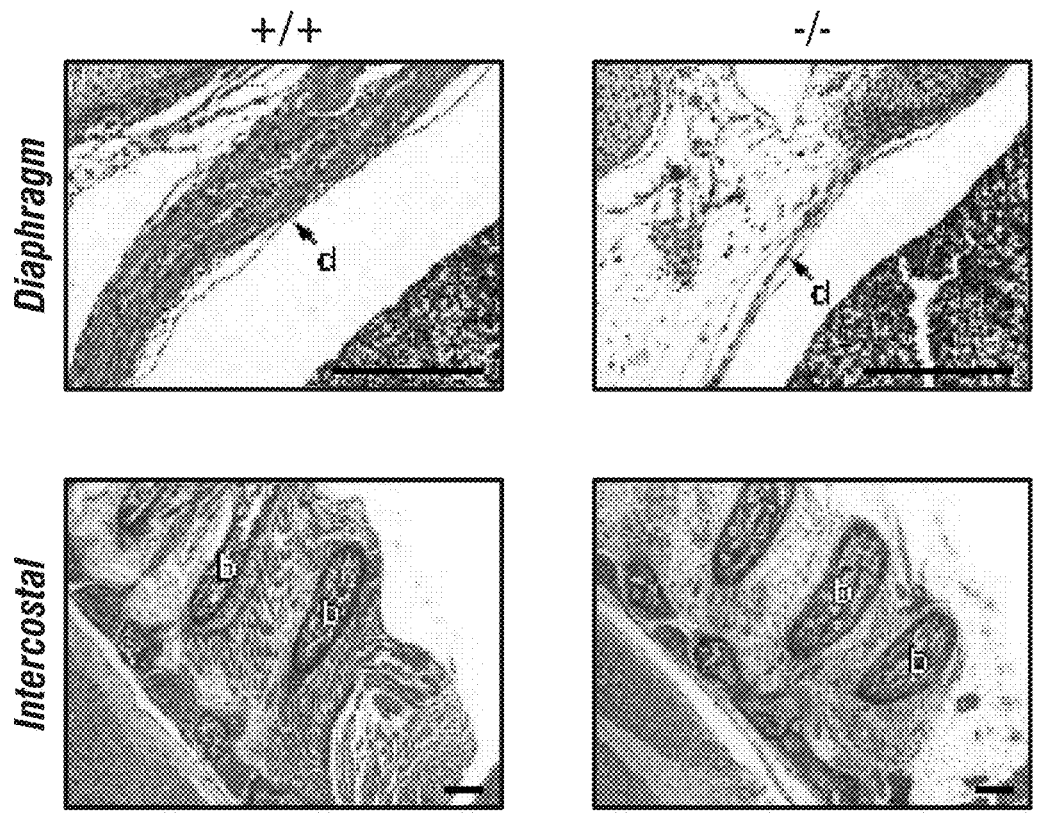
FIGS. 8A-G. Myomaker is necessary for proper muscle formation despite normal specification.
Figure 8B:
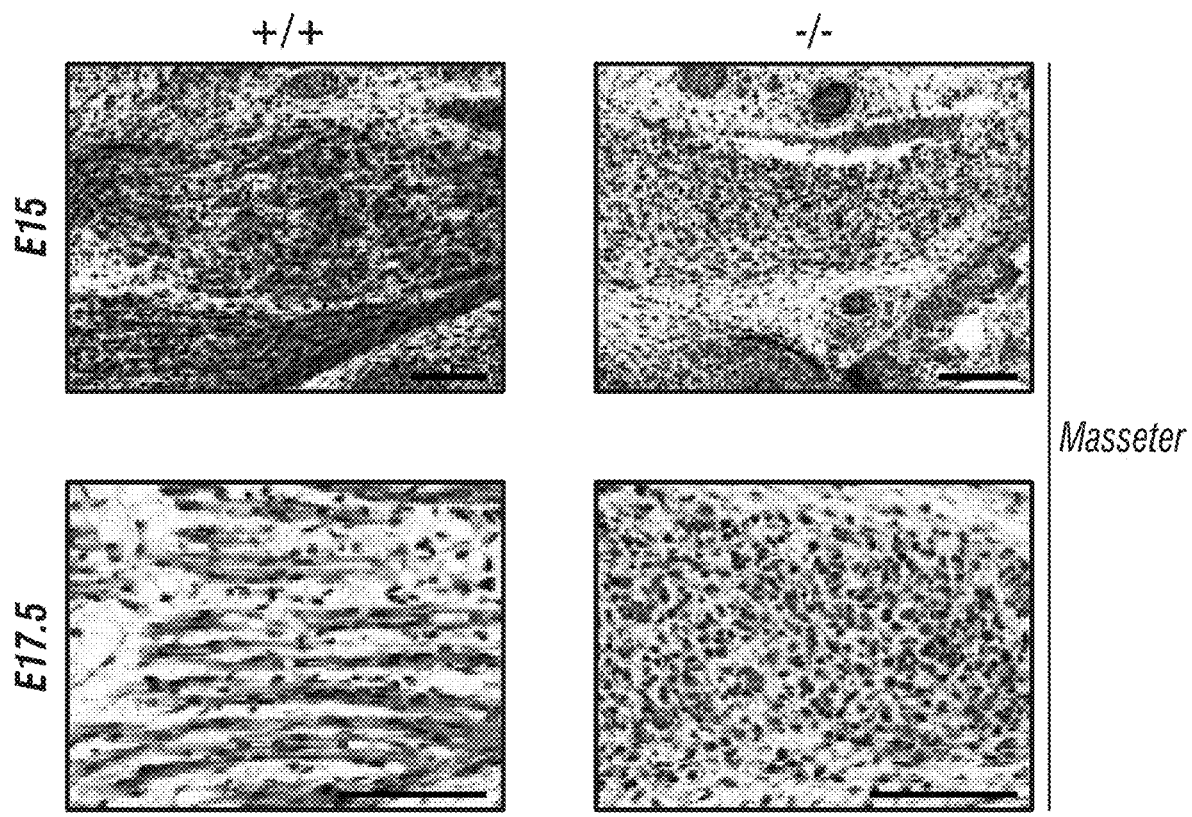

The inventors generated Myomaker$^{-/-}$ mice by interbreeding of heterozygous mice. Myomaker transcripts were absent in skeletal muscle of Myomaker$^{-/-}$ mice, confirming that the targeting strategy created a null allele (FIG. 7F). Myomaker$^{-/-}$ mice were observed at normal Mendelian ratios at E15 and E17.5; however, the inventors failed to detect any live Myomaker$^{-/-}$ mice at P7, suggesting earlier lethality due to muscle dysfunction (FIG. 7G). Full-term Myomaker$^{-/-}$ embryos were alive, as their hearts were beating, but were paralyzed and kyphotic with flaccid limbs, hallmarks of skeletal muscle deficiency (FIG. 2A). Strikingly, no semblance of differentiated muscle tissue was present in the trunk, limbs, or head of Myomaker$^{-/-}$ animals (FIG. 2B and FIGS. 8A-B).

Figure 8C:
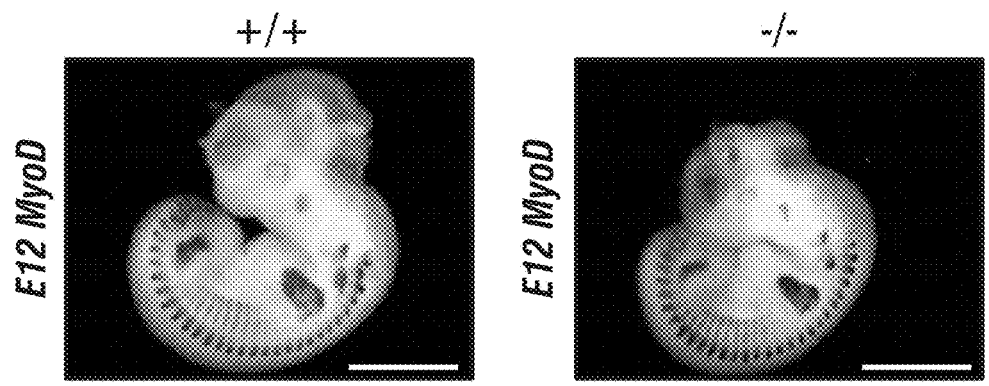
Figure 8D:
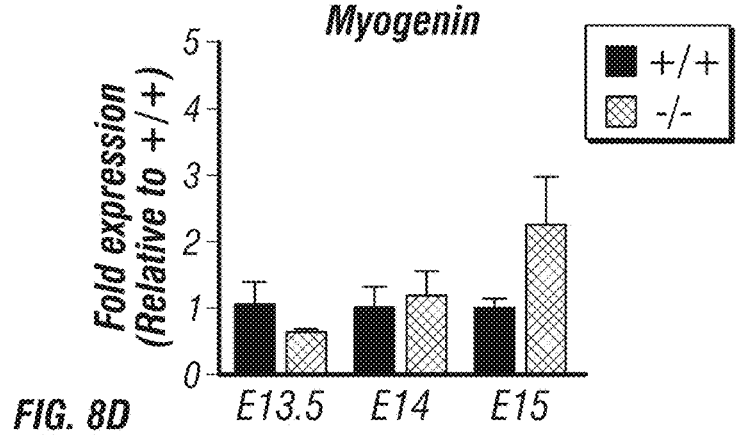
Figure 8E:
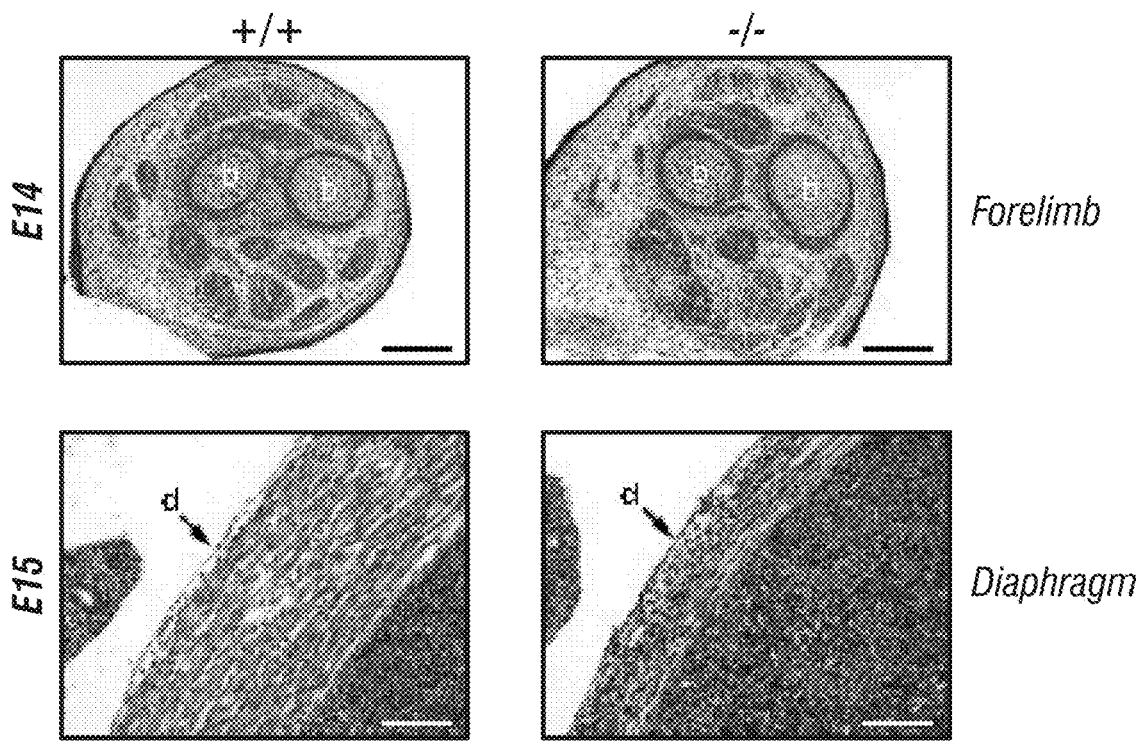
Figure 8F:
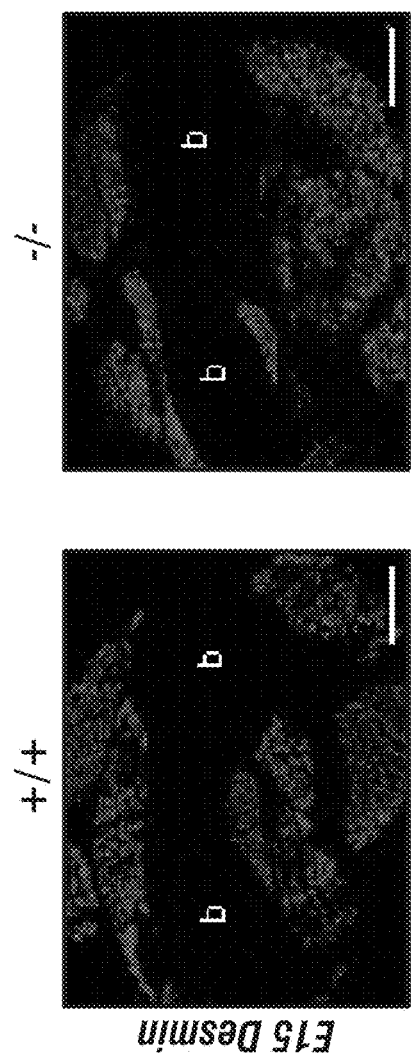

Muscle formation requires myoblast specification, migration, differentiation, and fusion (Bentzinger et al., 2012, Berkes & Tapscott 2005, Buckingham 2006, Kang and Krauss 2010). In principle, dysfunction of one or more of these processes could contribute to lethality and lack of muscle formation in Myomaker$^{-/-}$ embryos. To begin to define the mechanistic actions of Myomaker, the inventors tested the functionality of these processes. The muscle-specific transcription factors, MyoD and Myogenin, were expressed normally in Myomaker$^{-/-}$ embryos (FIGS. 8C-D), suggesting that specification of the skeletal muscle lineage occurred normally in the absence of Myomaker. Muscle tissues were present in Myomaker$^{-/-}$ embryos, indicating that muscle precursor cells were organized appropriately in the absence of Myomaker (FIG. 8E). Desmin, a marker of muscle cells, was expressed comparably in Myomaker$^{-/-}$ and wild-type (WT or +/+) forelimbs, confirming that myoblast migration was unaltered (FIG. 8F). These findings suggested Myomaker functions after myoblast specification and migration. Longitudinal sections through hindlimb muscles of Myomaker$^{-/-}$ embryos at E14 revealed the expression of myosin, a muscle differentiation marker, but an absence of multi-nucleated myofibers (FIG. 2C). These findings imply that Myomaker$^{-/-}$ myoblasts can activate muscle-specific gene expression and differentiate, but lack the ability to fuse.

Figure 8G:
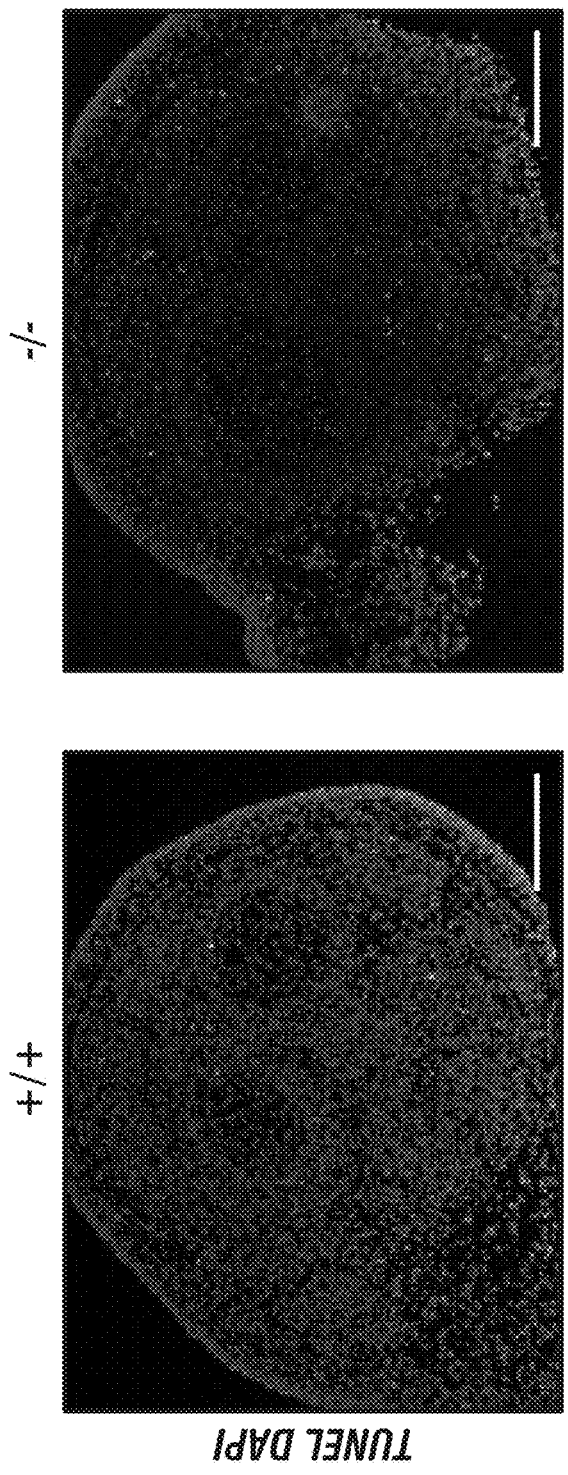

Myomaker$^{-/-}$ muscle tissues contained only mononucleated cells, however, the cell number was clearly reduced in each muscle analyzed. One possible explanation for this decrease is cell death, which has previously been associated with a failure to fuse (Vasyutina et al., 2009 and Gruenbaum-Cohen et al., 2012). Indeed, TUNEL staining revealed increased apoptotic nuclei in muscle forming regions of Myomaker$^{-/-}$ mice, suggesting that fusion defective myoblasts are non-viable (FIG. 8G).

Myomaker Controls Myoblast Fusion.

Figure 3A:
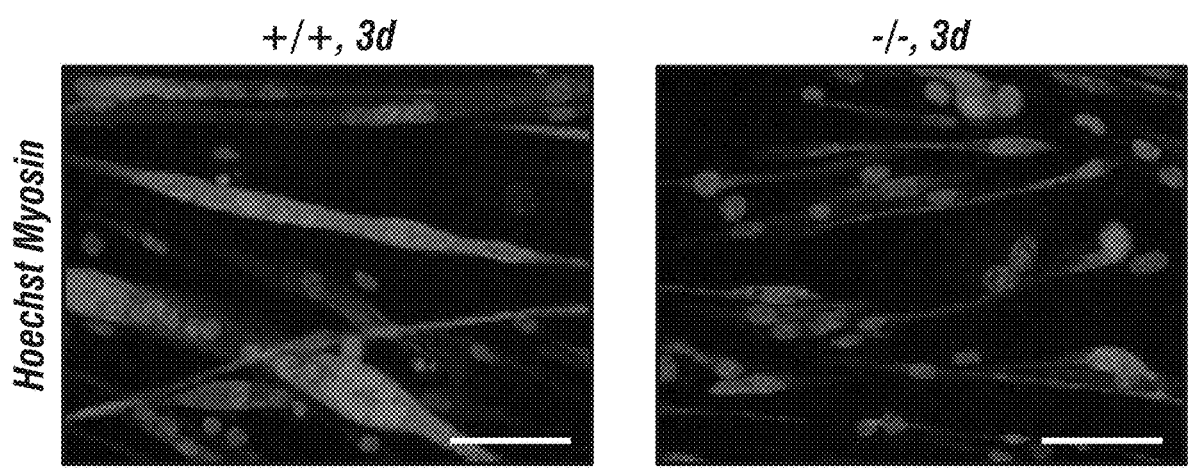
Figure 9A:
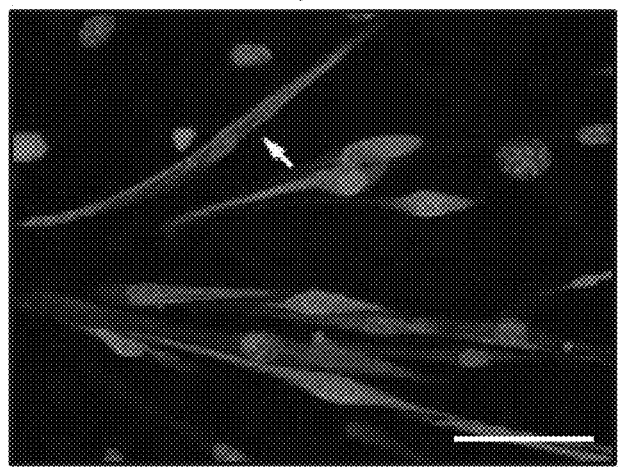
(FIG. 9A) Myomaker null myoblasts were differentiated and we observed a small number of bi-nucleated cells (arrow).
Figure 9B:
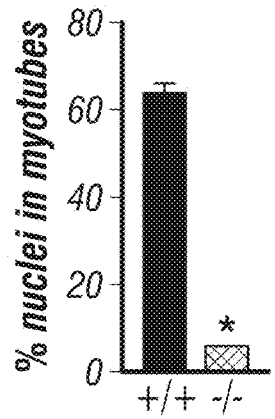
(FIG. 9B) The fusion index was calculated as the percentage of nuclei contained in myotubes (a myosin+ cell with at least two nuclei).
Figure 9C:
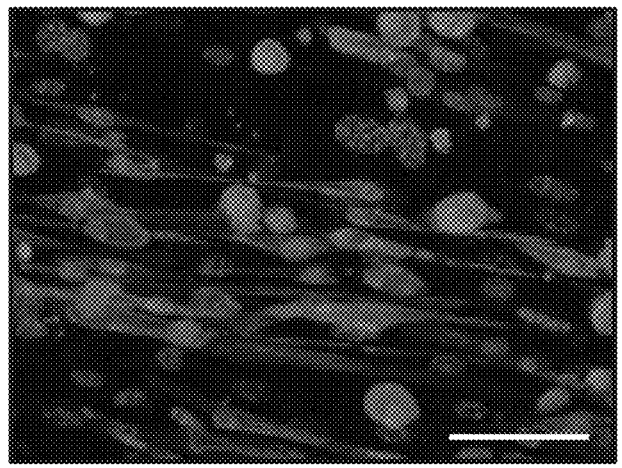
(FIG. 9C) Myomaker−/− myoblasts failed to fuse even after 5 days of differentiation.

To definitively confirm that Myomaker functions in myoblast fusion, the inventors employed multiple in vitro differentiation assays using primary myoblasts and the C2C12 muscle cell line. First, the inventors isolated myoblasts from WT and Myomaker$^{-/-}$ embryos and after 3 days of differentiation, WT myoblasts formed extensive myotubes containing many nuclei (FIG. 3A). In contrast, the vast majority of Myomaker$^{-/-}$ myoblasts remained mono-nucleated, with only a small percentage forming bi-nucleated myosin positive cells (FIGS. 3A-B and FIG. 9A). Quantification of the differentiation index revealed no differences in the ability of Myomaker$^{-/-}$ myoblasts to express myosin, however the fusion index was dramatically reduced compared to WT myoblasts (FIG. 3C and FIG. 9B), even when plated for prolonged periods at higher density than WT myoblasts, indicating that fusion was blocked rather than simply delayed (FIG. 9C). The inventors conclude that the lack of muscle formation in Myomaker$^{-/-}$ embryos is due to a block of myoblast fusion, representing the cellular mechanism of Myomaker function.

Figure 9D:
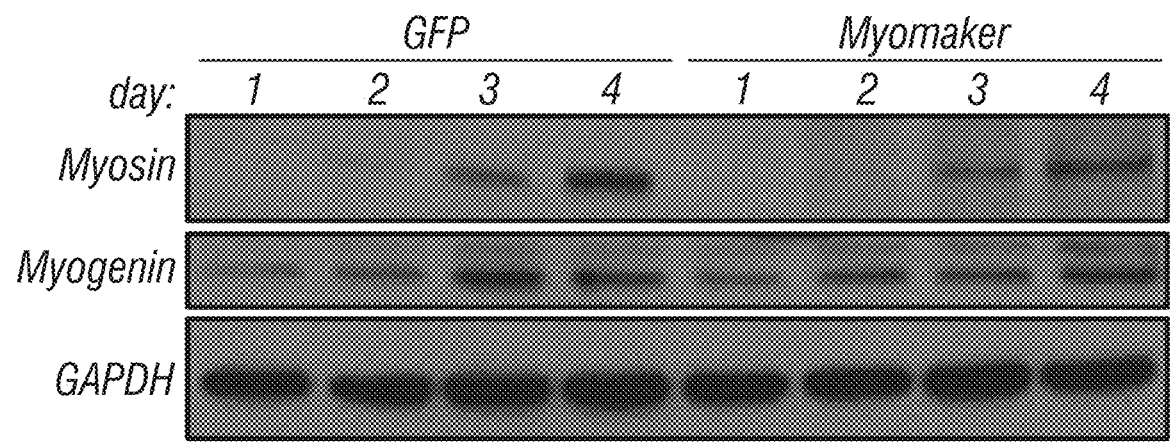
(FIG. 9D) Western blots for myosin and myogenin were performed on C2C12 cells on the indicated day of differentiation after GFP or myomaker infection.
Figure 9E:
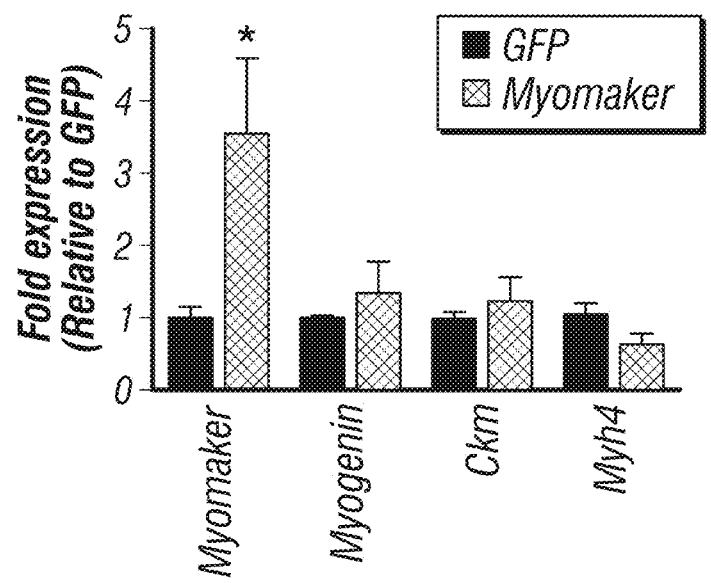
(FIG. 9E) qPCR for myogenic differentiation genes (Ckm=muscle creatine kinase, Myh4=myosin heavy chain 4) revealed that myomaker-mediated fusion enhancement did not alter levels of differentiation (n=3 for GFP and n=3 for myomaker).
Figure 9F:
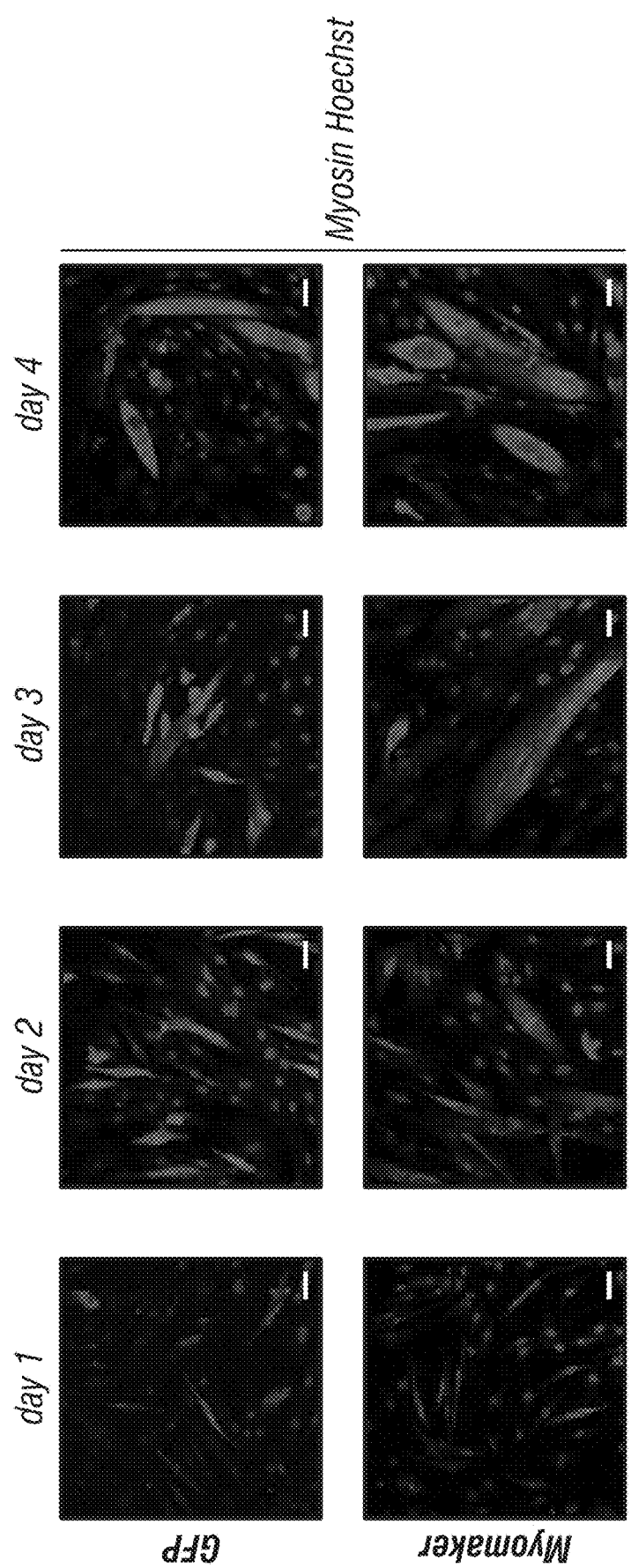
(FIG. 9F) C2C12 myoblasts were immunostained with myosin and Hoechst (nuclei) to evaluate the kinetics of fusion after GFP or myomaker infection. Myomaker-infected C2C12s exhibited an increase rate of appearance of myotubes with multiple nuclei. On day 3, myotubes with >20 nuclei were apparent in C2C12 cells with overexpressed myomaker, whereas such myotubes were not detected in control cultures on this day.
Figure 9G:
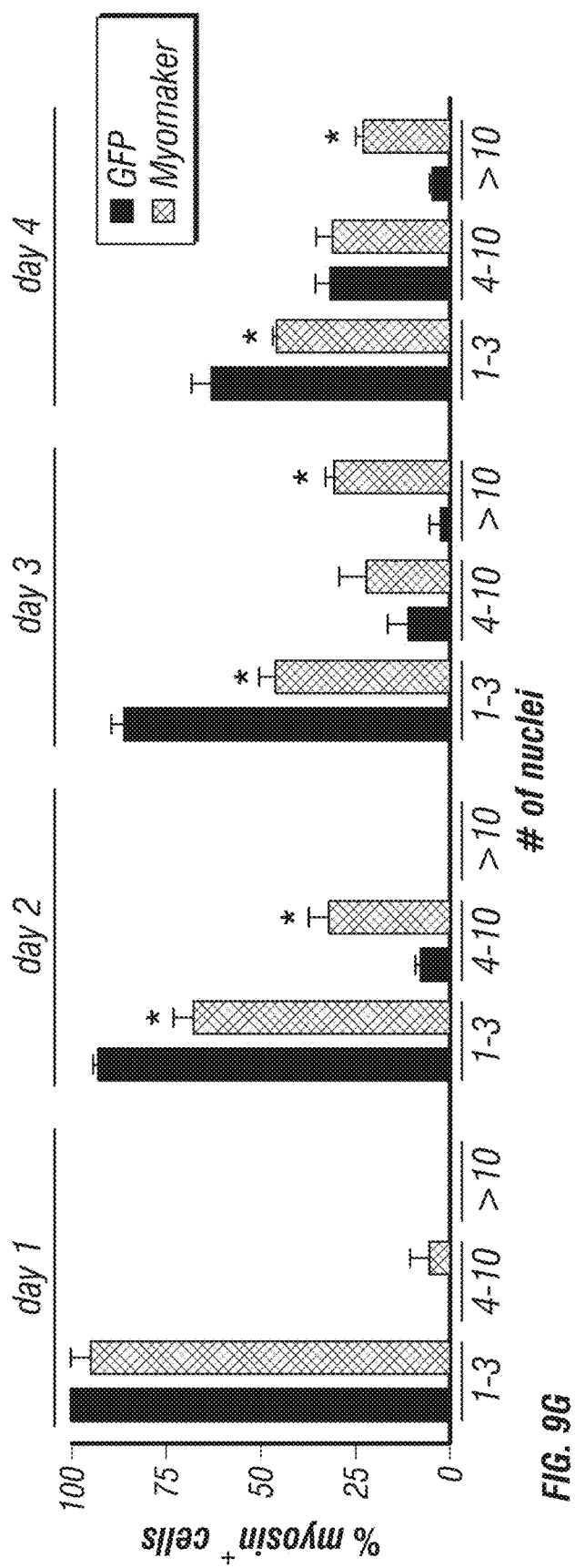
(FIG. 9G) Quantitation of the percentage of myosin+ cells that contained the indicated number of nuclei on day 1-day 4 of differentiation. Data are presented as mean±SEM. *$P<0.05$ compared to GFP-infected cells on that day of differentiation.
Figure 9H:
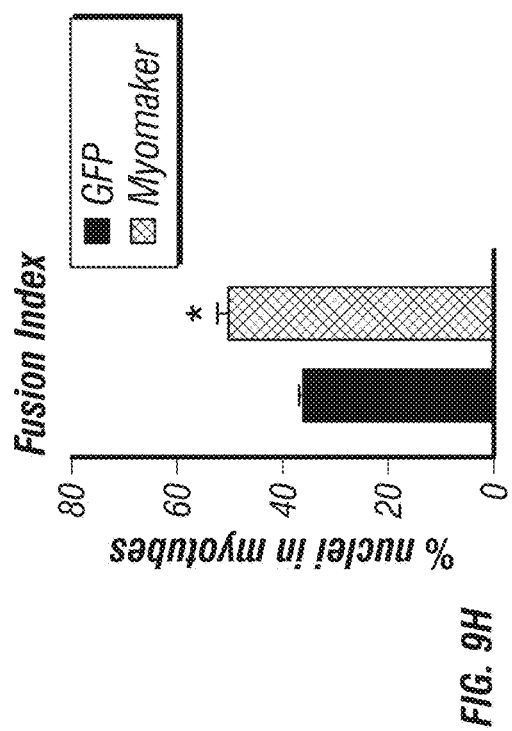
(FIG. 9H) The fusion index on day 4 of differentiation was quantified as in FIG. 9B and showed an increase in myotube nuclei after myomaker infection. Scale bars.

To test whether Myomaker was a limiting factor in myoblast fusion, the inventors infected C2C12 cells with a Myomaker retrovirus one day prior to differentiation and assessed the consequences on myoblast fusion. Myomaker over-expression caused a dramatic increase in fusion after 4 days of differentiation (FIG. 3D). The kinetics of induction of myogenin and myosin, and maximal levels of expression of the terminal differentiation genes (Myogenin, Ckm, and Myh4) were comparable in Myomaker-infected cells and cells infected with a GFP control virus (FIGS. 9D-E). Despite no differences in expression of muscle differentiation factors, the inventors observed a robust increase in the appearance of myotubes with multiple nuclei in the cultures infected with Myomaker, further indicating that Myomaker functions specifically in myoblast fusion and does not regulate differentiation per se (FIG. 9B). Quantitation of the fusion index and the number of nuclei per myotube indicated a robust activity of Myomaker to increase the fusion capability of these cells (FIG. 3E and FIGS. 9G-H). Furthermore, through live cell imaging, the inventors visualized myotube-myotube fusion in Myomaker-infected cells (data not shown). These data demonstrate that Myomaker is sufficient to enhance C2C12 myoblast fusion.

Figure 10B:
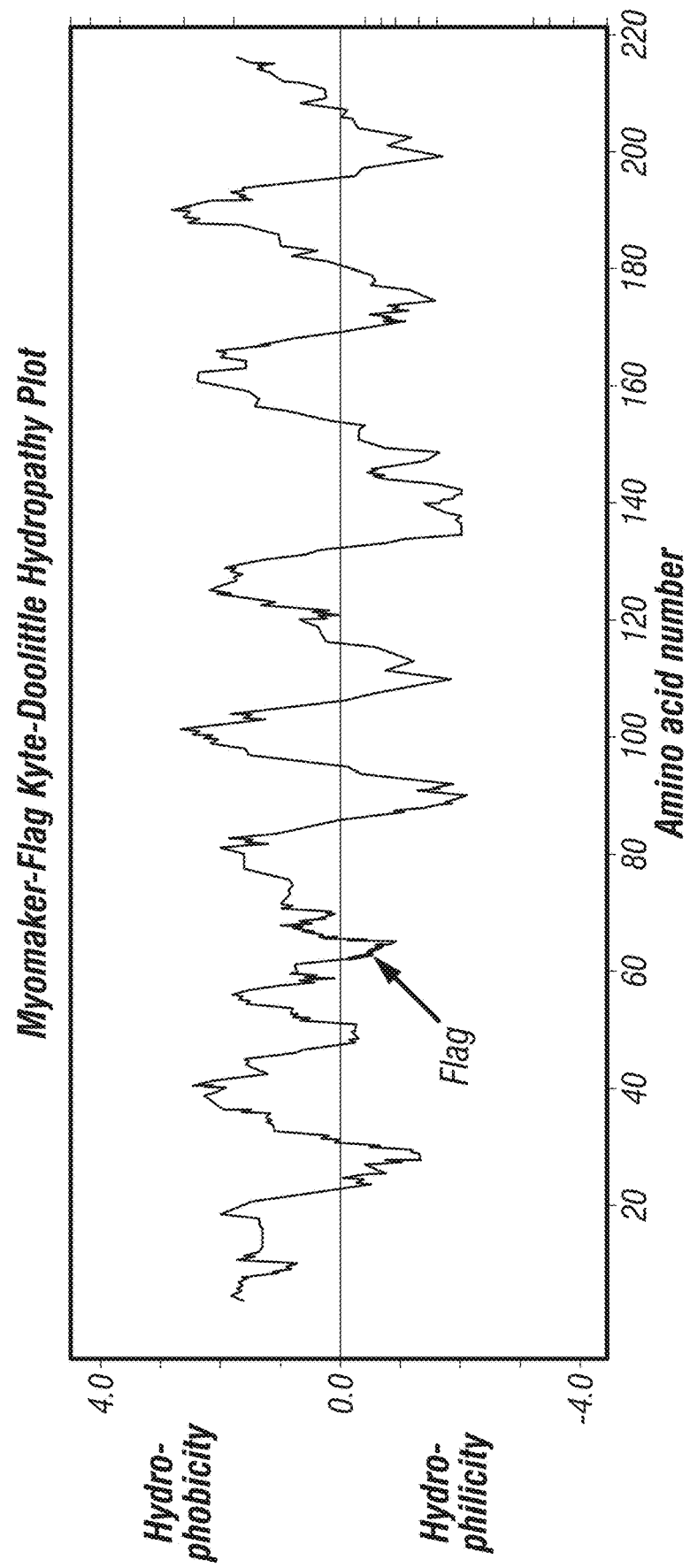

Myomaker is 221 amino acids in length and is highly conserved across vertebrate organisms, ranging from fish to humans (FIG. 10A). Analysis of the hydrophobicity of Myomaker using a Kyte-Doolittle Plot revealed extensive regions of hydrophobic character, suggesting this protein may localize to a cellular membrane (FIG. 10B). Myomaker does not contain predicted N-glycosylation sites. At the C-terminus, Myomaker possesses a C-A-A-X motif, the consensus for isoprenylation, which mediates membrane association[17]. Myomaker shares limited homology to a family of putative transmembrane hydrolases, named the CREST family[18], but it lacks a potentially critical histidine residue thought to be important for catalytic activity of hydrolases. The closest relative, Tmem8b, shares homology with Myomaker/Tmem8c in three hydrophobic domains; however Tmem8b is not muscle-specific and its forced expression in C2C12 cells did not promote fusion (data not shown). There is also a related protein in *Drosophila*, but it is more similar to Tmem8a and Tmem8b than to Myomaker/Tmem8c.

Figure 11D:
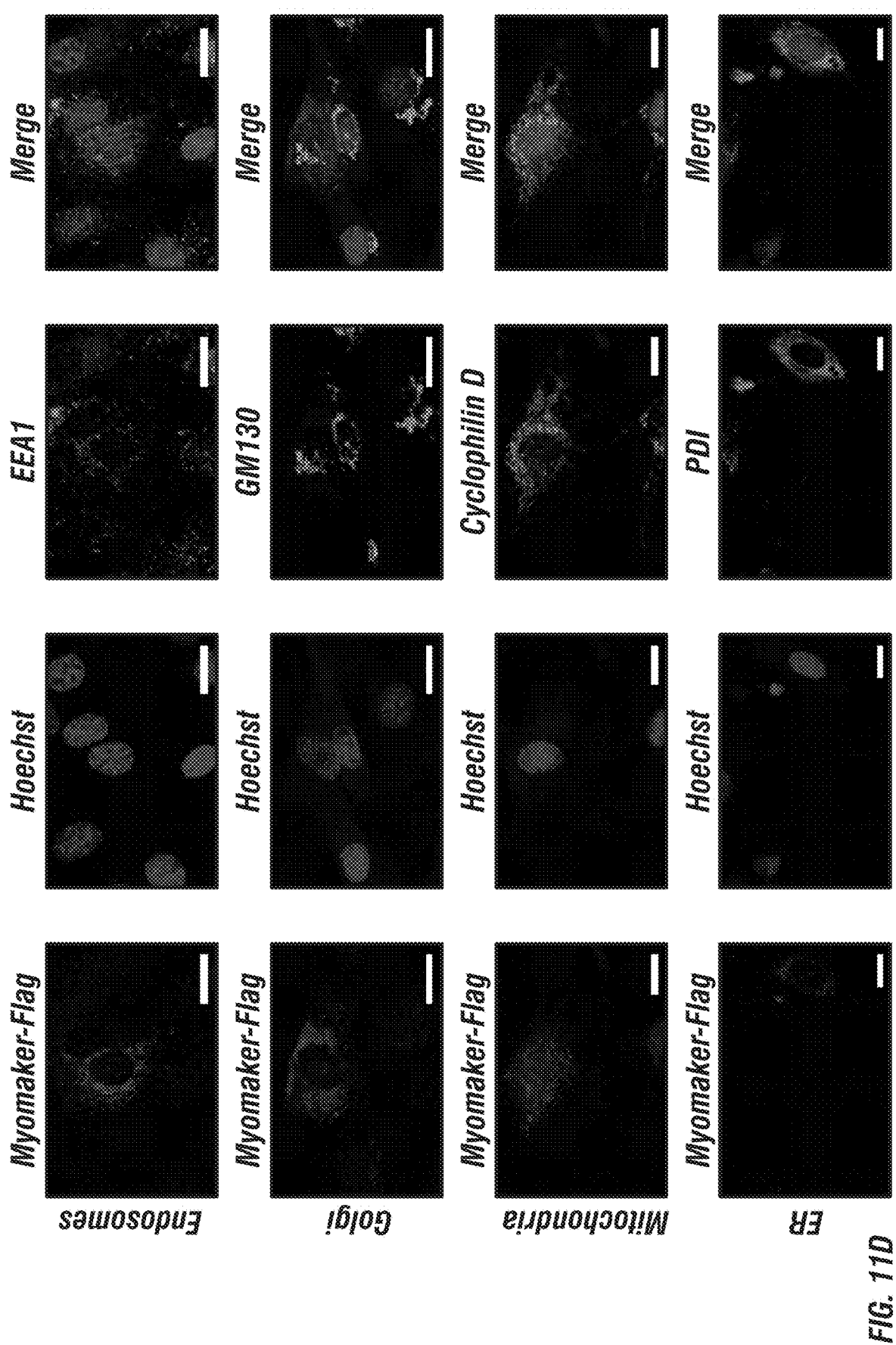

To analyze the cellular distribution of Myomaker, the inventors engineered a Flag epitope after amino acid 61, in a region of the protein that would not be predicted to perturb the hydrophobic domains (FIG. 10B). The Flag-tagged Myomaker protein, referred to as Myomaker-Flag, was detected in whole cell lysates, by Flag western blots (FIG. 11A). Retroviral expression of Myomaker-Flag in C2C12 cells confirmed that insertion of the Flag epitope did not alter the function of Myomaker as assayed by its ability to robustly enhance myoblast fusion (FIG. 11B). Fractionation of C2C12 cells infected with Myomaker-Flag into membrane and cytosolic fractions, showed exclusive localization to the membrane fraction (FIG. 11C). Myomaker-Flag was readily detected on the surface of myoblasts, by staining live cells with a Flag antibody, a common method used to detect plasma membrane proteins (Corcoran and Duncan, 2004) (FIG. 4A). Moreover, in myoblast cultures undergoing fusion, Myomaker-Flag was detected at sites of cell-cell interaction (FIG. 4A). Immunocytochemistry of fixed and permeabilized C2C12 cells expressing Myomaker-Flag revealed intracellular vesicle localization of Myomaker-Flag, as expected for a membrane protein (FIG. 4C). Co-staining with intracellular organelle markers revealed some co-localization with endosomes and ER (FIG. 11D), suggesting that Myomaker transits through one or more intracellular membrane compartments.

Figure 12A:
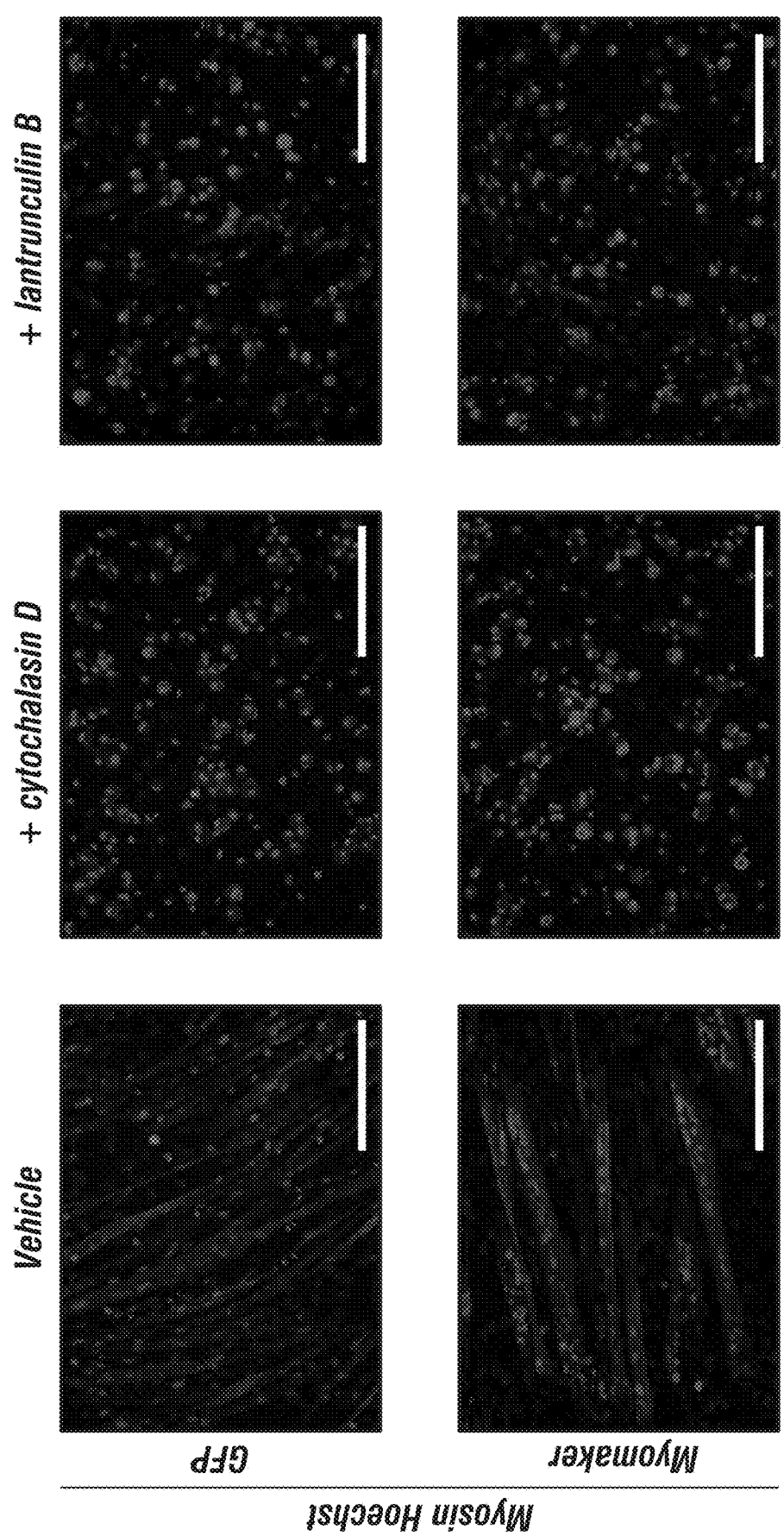
FIGS. 12A-B. A functional actin-cytoskeleton is necessary for myomaker function.
Figure 12B:
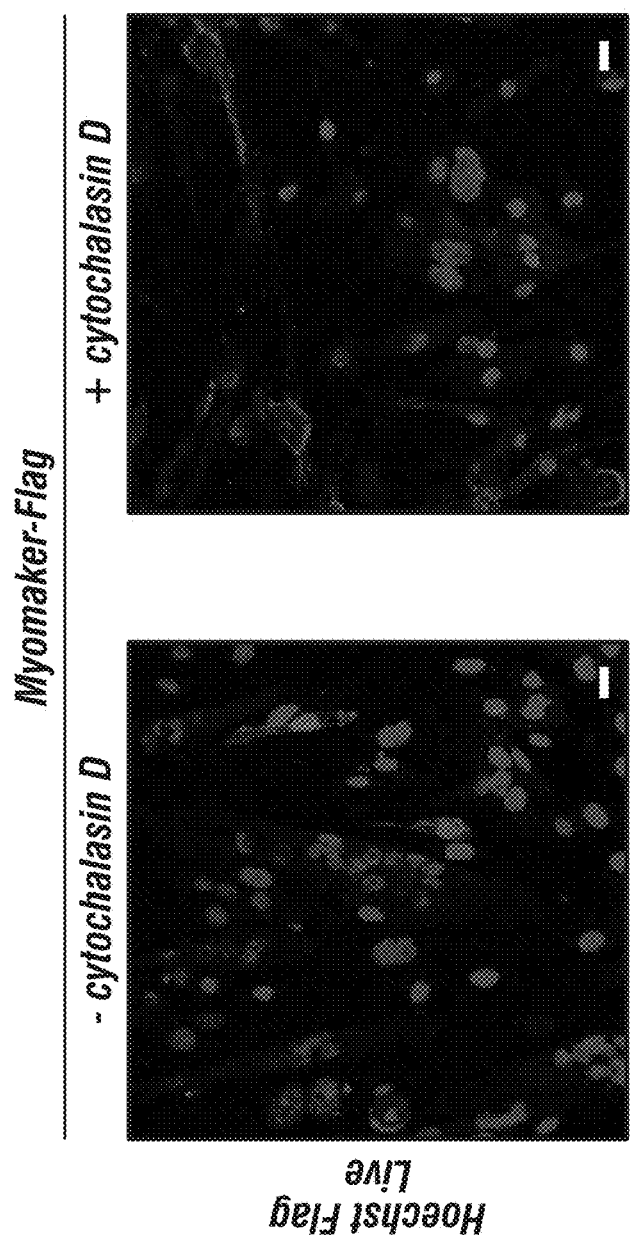

Myoblast fusion requires actin-cytoskeletal reorganization (Vasyutina et al., 2009; Gruenbaum-Cohen et al., 2012; Chen & Olson 2001; Chen et al., 2003; Nowak et al., 2009; and Laurin et al., 2008). Treating C2C12 cells with cytochalasin D and lantrunculin B, which perturb the cytoskeleton, completely blocked fusion in cells infected with GFP or Myomaker virus suggesting that actin nucleation is required for the fusogenic function of Myomaker (FIG. 12A). After cytochalasin D treatment, Myomaker-Flag was properly localized to the membrane, indicating that actin dynamics do not regulate transport of the protein to the cell surface (FIG. 12B).

Investigation of the Fusogenic Functions of Myomaker.

Figure 5A:
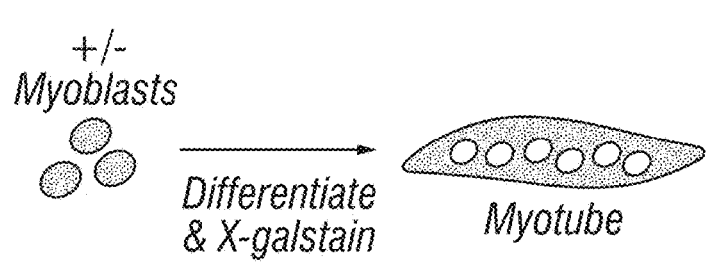
FIGS. 5A-E. Myomaker participates in the myoblast membrane fusion reaction.
Figure 5A:
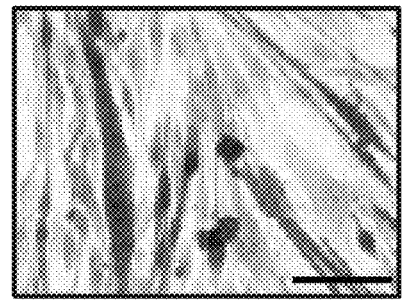
Figure 5A:
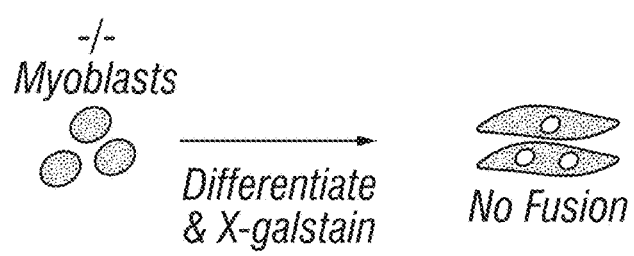
Figure 5A:
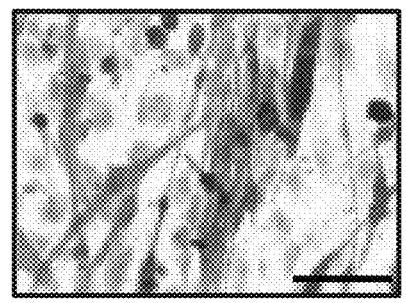
Figure 5A:
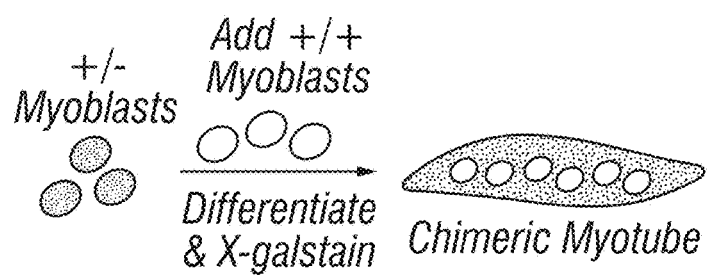
Figure 5A:
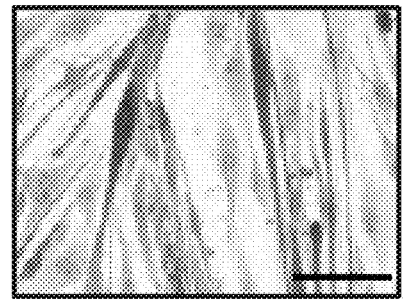
Figure 5A:
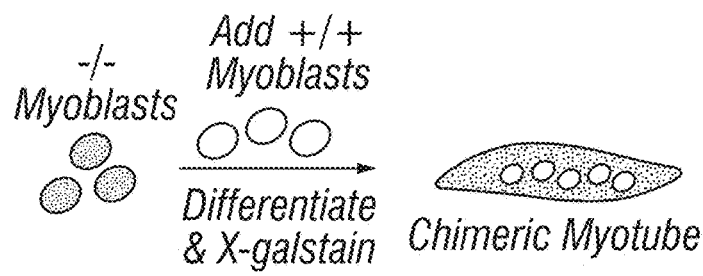
Figure 5A:
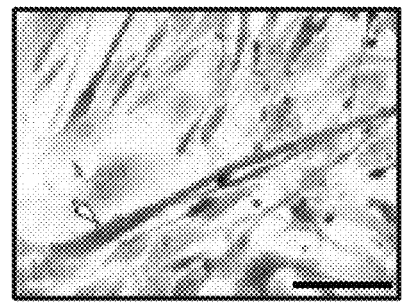
Figure 5B:
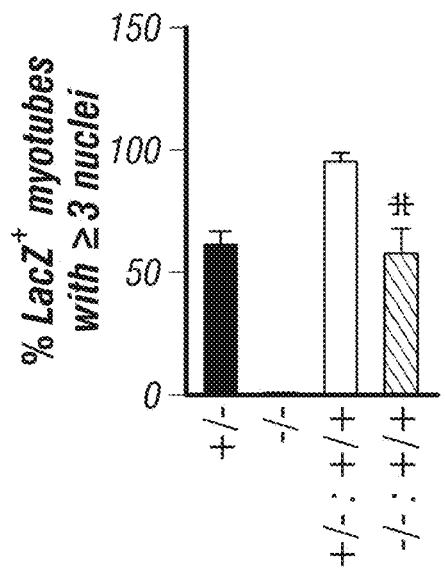
Figure 5C:
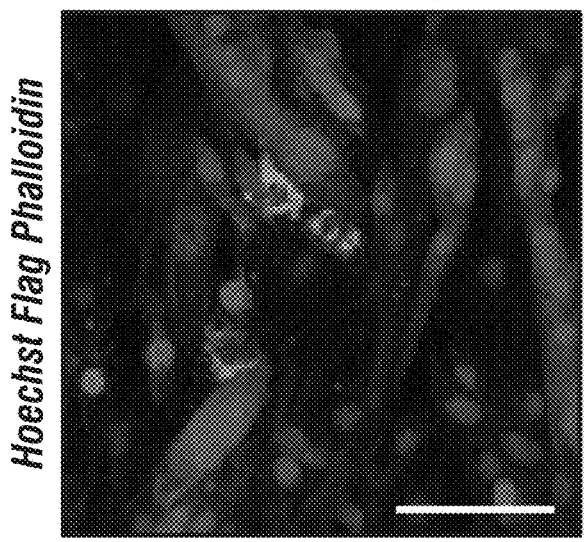

To further understand the mechanism of action of Myomaker, the inventors performed cell-mixing experiments using primary myoblasts from WT, Myomaker$^{+/-}$ and Myomaker$^{-/-}$ embryos (FIG. 5A). After differentiation for 4 days, the inventors visualized beta-galactosidase expression from the lacZ allele in Myomaker$^{+/-}$ and Myomaker$^{-/-}$ myoblasts to monitor fusion between different myoblast populations. As a co-stain, they used nuclear fast red, which stains a nucleus red and confers a pink appearance in the cytoplasm of cells. Myomaker$^{+/-}$ myoblasts formed multi-nucleated myotubes alone, without WT myoblasts, while Myomaker$^{-/-}$ myoblasts failed to fuse (FIG. 5A). Chimeric myotubes (blue/pink) were apparent in cultures containing WT and Myomaker$^{+/-}$ myoblasts, indicating fusion between these two myoblast populations (FIG. 5A). In cultures containing both WT and Myomaker$^{-/-}$ myoblasts, the inventors observed myotubes containing LacZ staining eminating from Myomaker$^{-/-}$ myoblasts (FIG. 5A). Quantification of the percent of LacZ$^+$ myotubes with 3 or more nuclei revealed that Myomaker$^{-/-}$ myoblasts could only form these structures in the presence of WT myoblasts (FIG. 5B). The inventors conclude that a cell with a functional copy of Myomaker can fuse with a Myomaker$^{-/-}$ myoblast, suggesting that Myomaker is absolutely required on the surface of only one of the fusing muscle cells. The inventors further investigated this possibility by analyzing expression of Myomaker-Flag in C2C12 cells and detected Myomaker-Flag in mononuclear C2C12 cells but not in previously fused multi-nucleated myotubes (FIG. 5C).

Figure 5E:
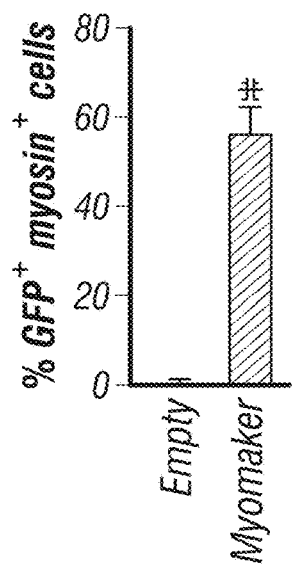
Figure 5D:
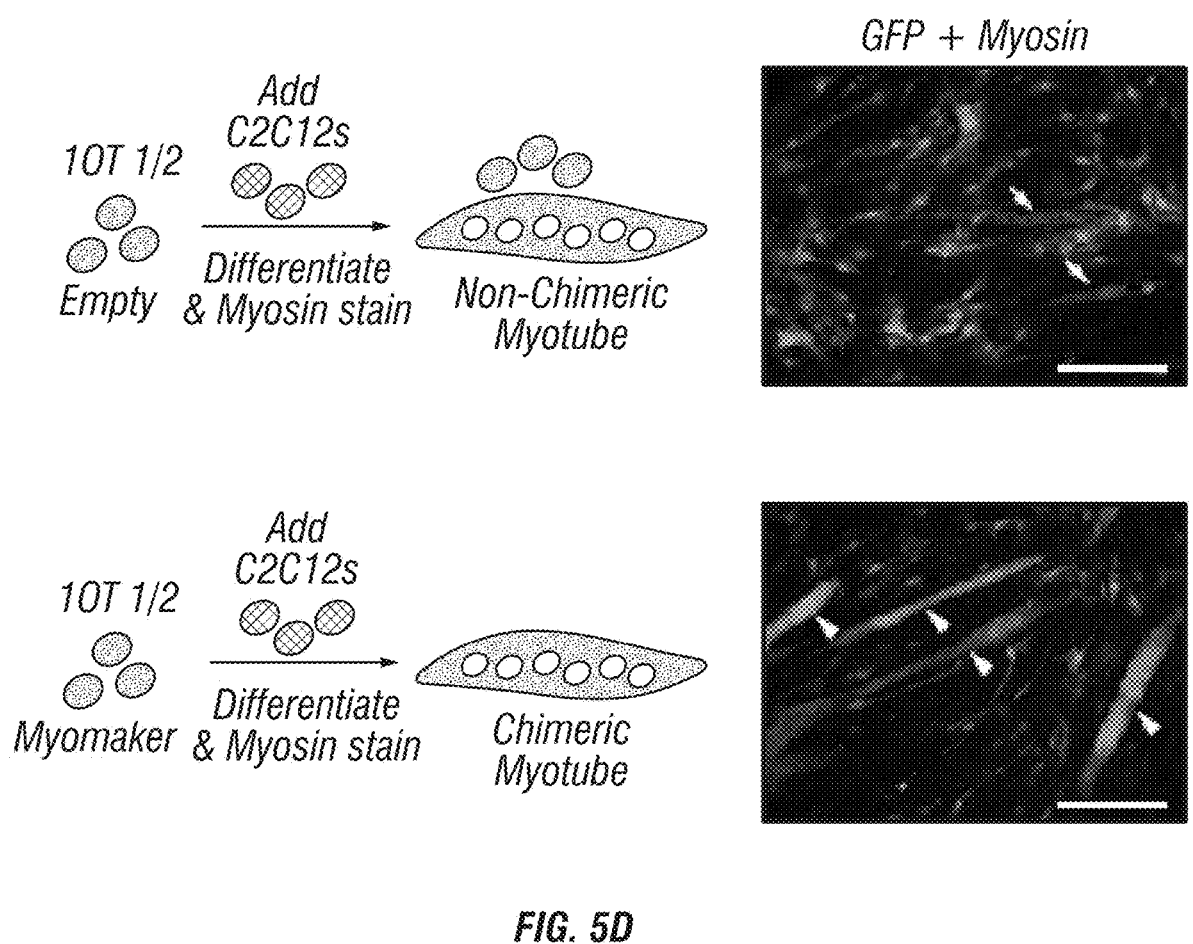

To determine whether over-expression of Myomaker could permit fusion of fibroblasts, a cell type that lacks fusion capability, the inventors infected 10T1/2 fibroblasts with a GFP virus and either empty virus, as a control, or Myomaker virus and then mixed these fibroblasts with C2C12 cells (FIG. 5D). The inventors did not detect fusion of GFP-empty virus-infected fibroblasts with myosin-positive cells, however GFP-Myomaker-infected fibroblasts robustly fused with C2C12 cells (FIG. 5D and data not shown). Quantitation of the myotubes expressing both GFP and myosin confirmed a striking ability of fibroblasts expressing Myomaker to fuse with myoblasts (FIG. 5E).

Figure 13B:
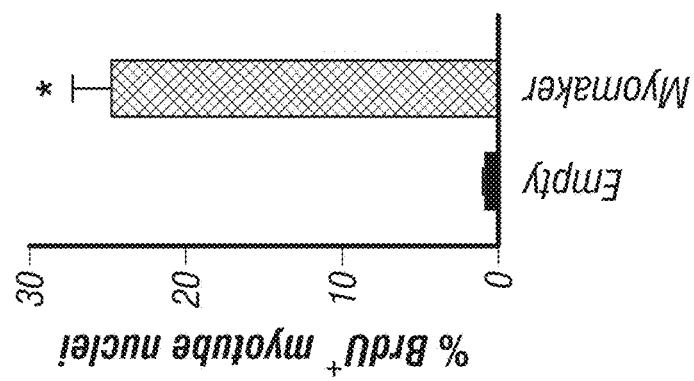
(FIG. 13B) Quantitation of the percentage of myotube nuclei that were BrdU+ in the indicated cultures. Scale bars: 100 μm.
Figure 13A:
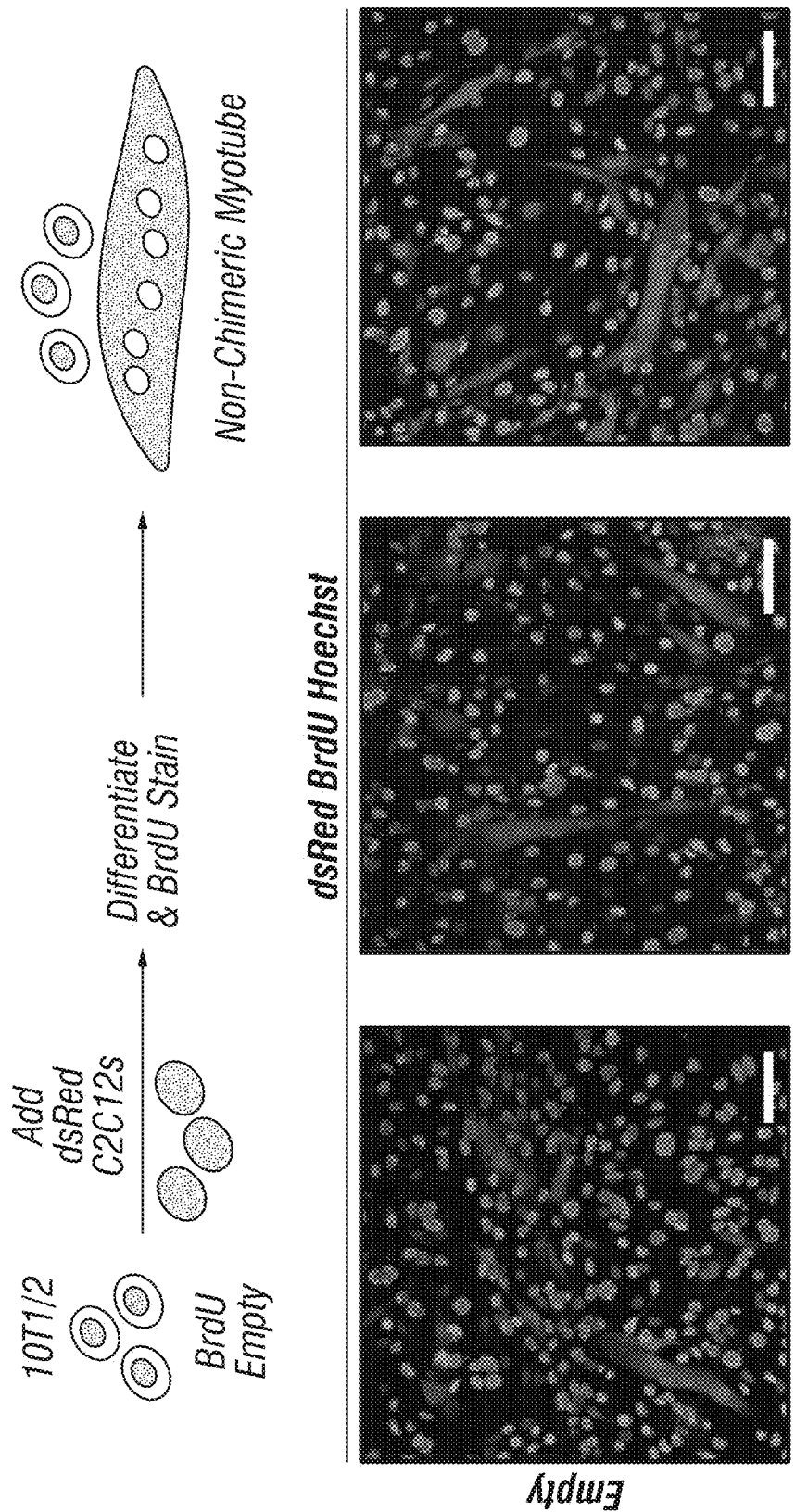
(FIG. 13A) 10T1/2 fibroblasts were treated with BrdU overnight and then infected with either Empty- or myomaker-retrovirus, followed by mixing with dsRed-infected C2C12 cells and induced to differentiate for 4 days. Analysis of BrdU incorporation in dsRed-myotubes (arrows) revealed myomaker was sufficient to fuse fibroblasts to C2C12 cells. The inventors observed empty-infected BrdU+ fibroblasts juxtaposed to dsRed-myotubes, but negligible fusion.
Figure 13A:
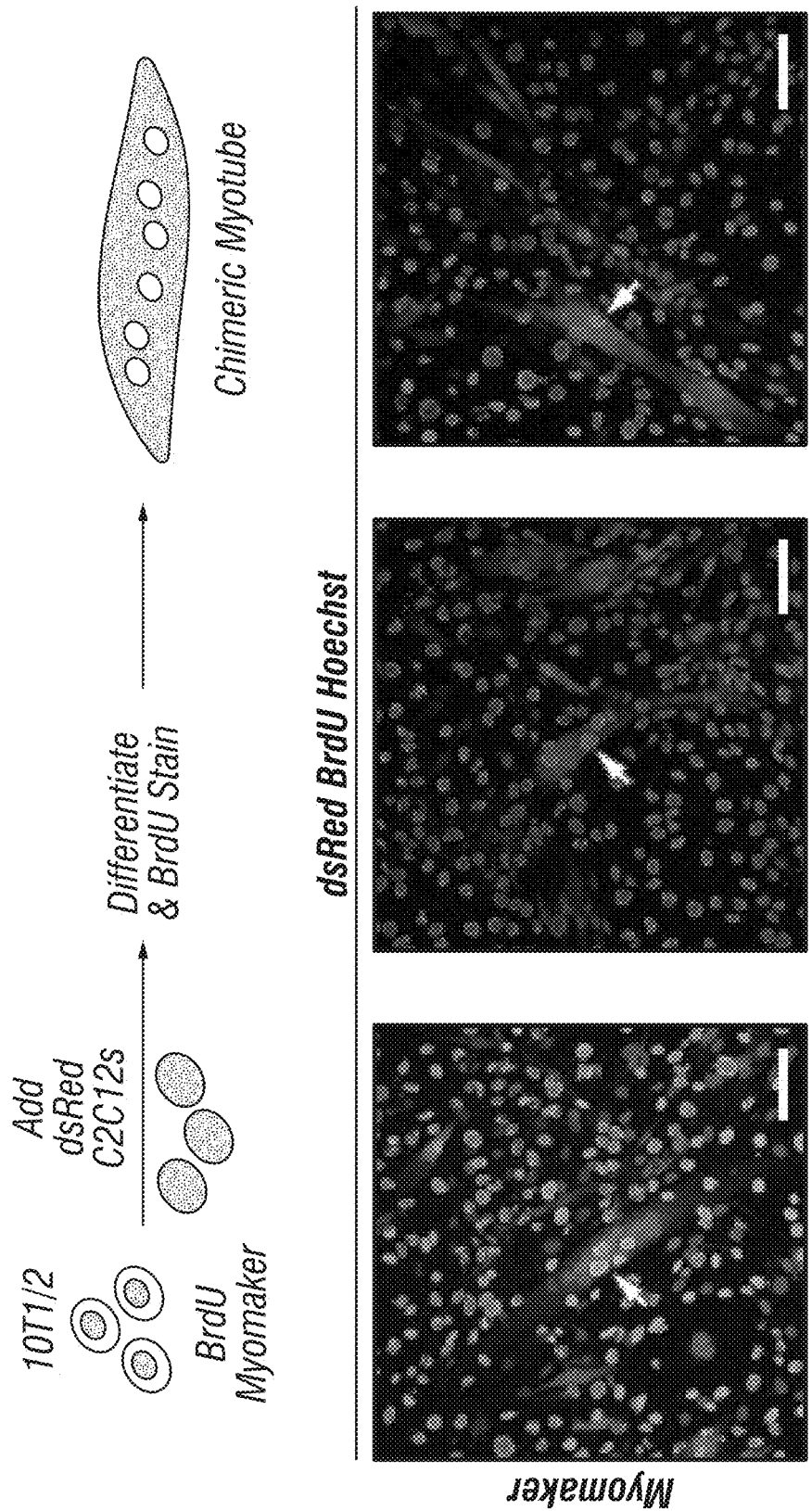

To control for the possibility that Myomaker-expressing fibroblasts were leaky and allowed GFP to diffuse into C2C12 myotubes, the inventors designed a complementary cell mixing experiment in which they tracked fibroblast nuclei by labeling with BrdU, followed by mixing with dsRed-infected C2C12 cells (FIG. 13A). BrdU-positive nuclei from fibroblasts expressing Myomaker were detected within C2C12 myotubes, confirming that Myomaker expression was sufficient to direct the fusion of fibroblasts to myoblasts (FIGS. 13A-B). Myomaker was not sufficient to induce fusion of fibroblasts in the absence of myoblasts. The finding that Myomaker can promote fusion of fibroblasts to myoblasts but cannot promote fibroblast-fibroblast fusion suggests that additional myoblast cell surface proteins are required for proper fusogenic engagement of the two membranes.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

X. References

The following references, to the extent that they provide exemplary procedural or other details supplementary to those set forth herein, are specifically incorporated herein by reference.

U.S. Pat. No. 4,683,202
U.S. Pat. No. 5,928,906
U.S. Pat. No. 4,659,774
U.S. Pat. No. 4,816,571
U.S. Pat. No. 5,141,813
U.S. Pat. No. 5,264,566
U.S. Pat. No. 4,959,463
U.S. Pat. No. 5,428,148
U.S. Pat. No. 5,554,744
U.S. Pat. No. 5,574,146
U.S. Pat. No. 5,602,244
U.S. Pat. No. 4,682,195
U.S. Pat. No. 4,946,778
U.S. Pat. No. 5,645,897
U.S. Pat. No. 5,705,629
U.S. Pat. No. 5,925,565
U.S. Pat. No. 5,935,819
U.S. Pat. No. 5,670,488
U.S. Pat. No. 5,932,210
U.S. Pat. No. 5,858,744
U.S. Pat. No. 5,739,018
U.S. Pat. No. 5,879,934
U.S. Pat. No. 5,851,826
U.S. Pat. No. 6,013,516
U.S. Pat. No. 5,994,136
U.S. Pat. No. 5,871,983
U.S. Pat. No. 5,994,624
U.S. Pat. No. 5,871,982
U.S. Pat. No. 5,981,274
U.S. Pat. No. 5,945,100
U.S. Pat. No. 5,780,448
U.S. Pat. No. 5,736,524
U.S. Pat. No. 5,702,932
U.S. Pat. No. 5,656,610
U.S. Pat. No. 5,589,466
U.S. Pat. No. 5,580,859
U.S. Pat. No. 5,610,042
U.S. Pat. No. 5,322,783
U.S. Pat. No. 5,563,055
U.S. Pat. No. 5,550,318
U.S. Pat. No. 5,538,877
U.S. Pat. No. 5,538,880
U.S. Pat. No. 5,302,523
U.S. Pat. No. 5,464,765
U.S. Pat. No. 4,684,611
U.S. Pat. No. 4,952,500
U.S. Pat. No. 5,384,253
U.S. Pat. No. 5,789,215
Abmayr and Pavlath, *Development,* 139:641-656, 2012.
Almendro et al., *J. Immunol.,* 157(12):5411-5421, 1996.
Ausubel et al., In: *Current Protocols in Molecular Biology,* John, Wiley & Sons, Inc, New York, 1994.

Barany and Merrifield, In: *The Peptides*, Gross and Meienhofer (Eds.), Academic Press, NY, 1-284, 1979.
Bates, *Mol. Biotechnol.*, 2(2):135-145, 1994.
Battraw and Hall, *Theor. App. Genet.*, 82(2):161-168, 1991.
Bentzinger et al., *Cold Spring Harb Perspect Biol*, 4, 2012.
Berkes and Tapscott, *Semin Cell Dev Biol*, 16:585-595, 2005.
Bett et al., *J. Virololgy*, 67(10):5911-5921, 1993.
Bhattacharjee et al., *J. Plant Bioch. Biotech.*, 6(2):69-73. 1997.
Bilbao et al., *Transplant Proc.*, 31(1-2):792-793, 1999.
Buckingham, *Curr Opin Genet Dev*, 16:525-532, 2006.
Caplen et al., Gene, 252(1-2):95-105, 2000.
Carbonelli et al., "*FEMS Microbiol Lett.* 177(1):75-82, 1999.
Chandler et al., *Proc. Natl. Acad. Sci. USA*, 94(8):3596-601, 1997.
Charrasse et al., *J Cell Biol*, 158:953-965, 2002.
Charrasse et al., *Mol Biol Cell*, 18:1734-1743, 2007.
Chen et al., *Cell*, 114:751-762, 2003.
Chen and Okayama, *Mol. Cell. Biol.* 7:2745-2752, 1987.
Chen and Olson, *Dev Cell*, 1:705-715, 2001.
Chen and Olson, *Science*, 308, 369-373, 2005.
Chillon et al., *J. Virol.*, 73(3):2537-2540, 1999.
Christou et al., *Proc. Natl. Acad. Sci. USA*, 84(12):3962-3966, 1987.
Cocea, *Biotechniques*, 23(5):814-816, 1997.
Coffey et al., *Science*, 282(5392):1332-1334, 1999.
Corcoran and Duncan, *J Virol*, 78:4342-4351, 2004.
Davis et al., *Cell*, 51: 987-1000, 1987.
DeLuca et al., *J. Virol.*, 56(2):558-570, 1985.
Derby et al., *Hear Res.*, 134(1-2):1-8, 1999.
D'Halluin et al., *Plant Cell*, 4(12):1495-1505, 1992.
European Appln. EP 266 032
European Appln. EP 273 085
Fechheimer, et al., *Proc Natl Acad. Sci. USA*, 84:8463-8467, 1987.
Feng et al., *Nat. Biotechnol.*, 15(9):866-870, 1997.
Fisher et al., *Virology*, 217(1):11-22, 1996.
Fraley et al., *Proc. Natl. Acad. Sci. USA*, 76:3348-3352, 1979.
Froehler et al., *Nucleic Acids Res*, 14; (13):5399-407.
Garrido et al., *J. Neurovirol.*, 5(3):280-288, 1999.
Ghosh and Bachhawat, In: *Liver Diseases, Targeted Diagnosis and Therapy Using Specific Receptors and Ligands*, Wu and Wu (Eds.), Marcel Dekker, New York, 87-104, 1991.
Gnant et al., *J. Natl. Cancer Inst.*, 91(20):1744-1750, 1999.
Gopal, *Mol. Cell. Biol.*, 5:1188-1190, 1985.
Graham and Prevec *Mol. Biotechnol.*, 3(3):207-220, 1995.
Graham and Van Der Eb, *Virology* 52:456-467, 1973.
Griffin et al., *Dev Cell*, 17:649-661, 2009.
Gruenbaum-Cohen, et al., *Proc Natl Acad Sci USA*, 109: 11211-11216, 2012.
Harland and Weintraub, *J. Cell Biol.*, 101:1094-1099, 1985.
Hasty et al., *Nature*, 364:501-506, 1993.
Hayashi et al., *Neurosci. Lett.*, 267(1):37-40, 1999.
He et al., *Plant Cell Reports*, 14 (2-3):192-196, 1994.
Holzer et al., *Virology*, 253(1):107-114, 1999.
Hou and Lin, *Plant Physiology*, 111:166, 1996.
Howard et al., *Ann. NY Acad. Sci.*, 880:352-365, 1999.
Huard et al., *Neuromuscul Disord.*, 7(5):299-313, 1997.
Imai et al., *J. Virol.*, 72(5):4371-4378, 1998.
Kaeppler et al., *Plant Cell Reports*, 9:415-418, 1990.
Kaneda et al., *Science*, 243:375-378, 1989.
Kang and Krauss, *Curr Opin Clin Nutr Metab Care*, 13:243-248, 2010.
Kato et al., *J. Biol. Chem.*, 266(6):3361-3364, 1991.
Kaufman et al., *Surv. Ophthalmol.*, 43Suppl 1:S91-97, 1999.
Kohut et al., *Am. J. Physiol.*, 275(6 Pt 1):L1089-94, 1998.
Kooby et al., *FASEB J.*, 13(11):1325-1334, 1999.
Kraus et al., *FEBS Lett.*, 428(3):165-170, 1998.
Krisky et al., *Gene Ther.*, 5(11):1517-1530, 1998a.
Krisky et al., *Gene Ther.*, 5(12):1593-1603, 1998b.
Lachmann and Efstathiou, *Clin. Sci. (Colch)*, 96(6):533-541, 1999.
Lareyre et al., *J. Biol. Chem.*, 274(12):8282-8290, 1999.
Laurin, et al., *Proc Natl Acad Sci USA*, 105:15446-15451, 2008.
Lazzeri, *Methods Mol. Biol.*, 49:95-106, 1995.
Lee et al., *Korean J. Genet.*, 11(2):65-72, 1989.
Lee et al., *J. Auton. Nerv. Syst.*, 74(2-3):86-90, 1997.
Levenson et al., *Human Gene Therapy*, 9:1233-1236, 1998.
Lundstrom, *J. Recept. Signal Transduct. Res.*, 19(1-4):673-686, 1999.
Macejak and Sarnow, *Nature*, 353:90-94, 1991.
Marienfeld et al., *Gene Ther.*, 6(6):1101-1113, 1999.
Merrifield, *Science*, 232(4748):341-347 1986.
Miyatake et al., *Gene Ther.*, 6(4):564-572, 1999.
Moriuchi et al., *Cancer Res.*, 58(24):5731-5737, 1998.
Morrison et al., *J. Gen. Virol.*, 78(Pt 4):873-878, 1997.
Naldini et al., *Proc. Natl. Acad. Sci. USA*, 93(21):11382-11388, 1996.
Nicolau et al., *Methods Enzymol.*, 149:157-176, 1987
Nicolau and Sene, *Biochim. Biophys. Acta*, 721:185-190, 1982.
Nomoto et al., *Gene*, 236(2):259-271, 1999.
Nowak, et al., *J Cell Sci*, 122:3282-3293, 2009.
Parks et al., *J. Virol.*, 71(4):3293-8, 1997.
PCT Appln. WO 94/09699
PCT Appln. WO 95/06128
PCT Appln. WO 92/17598
Pelletier and Sonenberg, *Nature*, 334:320-325, 1988.
Perales et al., *Proc. Natl. Acad. Sci. USA*, 91:4086-4090, 1994.
Potrykus et al., *Mol. Gen. Genet.*, 199:183-188, 1985.
Potter et al., *Proc. Natl. Acad. Sci. USA*, 81:7161-7165, 1984.
Powell and Wright, *PLoS Biol*, 9:e1001216, 2011.
Omirulleh et al., *Plant Mol. Biol.*, 21(3):415-28, 1993.
Oren-Suissa and Podbilewicz, *Trends Cell Biol*, 17:537-546, 2007.
Rabinovitch et al., *Diabetes*, 48(6):1223-1229, 1999.
Reddy et al., *J. Virol.*, 72(2):1394-1402, 1998.
Rhodes et al., *Methods Mol. Biol.*, 55:121-131, 1995.
Rippe et al., "DNA-mediated gene transfer into adult rat hepatocytes in primary culture," *Mol. Cell Biol.*, 10:689-695, 1990.
Robbins and Ghivizzani, *Pharmacol. Ther.*, 80(1):35-47, 1998.
Robbins et al., *Proc. Natl. Acad. Sci. USA*, 95(17):10182-10187 1998.
Robbins et al., *Trends Biotechnol.*, 16(1):35-40, 1998.
Rochlin et al., *Dev Biol*, 341:66-83, 2010.
Sambrook et al., In: *Molecular Cloning: A Laboratory Manual*, Vol. 1, Cold Spring Harbor Laboratory Press, Cold Spring Harbor, N.Y., Ch. 7, 7.19-17.29, 1989.
Sambrook et al., In: *Molecular cloning*, Cold Spring Harbor Laboratory Press, Cold Spring Harbor, N.Y., 2001.
Schwander et al., *Dev Cell*, 4:673-685, 2003.
Shilagardi, et al., *Science*, 340:359-363, 2013.
Stewart and Young, "Solid Phase Peptide Synthesis", 2d. ed., Pierce Chemical Co., 1984.
Suzuki et al., *Oncogene*, 17:853-865, 1998.

Suzuki et al., *Biochem. Biophys. Res. Commun.*, 252(3):686-690, 1998.
Tam et al., *J. Am. Chem. Soc.*, 105:6442, 1983.
Treisman et al., *Genes Dev.* 11:1949-1962, 1997.
Tsukada et al., *Plant Cell Physiol.*, 30(4)599-604, 1989.
Tsumaki et al., *J. Biol. Chem.*, 273(36):22861-22864, 1998.
Tur-Kaspa et al., *Mol. Cell Biol.*, 6:716-718, 1986.
Vasyutina et al., *Proc Natl Acad Sci USA*, 106:8935-8940, 2009.
Walker et al., *Nucleic Acids Res.* 20(7):1691-1696, 1992.
Wagner et al., *Science*, 260:1510-1513, 1990.
Wang et al., *Mol. Cell. Biol.*, 19:284-295, 1998.
Wang et al., *Gynecol. Oncol.*, 71(2):278-287, 1998.
Wilson, *J. Clin. Invest.*, 98(11):2435, 1996.
Wilson and Snell, *Trends Cell Biol*, 8:93-96, 1998.
Webb et al., *Mol. Cell. Biol.* 11: 5197-5205, 1991.
Wong et al., *Gene*, 10:87-94, 1980.
Wu et al., *Biochem. Biophys. Res. Commun.*, 233(1):221-226, 1997.
Wu and Wu, *J. Biol. Chem.*, 262:4429-4432, 1987.
Yagami-Hiromasa, et al., *Nature*, 377:652-656, 1995.
Yamada et al., *Proc. Natl. Acad. Sci. USA*, 96(7):4078-4083, 1999.
Yeung et al., *Gene Ther.*, 6(9):1536-1544, 1999.
Yoon et al., *J. Gastrointest. Surg.*, 3(1):34-48, 1999.
Zhao-Emonet et al., *Biochim. Biophys. Acta*, 1442(2-3):109-119, 1998.
Zheng et al., *J. Gen. Virol.*, 80(Pt 7):1735-1742, 1999.
Zhou et al., *Exp. Hematol.*, 21:928-933, 1993.
Zufferey et al., *Nat. Biotechnol.*, 15(9):871-875, 1997.

What is claimed is:

1. An isolated non-muscle cell transformed with:
   a) an exogenous nucleic acid encoding a Myomaker polypeptide under the control of a promoter active in said cell; and
   b) a gene of interest other than Myomaker, wherein the gene of interest is a therapeutic gene,
   c) wherein the non-muscle cell is a human cell and wherein the Myomaker polypeptide is expressed on the surface of the transformed non-muscle cell such that the transformed non-muscle cell is able to fuse with a muscle cell to transfer the gene of interest to the muscle cell.

2. The non-muscle cell of claim 1, wherein said non-muscle cell is a fibroblast, bone marrow cell or blood cell.

3. The non-muscle cell of claim 1, wherein said exogenous nucleic acid is under the control of constitutive promoter.

4. The non-muscle cell of claim 1, wherein said exogenous nucleic acid is under the control of an inducible promoter.

5. The non-muscle cell of claim 1, wherein said exogenous nucleic acid is incorporated into a chromosome of said non-muscle cell.

6. The non-muscle cell of claim 1, wherein said exogenous nucleic acid is carried episomally by said non-muscle cell.

7. The non-muscle cell of claim 1, wherein said non-muscle cell expresses a detectable marker.

8. The non-muscle cell of claim 1, wherein the therapeutic gene corrects a pathologic phenotype.

* * * * *

SEQUENCE LISTING

```
<160> NUMBER OF SEQ ID NOS: 8

<210> SEQ ID NO 1
<211> LENGTH: 666
<212> TYPE: DNA
<213> ORGANISM: Homo sapiens

<400> SEQUENCE: 1
atggggacgc tggtggccaa gctgctcctg cccaccctca gcagcctggc cttcctcccc    60
actgtcagca tcgcggccaa gaggcggttc cacatggagg ccatggtcta cctcttcacc   120
ctgttcttcg tggcgctcca ccatgcctgc aatggacccg gcttgtctgt gctgtgcttc   180
atgcgtcacg acatcctgga gtatttcagt gtctacggga cagccctgag catgtgggtc   240
tcgctgatgg cactggccga cttcgacgaa cccaagaggt caacatttgt gatgttcggc   300
gtcctgacca ttgctgtgcg gatctaccat gaccgatggg gctacggggt gtactcgggc   360
cccatcggca cagccatcct catcatcgcg gcaaagtggc tacagaagat gaaggagaag   420
aagggcctgt acccagacaa gagcgtctac acccagcaga taggccccgg cctctgcttc   480
ggggcgctgg ccctgatgct acgcttcttc tttgaggact gggactacac ttatgtccac   540
agcttctacc actgtgccct ggctatgtcc tttgttctgc tgctgcccaa ggtcaacaag   600
aaggctggat ccccggggac cccggccaag ctggactgct ccaccctgtg ctgtgcttgt   660
gtctga                                                             666

<210> SEQ ID NO 2
<211> LENGTH: 221
<212> TYPE: PRT
<213> ORGANISM: Homo sapiens

<400> SEQUENCE: 2

Met Gly Thr Leu Val Ala Lys Leu Leu Leu Pro Thr Leu Ser Ser Leu
1               5                   10                  15

Ala Phe Leu Pro Thr Val Ser Ile Ala Ala Lys Arg Arg Phe His Met
            20                  25                  30

Glu Ala Met Val Tyr Leu Phe Thr Leu Phe Phe Val Ala Leu His His
        35                  40                  45

Ala Cys Asn Gly Pro Gly Leu Ser Val Leu Cys Phe Met Arg His Asp
    50                  55                  60

Ile Leu Glu Tyr Phe Ser Val Tyr Gly Thr Ala Leu Ser Met Trp Val
65                  70                  75                  80

Ser Leu Met Ala Leu Ala Asp Phe Asp Glu Pro Lys Arg Ser Thr Phe
                85                  90                  95
```

```
Val Met Phe Gly Val Leu Thr Ile Ala Val Arg Ile Tyr His Asp Arg
            100                 105                 110

Trp Gly Tyr Gly Val Tyr Ser Gly Pro Ile Gly Thr Ala Ile Leu Ile
            115                 120                 125

Ile Ala Ala Lys Trp Leu Gln Lys Met Lys Glu Lys Lys Gly Leu Tyr
130                 135                 140

Pro Asp Lys Ser Val Tyr Thr Gln Gln Ile Gly Pro Gly Leu Cys Phe
145                 150                 155                 160

Gly Ala Leu Ala Leu Met Leu Arg Phe Phe Glu Asp Trp Asp Tyr
                165                 170                 175

Thr Tyr Val His Ser Phe Tyr His Cys Ala Leu Ala Met Ser Phe Val
            180                 185                 190

Leu Leu Leu Pro Lys Val Asn Lys Lys Ala Gly Ser Pro Gly Thr Pro
            195                 200                 205

Ala Lys Leu Asp Cys Ser Thr Leu Cys Cys Ala Cys Val
            210                 215                 220

<210> SEQ ID NO 3
<211> LENGTH: 666
<212> TYPE: DNA
<213> ORGANISM: Mus musculus

<400> SEQUENCE: 3
atggggacag ttgtagccaa actgctcctg cctacccttca gcagcctggc cttcctcccg        60
acagtgagca tcgctaccaa gaggcgtttc tacatggagg ccatggtcta cctcttcacc       120
atgttctttg tggcgttctc ccatgcctgt gatgggcctg gtttgtctgt gctgtgcttc       180
atgcgccgtg acattctgga gtacttcagc atctatggaa cagccctgag catgtgggtc       240
tccctgatgg cactggccga cttttgatgaa ccccagagat cgaccttcac aatgcttggc       300
gtccttacca tcgctgtgcg gacttttcat gaccgctggg gttacggggt atactccggt       360
cccataggca cggccaccct catcattgct gtaaagtggc tgaagaagat gaaagagaag       420
aagggcctgt accccgacaa gagcatctac acccagcaga taggccccgg cctgtgcttt       480
ggggccctgg ccctgatgct tcgattcttc tttgaggaat gggattacac ctacgtccac       540
agcttctacc actgtgccct ggccatgtcc tttgtcctgc tgctgcccaa ggtcaacaag       600
aaggctggga acgcagggc ccccgccaag ctgaccttct ccacccctctg ctgcacttgt       660 gtctga                                                                  666

<210> SEQ ID NO 4
<211> LENGTH: 221
<212> TYPE: PRT
<213> ORGANISM: Mus musculus

<400> SEQUENCE: 4

Met Gly Thr Val Val Ala Lys Leu Leu Leu Pro Thr Leu Ser Ser Leu
1               5                   10                  15

Ala Phe Leu Pro Thr Val Ser Ile Ala Thr Lys Arg Arg Phe Tyr Met
            20                  25                  30

Glu Ala Met Val Tyr Leu Phe Thr Met Phe Val Ala Phe Ser His
            35                  40                  45

Ala Cys Asp Gly Pro Gly Leu Ser Val Leu Cys Phe Met Arg Arg Asp
        50                  55                  60

Ile Leu Glu Tyr Phe Ser Ile Tyr Gly Thr Ala Leu Ser Met Trp Val
65                  70                  75                  80
```

```
Ser Leu Met Ala Leu Ala Asp Phe Asp Glu Pro Gln Arg Ser Thr Phe
                85                  90                  95
Thr Met Leu Gly Val Leu Thr Ile Ala Val Arg Thr Phe His Asp Arg
            100                 105                 110
Trp Gly Tyr Gly Val Tyr Ser Gly Pro Ile Gly Thr Ala Thr Leu Ile
        115                 120                 125
Ile Ala Val Lys Trp Leu Lys Lys Met Lys Glu Lys Lys Gly Leu Tyr
130                 135                 140
Pro Asp Lys Ser Ile Tyr Thr Gln Gln Ile Gly Pro Gly Leu Cys Phe
145                 150                 155                 160
Gly Ala Leu Ala Leu Met Leu Arg Phe Phe Glu Glu Trp Asp Tyr
            165                 170                 175
Thr Tyr Val His Ser Phe Tyr His Cys Ala Leu Ala Met Ser Phe Val
        180                 185                 190
Leu Leu Leu Pro Lys Val Asn Lys Lys Ala Gly Asn Ala Gly Ala Pro
            195                 200                 205
Ala Lys Leu Thr Phe Ser Thr Leu Cys Cys Thr Cys Val
210                 215                 220
```

<210> SEQ ID NO 5
<211> LENGTH: 19
<212> TYPE: DNA
<213> ORGANISM: Artificial Sequence
<220> FEATURE:
<223> OTHER INFORMATION: Synthetic Primer

<400> SEQUENCE: 5
atcgctacca agaggcgtt                                                19

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
cacagcacag acaaaccagg                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
atggggacag ttgtagccaa                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
tcagacacaa gtgcagcaga                                               20